US012364657B2

(12) United States Patent
Herrlein et al.

(10) Patent No.: US 12,364,657 B2
(45) Date of Patent: *Jul. 22, 2025

(54) METHOD FOR COATING KERATIN FIBERS

(71) Applicant: HFC Prestige Service Germany GmbH, Darmstadt (DE)

(72) Inventors: Mathias Kurt Herrlein, Kronberg (DE); Graham Neil Mckelvey, Hesse (DE); Matija Crne, Wiesbaden (DE); Simon Paul Godfrey, Oberursel (DE); Corinne Violette Mohr, Lorsch (DE); Ingo Weber, Basel (DE); Swapna Pinakattu, Reinheim (DE); Patrick Alexander Kiefer, Darmstadt (DE); Petra Barbara Braun, Münster (DE); Andrej Gross, Darmstadt (DE); Felix Herkner, Eppstein (DE); Axel Meyer, Frankfurt am Main (DE); Carl Uwe Oswald Ludwig Schmidt, Reinheim (DE)

(73) Assignee: WELLA GERMANY GMBH, Darmstadt (DE)

(*) Notice: Subject to any disclaimer, the term of this patent is extended or adjusted under 35 U.S.C. 154(b) by 796 days.

This patent is subject to a terminal disclaimer.

(21) Appl. No.: 17/362,414

(22) Filed: Jun. 29, 2021

(65) Prior Publication Data
US 2021/0401713 A1 Dec. 30, 2021

Related U.S. Application Data

(60) Provisional application No. 63/046,110, filed on Jun. 30, 2020.

(51) Int. Cl.
| | |
|---|---|
| *A61Q 5/06* | (2006.01) |
| *A45D 19/00* | (2006.01) |
| *A61K 8/58* | (2006.01) |
| *A61K 8/89* | (2006.01) |
| *A61Q 5/10* | (2006.01) |
| *A61Q 5/12* | (2006.01) |

(52) U.S. Cl.
CPC ............ *A61K 8/585* (2013.01); *A45D 19/005* (2021.01); *A45D 19/0066* (2021.01); *A61K 8/89* (2013.01); *A61Q 5/06* (2013.01); *A61Q 5/065* (2013.01); *A61Q 5/10* (2013.01); *A61Q 5/12* (2013.01); *A61K 2800/43* (2013.01); *A61K 2800/4324* (2013.01); *A61K 2800/884* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 4,559,057 A | 12/1985 | Bogaty et al. | |
| 5,258,481 A | 11/1993 | Hesselmans et al. | |
| 5,567,428 A | 10/1996 | Hugehes | |
| 5,990,479 A | 11/1999 | Weiss et al. | |
| 6,225,198 B1 | 5/2001 | Alivisatos et al. | |
| 6,451,747 B1 | 9/2002 | Decoster | |
| 6,492,484 B2 | 12/2002 | Misumi et al. | |
| 9,546,301 B2 | 1/2017 | Derksen et al. | |
| 10,011,677 B2 | 7/2018 | Yamashita et al. | |
| 10,959,919 B2 | 3/2021 | Dahne et al. | |
| 10,973,754 B2 | 4/2021 | Herrlein et al. | |
| 11,324,688 B2 | 5/2022 | Herrlein et al. | |
| 11,478,415 B2 | 10/2022 | Herrlein et al. | |
| 2003/0203978 A1 | 10/2003 | O'Brien et al. | |
| 2004/0010863 A1 | 1/2004 | Gawtrey et al. | |
| 2005/0226838 A1 | 10/2005 | Krause et al. | |
| 2006/0041026 A1 | 2/2006 | Mahr et al. | |
| 2007/0134180 A1 | 6/2007 | Simard et al. | |
| 2008/0108740 A1 | 5/2008 | Evers | |
| 2008/0184496 A1 | 8/2008 | Brun et al. | |
| 2009/0233062 A1 | 9/2009 | Nakamura et al. | |
| 2010/0083446 A1 | 4/2010 | Brun et al. | |
| 2010/0088036 A1 | 4/2010 | Goddard-Clark et al. | |
| 2011/0061179 A1 | 3/2011 | Cremer et al. | |
| 2011/0083284 A1 | 4/2011 | Suddaby et al. | |
| 2014/0242281 A1 | 8/2014 | Swarup et al. | |
| 2014/0336093 A1 | 11/2014 | Koellnberger | |
| 2015/0174051 A1 | 6/2015 | Teboul | |

(Continued)

FOREIGN PATENT DOCUMENTS

| | | | |
|---|---|---|---|
| CN | 205683359 U | * | 11/2016 |
| CN | 111432887 A | | 7/2020 |

(Continued)

OTHER PUBLICATIONS

Curly Hair Lounge. https://web.archive.org/web/20150828231722/https://curlyhairlounge.com/what-is-product-build-up. Published: Aug. 14, 2015.*
CN205683359 Eng Tran. Published: Nov. 16, 2016.*
International Search Report issued in connection with PCT Application No. PCT/EP2019/057811 dated Sep. 4, 2019.
International Application Seriai No. PCT/EP2019/057814, Invitation to Pay Additional Fees mailed Jul. 26, 2019.
International Search Report and Written Opinion received for PCT Patent Application No. PCT/EP2019/068186, mailed on Feb. 2, 2020.
International Search Report and Written Opinion received for PCT Patent Application No. PCT/EP2019/068187, mailed on Dec. 4, 2019.

(Continued)

*Primary Examiner* — Nicole P Babson
*Assistant Examiner* — Lori K Mattison
(74) *Attorney, Agent, or Firm* — Dennemeyer & Associates LLC

(57) ABSTRACT

A film coating for keratin fibers is described. The film coating is produced by applying to the keratin fibers a pretreatment composition and a film forming composition and curing the compositions to produce the film coating. The coating may be clear and function as a styling, conditioning and holding. The coating alternatively may contain pigment particles and provide a color coating.

5 Claims, No Drawings

(56) References Cited

U.S. PATENT DOCUMENTS

| | | |
|---|---|---|
| 2016/0120284 A1 | 5/2016 | Crne et al. |
| 2016/0120285 A1 | 5/2016 | Crne et al. |
| 2016/0175212 A1 | 6/2016 | Zhou et al. |
| 2016/0235655 A1 | 8/2016 | Herrlein et al. |
| 2016/0271049 A1 | 9/2016 | Schulze et al. |
| 2017/0001045 A1 | 1/2017 | Aubert et al. |
| 2017/0158888 A1 | 6/2017 | Kang et al. |
| 2017/0189312 A1 | 7/2017 | Van Nguyen et al. |
| 2017/0189314 A1 | 7/2017 | Elsen-wahrer et al. |
| 2018/0105717 A1 | 4/2018 | Swarup et al. |
| 2018/0105718 A1 | 4/2018 | Swarup et al. |
| 2018/0263353 A1 | 9/2018 | Crne et al. |
| 2018/0263354 A1 | 9/2018 | Crne et al. |
| 2021/0220251 A1 | 7/2021 | Speckbacher et al. |
| 2021/0401713 A1 | 12/2021 | Herrlein et al. |
| 2022/0054392 A1 | 2/2022 | Herrlein et al. |

FOREIGN PATENT DOCUMENTS

| | | | |
|---|---|---|---|
| CN | 111432888 A | 7/2020 | |
| DE | 19913625 A1 | 9/2000 | |
| DE | 102006011271 A1 | 9/2007 | |
| EP | 132960 A2 | 2/1985 | |
| EP | 1184426 A2 | 3/2002 | |
| EP | 1600149 A1 | 11/2005 | |
| EP | 1825883 A1 | 8/2007 | |
| EP | 3015134 A1 | 5/2016 | |
| EP | 3015135 A1 | 5/2016 | |
| EP | 3058934 A1 | 8/2016 | |
| EP | 3058989 A1 | 8/2016 | |
| EP | 3397346 A1 | 11/2018 | |
| FR | 2899795 A1 | 10/2007 | |
| JP | S 50-034400 A | 4/1975 | |
| JP | S 60-105608 A | 6/1985 | |
| JP | 2005-350460 A | 12/2005 | |
| JP | 2007-084510 A | 4/2007 | |
| JP | 2008-502613 A | 1/2008 | |
| JP | 2009-520002 A | 5/2009 | |
| JP | 2010-530842 A | 9/2010 | |
| JP | 2012-515219 A | 7/2012 | |
| JP | 2012-530841 A | 12/2012 | |
| JP | 2015-521646 A | 7/2015 | |
| JP | 2017-533224 A | 11/2017 | |
| KR | 101603845 B1 | 3/2016 | |
| KR | 20190028636 A | 3/2019 | |
| WO | 2005065632 A1 | 7/2005 | |
| WO | 2007071706 A1 | 6/2007 | |
| WO | 2009073759 A1 | 6/2009 | |
| WO | 2011128255 A1 | 10/2011 | |
| WO | WO-2012055805 A1 * | 5/2012 | ............. A61K 8/585 |
| WO | 2015097308 A1 | 7/2015 | |
| WO | 2016066747 A1 | 5/2016 | |
| WO | 2017108599 A1 | 6/2017 | |
| WO | 2017117543 A1 | 7/2017 | |
| WO | 2017189585 A1 | 11/2017 | |
| WO | 2017220781 A1 | 12/2017 | |
| WO | 2018039314 A1 | 3/2018 | |
| WO | 2018130912 A1 | 7/2018 | |
| WO | 2018185345 A1 | 10/2018 | |
| WO | 2018234530 A1 | 12/2018 | |
| WO | 2019071204 A1 | 4/2019 | |
| WO | 2019071207 A1 | 4/2019 | |
| WO | 2019211050 A1 | 11/2019 | |
| WO | 2020007511 A1 | 1/2020 | |
| WO | 2020008073 A2 | 1/2020 | |
| WO | 2020008074 A1 | 1/2020 | |
| WO | 2020035362 A1 | 2/2020 | |
| WO | 2020114647 A1 | 6/2020 | |
| WO | 2021032837 A1 | 2/2021 | |
| WO | 2021032873 A1 | 2/2021 | |

OTHER PUBLICATIONS

International Search Report and Written Opinion received for PCT Patent Application No. PCT/EP2019/076647, mailed on Jan. 9, 2020.

European Search Report received for EP Patent Application No. 17195273.2, Extended European Search Report mailed Jan. 11, 2018.

International Search Report and Written Opinion received for PCT Patent Application No. PCT/US2018/054717, Mailed on Dec. 20, 2018.

International Search Report and Written Opinion received for PCT Patent Application No. PCT/US2018/054724, mailed on Feb. 26, 2019.

International Search Report and Written Opinion received for PCT Patent Application No. PCT/US2019/057812, mailed on Feb. 3, 2020.

International Search Report and Written Opinion received for PCT Patent Application No. PCT/EP2019/057811, mailed on Sep. 4, 2019.

International Search Report and written opinion received in PCT Patent Application No. PCT/EP2021/067927, mailed on Dec. 6, 2021.

International Search Report and written opinion received in PCT Patent Application No. PCT/EP2021/067926, mailed on Dec. 7, 2021.

Cansu et al, "Atmospheric Pressure Plasma Jet Treatment of Human Hair Fibers", Journal of Bio- and Tribo-Corrosion, vol. 1:7, No. 1, Feb. 4, 2015.

Zheng et al, "Adhesion of aqueous polyurethane adhesive to human hair", International Journal of Adhesion and Adhesives, Elsevier, Amsterdam, NL, vol. 48, Sep. 30, 2013, pp. 14-19.

Shima et al, "The effect of nitrogen plasma on the skin and hair follicles : a possible promising future for the treatment of alopecia", Archives of Dermatological Research, Springer Berlin Heidelberg, Berlin/Heidelberg, vol. 312, No. 5, Dec. 6, 2019 , pp. 361-371.

Shao et al.: "Surface Treatment of Wool to Achieve Hydrophilic Fibre and the Effect on Subsequent Dyeing and Protease Treatment", Advanced Materials Research; ISSN 1662-8985; Eco-Dyeing, Finishing and Green Chemistry : Selected, Peer Reviewed Papers From The 2011 International Conference on Eco-Dyeing, Finishing and Green Chemistry (EDFGC 2011), Jun. 8-12, 2011, Hangzhou, China, vol. 441, Jan. 1, 2012 (Jan. 1, 2012), pp. 249-254.

International Search Report and written opinion received in PCT Patent Application No. PCT/EP2021/067928, mailed on Dec. 22, 2021.

International Search Report and written opinion received in PCT Patent Application No. PCT/EP2021/067925, mailed on Nov. 22, 2021.

International Search Report and Written Opinion received for PCT Patent Application No. PCT/EP2019/057813, mailed on Jul. 11, 2019.

International Search Report and written opinion received in PCT Patent Application No. PCT/EP2021/067924, mailed on Nov. 26, 2021.

Campiglio Chiara Emma et al., "Coss-Linking Strategies for Electrospun Gelatin Scaffolds", Materials, vol. 1, No. 15, Aug. 4, 2019.

International Search Report and written opinion received in PCT Patent Application No. PCT/EP2021/057812, mailed on Jun. 15, 2021.

* cited by examiner

METHOD FOR COATING KERATIN FIBERS

PRIORITY

This application claims the benefit of priority from U.S. provisional patent application Ser. No. 63/046,110 filed Jun. 30, 2020.

BACKGROUND

Changing the shape and color of keratinous material, especially human hair, is an important area of modern cosmetics. To change the hair color, the expert knows various coloring systems depending on the coloring requirements. Oxidation dyes are usually used for permanent, intensive dyeing's with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing's obtained with direct dyes have a shorter shelf life and quicker wash ability. Dyeing with direct dyes usually remain on the hair for a period of between about 5 and about 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyeing's, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes. A prerequisite for a particularly long-lasting coloration on the hair is, on the one hand, good wash fastness, i.e., the film produced on the hair should not wash off because of treatments with aqueous surfactant solutions such as those used in common shampooing.

Apart from shampooing, however, hair is also subject to other stresses in the daily routine, such as the mechanical stress that occurs, for example, when combing, brushing, and styling. A coloring that is in the form of a colored film on the outside of each hair fiber is quite sensitive to the bending, traction and friction of the hair that occurs during combing.

If adhesion is poor or too brittle, the colored film may flake off the hair fiber. In this case, after combing or brushing, the user perceives a reduced color intensity, an irregularity in the coloring and, in the worst case, a mottled color result.

Keratin fibers may suffer attack of diverse origins, for instance mechanical attack (disentangling or brushing), or chemical attack (dyeing or permanent waving). This attack has an impact on the qualities of the fiber and will lead to difficult disentangling at the time of washing the hair, and to a non-smooth, dry and uneven surface when the hair is dry. The hair is difficult to style and lacks softness.

The conditioning compositions that are currently proposed comprise essentially cationic surfactants, fatty substances, silicones and cationic polymers. They make it possible to facilitate disentangling by softening the keratin fiber and provide sheen, softness, and uniformity to dried hair. However, these effects do not withstand shampooing, and the application of these compositions is essential at each washing step in order to treat and facilitate the disentangling of the hair.

Moreover, it has been found that consumers are increasingly in search of care compositions that are not only capable of appropriately conditioning the hair, but also capable of affording satisfactory styling effects.

Therefore, a need exists to have available more effective color compositions and conditioning and styling compositions.

SUMMARY

These and other design features of aspects of the present invention include but not limited to coatings on keratin fibers/keratinous surfaces, compositions and their components, parameters associated with methods for applying the compositions to keratin fibers/keratinous surfaces and parameters associated with formation of coatings on keratin fibers/keratinous surfaces produced by the methods using the compositions. These aspects additionally include qualities of the coatings that deliver long lasting characteristics as well as styling, hair setting, hair conditioning and a method for intentionally removal for coatings on keratin fibers/keratinous surfaces. The coatings may optionally include pigment particles which produce colored coatings and color compositions from the compositions and coatings according to the invention.

Embodiments of the coatings are directed to polymeric films on keratin fibers/keratinous surfaces (hereinafter keratin fibers), preferably human scalp hair. The polymeric films may comprise one, two, three or four polymeric layers overlaid on the keratin fibers. The coatings, also known as polymeric films on keratin fibers, display a set of physical and chemical properties that characterize the coatings irrespective of the kind or kinds of polymers forming the coatings. When pigments are included the physical and chemical properties of the coatings irrespective also of the pigment particles forming the color coatings. These characteristics may be established by the coating properties including but not limited to remanence, wash-fastness, resistance to environmental attack, elastomeric flexibility to enable free movement of the coated keratin fibers, tensile strength to resist flaking and breakage. For color coatings, the characteristics include optional color mimicking of appropriate shades for roots, mid-length and tips of keratin fibers. For clear coatings, the characteristics include shaping, conditioning and style holding and endurance in response to environmental factors as well as an optional ready removal by ordinary shampoo techniques. These characteristics preferably may be demonstrated by tests of the coatings in hair swatches prepared from natural, unbleached natural white human hair and bleached natural white human hair.

Embodiments of the compositions of present invention are also directed to a group of reactive-polymer film forming compositions that may be dressed onto the surfaces of keratin fibers (e.g., human scalp hair) to form coatings on these surfaces. The techniques for dressing are accomplished at rates and timing that enable ready segmental coating of roots, mid-lengths and tips of keratin fibers and avoid and/or minimize dripping, clumping, lumping, balling and/or avoid flow and spread issues of the process for applying the film forming compositions to the fiber surfaces. Embodiments of the present invention are further directed to pre-treatment compositions for use with the compositions according to the invention. The pre-treatment compositions may be dressed onto the keratin fiber surfaces before dressing with the film forming compositions. For the color versions of the compositions, the pre-treatment compositions as well as the film forming compositions may contain mixtures and blends of pigment microparticles with dispersant and optional components for facilitating pigment microparticle combination with one or more of the pre-treatment and film forming compositions.

The pre-treatment compositions and film forming compositions also may optionally include any one or more of a number of additives herein described as a group characterized as the additive composition. The additive composition is not a separate composition for addition to keratin fibers. Instead, one or more of the constituents of the additive composition may be combined with any one or more of the pretreatment composition and/or the film forming compositions. The additives provide certain beneficial qualities to any one or more of these compositions. Such qualities include but are not limited to UV and sunlight resistance, resistance to triplet formation, sebum resistance, hair style setting and the like. According to the invention, the dressing of the keratin fibers with the pre-treatment and film forming compositions as well produces multiple layer coatings on keratin fibers that display significant remanence, maximum wash-fastness (color wash-fastness when pigments are present), shine, shine retentions, smoothness, softness, silkiness, hair feel, resistance to removal by sebum, UV, rubbing, shampoo, hair dryer blowing, wind, flaking, cracking while at the same time enabling trigger techniques for ready removal not associated with any of these assailing factors.

Embodiments of film forming compositions according to the invention may comprise reactive-polymer film forming compositions. In addition to optional dispersed pigment particles, the reactive-polymer film forming compositions may comprise at least two reactive-polymer components having complementary reactive groups that covalently combine in situ to form longer polymer chains and cross-linked individual chains. The reactive-polymer components may comprise organic reactive-polymers, silicone reactive-polymers, organosilicone reactive-polymers and/or condensable silanes of 1 to 20 or more silicons bearing hydroxyl and/or alkoxy groups. The reactive-polymer components may be polymers, oligomers and/or non-polymeric molecules. As non-polymeric molecules, the reactive polymers may be unitary, dimer, trimer, tetramer and similar units such as monomeric units that combine to form extended oligomeric and/or polymeric chains. The reactive polymers may have non-polymeric molecular weight average molecular weights and/or as multiple monomeric units and/or oligomer and polymer low range Mw's such as from about 100 Da and when combined in situ to form longer chain cross linked polymers, the in situ formed polymers may have Mw's of at least 2 KDa up to a high MDa range for the extended chains to an almost infinite Mw for network cross linked in situ formed polymers. The cross linked in situ formed polymers may have at least one internal chain and/or one chain terminal cross link per at least 100 monomeric residues, preferably at least 50 monomeric residues, more preferably at least about 10 monomeric residues, most preferably at least about 1 to 3 monomeric residues. Exemplary cross links may extend the reactive polymers/oligomers/small molecule reactants multiple times to provide polymeric chains of at least 2 KDa and may internally cross link such extended polymeric chains by at least one and preferably at least 2, 3 or 4 internal links so as to form network and/or star configurations of the crosslinked polymeric product.

The complementary reactive groups are capable of forming covalent bonds to join reactive-polymer molecules to extend their chains and to cross-link to form nets, stars, branches and all forms of inter-linked molecules. The complementary reactive groups are suitable for covalent bonding in a biological environment. The heat, rate of reaction, side effects and reaction by-products are controlled so as to be amenable with biological tissues. Embodiments of the complementary reactive groups include: a) hydroxysilyl and alkoxysilyl; b) amine and/or mercaptan and $\alpha,\beta$ unsaturated acyloxy groups such as but not limited to (meth)acryloxy and crotonyloxy; and c) carbodiimide and carboxyl or amine.

Embodiments of the pre-treatment and film forming compositions are formulated in media, with optional additional components, and at concentrations that enable facile dressing onto the keratin fiber surfaces and effective film formation by drying and/or curing. The pre-treatment and film forming compositions are formulated to be liquids with appropriate surface free energy, surface tension and contact angle relative to the surfaces to which they are dressed to enable complete spreading but with viscosities to minimize or avoid run-off and/or dripping. The drying and curing rates of the pre-treatment and color compositions following their dressing onto keratin surfaces are appropriate for promotion of efficient unhurried treatment and applications. The dried and cured films formed from the pre-treatment and film forming compositions display at least some of the following properties elastomeric, entanglement, Mw's, hydrogen bonding, polar/dipolar and lipophilic interactions and cross-linking densities that promote adhesion, remanence, resistance toward sebum, shampooing, wind, brushing, rubbing and unacceptable degradation.

Embodiments of the pre-treatment and/or film forming compositions may include any one or more of the constituents of the additive composition including but not limited to plasticizers. dispersants, synthetic and/or natural clays, synthetic and/or natural microfibers and function agents designed to contribute to the elasticity, remanence, maximum color wash-fastness, shine, shine retentions, smoothness, softness, silkiness, hair feel as well as to contribute to resistance to removal and/or coating damage by sebum, UV, rubbing, shampoo, hair dryer blowing, wind, flaking, cracking of the film coatings on keratin fibers. Plasticizers for organic, silicone and organosilicon polymers may be added to the pre-treatment and/or film forming compositions to increase elasticity, film integrity and interlayer compatibility. Dispersants including emulsifiers, surfactants and suspension agents may be added to the pre-treatment and/or film forming compositions to positively affect uniform, substantially permanent dispersions of dis-similar substances and solid particles therein. Clays and microfibers may be added to the pretreatment and/or film forming compositions to strengthen film integrity add smoothness to the tactile sensation of the dried/cured film coatings and enable elongation and stretching without film breakage or flaking.

Embodiments of the film forming compositions may be dressed as a coating on the keratin fibers already coated with films formed from the pre-treatment compositions according to the foregoing aspects of the invention. The film forming compositions may comprise a combination of the first and second components of the reactive polymer composition. The first and second components present in the film forming composition have reactive functional groups that are complementary. The complementary pair in situ reaction enables covalent bonding of the film forming composition components and the pre-treatment composition components through this complementary reactive pair. The covalent bonding provides covalent bond adherence between the film forming coat and pretreatment coat dried and cured on the keratin fibers. These film coatings function as color coatings with pigments and as hair setting and hair styling coatings without pigment (e.g., clear coatings). Additives as described above may be included to provide hair conditioning and to enable ready removal of the color coat and clear coat films.

An additional aspect of the invention is directed to the optional priming and deep cleaning of the keratin fibers to enable long lasting coatings on the fibers, especially anagenic hair. Praeparatur and Fundamenta techniques in combination with the small molecule pretreatment network coupled with the self-crosslinkable binder establish and preserve long lasting remanence for coatings on keratin fibers whereas without application of the Praeparatur and/or Fundamenta techniques the coatings demonstrate significant to almost full removal during the multiple shampoo applications. Use or avoidance of the Praeparatur and Fundamenta techniques for priming and deep cleaning the keratin fibers accordingly constitutes a method by which the coating may be rendered easily removable or rendered long lived. An ancillary for ready removal is the use of a precoating on the keratin fibers of a natural oil, long chain fatty acid, the corresponding methyl or ethyl ester and/or silicone oil before application of the pretreatment and film forming compositions.

Definitions

Unless defined otherwise, all technical and scientific terms used herein have the same meaning as commonly understood by a person of ordinary skill in the art.

As used in the specification and the appended statements, the singular forms "a," "an" and "the" include plural referents unless the context clearly dictates otherwise The term "may" in the context of this application means "is permitted to" or "is able to" and is a synonym for the term "can." The term "may" as used herein does not mean possibility or chance.

The term and/or in the context of this application means one or the other or both. For example, an aqueous solution of A and/or B means an aqueous solution of A alone, an aqueous solution of B alone and an aqueous solution of a combination of A and B.

The molecular weight of a polymer or oligomer used according to the invention may be measured by a weight average molecular weight, and the distribution of molecules of different molecular weights of a polymer used according to the invention is determined by its polydispersity. Molecular weight is expressed as daltons (Da), kiloDaltons (KDa) and megaDaltons, which is million daltons or (MDa). The acronym $M_w$ stands for weight average molecular weight, $M_n$ is the number average molecular weight of a given polymer. Polydispersity is a unit-less number and indicates the breadth of the distribution of the polymer molecular weights and is defined as the $M_w/M_n$.

The term "about" is understood to mean±10 percent of the recited number, numbers or range of numbers.

The term "about 0 wt %" is understood to mean that no substance, compound or material to which zero (0) refers is present, up to a negligible but detectable amount is present, assuming that the detectability can be determined on a parts per million basis.

Where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being ethyl and X being propyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

Keratin fibers means any natural material containing keratin protein including hair, eye brows and eyelashes. Natural keratin fibers include those from mammals and/or on mammals including human, primate, ruminant, camelid, equine, rodent and neovison including but not limited to cow, sheep, deer, goat, buffalo, lama, alpaca, camel, guanaco, vicuna, horse, antelope, moose, elk, rat, mouse, beaver, rabbit, mink, monkey, ape and similar species. Natural keratin material may include hair and fur. Keratin fibers include scalp hair, eyebrow hair and eyelash hair. Keratin fibers may be removed from their source such as hair cut from the scalp of a living person or may mimic anagenic hair when treated with sebum. As used herein keratin fibers includes cut hair and anagenic hair. For experimental purposes, keratin fibers are formed into tresses. A tress is a shock of keratin fibers e.g., hair, held in a clamp at one end and free at the other end. The head of the average person weighs about 100 g. A tress is formed with about 1 gram of hair or about 1/100 the weight of the hair on the head of a person. Typical commercial hair products for application to hair weigh about 100 to 120 g which translates into about 1 g of product per gram of a person's hair. This relationship establishes the amount of experimental product to be applied to a tress of hair, 1 gm of experimental product per tress weighing about 1 g.

As used herein "anagenic hair" means hair strands that are in direct connection with a hair follicle which is in either the anagen or telogen state. Anagenic hair is present in one of these states on a scalp of a person, a human. The follicle of anagenic hair produces long chain fatty acids, so-called F-layer, which form a water resistant coating on the cuticle of the hair shaft. Joining the hair follicle channel is a sebaceous gland that secretes sebum onto the hair shaft and onto the scalp. As a strand of hair grows from the follicle and extends from the scalp, sebum produced at the follicle spreads out from the follicle and continues to coat the strand. Sebum is removed at least in part from strand ends by shampooing but is replenished by this continued production. Hair cut from a living person is no longer anagenic hair.

As used herein, the terms "covalent, coordinate, electrostatic, ionic, dipolar and entanglement or entwining interactions" mean a chemical relationship between two atoms or two groups of atoms. The interaction includes a covalent bond between the atoms such as the covalent bond between the two carbons of ethane. The interaction includes a coordinate bond between two or more atoms such as the coordinate bond between oxygen and sulfur of the sulfate anion ($SO_4^{-2}$) or a complex of zinc and EDTA. The interaction includes an electrostatic or ionic interaction between two charged atoms or particles such as the interaction between sodium and chloride of salt or between ammonium and acetate of ammonium acetate. Dipolar interaction includes hydrogen bonding such as the interaction between water and the hydroxyl of methyl alcohol. The interaction includes entanglement or entwining which is lipophilic interaction or mechanical/physical twisting together such as is present in the molecules of polyethylene.

Adherence as used herein generally refers to an arrangement in which a substance formed of a polymer, oligomer or small molecule exhibits a connective aspect with another material such as another polymer, oligomer, small molecule, keratin protein, through such forces as covalent bonding, hydrogen bonding, coordinate interaction, electrostatic interaction, dipolar interaction, small force interaction, dispersion force at least as a result of entropy, molecular entanglement, mechanical interaction as may be exhibited on a molecular level by a molecular chain wrapping around irregular terrain features of a surface. Adherence in this context may be, but not necessarily, shown by the inability of the adhered material to be removed from the substance without exertion of any force.

Entanglement as used herein generally refers to an arrangement in which a chain crosses an arbitrary plane 3 times. The chain is then entangled. If the chain is shorter and crossed only two times, it can be pulled in the middle and both ends will release without being bound. With three crossings, if the chain is at one point, it will trap another polymer chain at a different place.

As used herein, the term "transfer resistance" or rub off resistance generally refers to the quality exhibited by colored coatings that are not readily removed by contact with another material, such as, for example, an item of clothing or the skin. Transfer resistance can be evaluated by any method known in the art for evaluating such transfer. For example, transfer resistance of a colored coating can be evaluated by the amount transferred from a wearer to any other substrate after the expiration of a certain amount of time following application of the colored coating to the hair. The amount of colored coating transferred to the substrate can then be evaluated and compared. For example, a colored coating can be transfer resistant if a majority is left on the wearer's hair. Preferably little or no colored coating is transferred to the substrate from the hair.

As used herein, the term "minimally alters the keratin fibers, upon application" generally means that after removal of the composition coating on the keratin fibers, the keratin fibers are returned to a substantially unaltered state. The state of the keratin fibers can be assessed for example using ATR FT-TR for oxidative damage as described later or through tensile testing methods known to those skilled in the art for assessing fiber strength for example using equipment such as those designed and sold by Dia-Stron™.

As used herein, the term "converting" means causing covalently co-reactive pairs of components of a composition such as but not limited to the binder and linker of the film forming composition to react together chemically to produce the reacted form such as, for example a chain-extended and/or cross linked polymer functioning as coating or film. Converting is accomplished by the application of an activity designed to cause the covalent bonding of the reactive groups or pairs of the co-reactive components. Activities enabling conversion include but are not limited to one or more of drying, heating, curing as in causing the curing/reacting together the co-reactive components, allowing the co-reactive components to combine or mix at standard conditions without further intervention, addition of a catalyst, changing pH of the composition and any other activity that is capable of influencing the reactivity and/or rate of the reaction of the co-reactive components.

"Aliphatic substituent, group or component" refers to any organic group that is non-aromatic. Included are acyclic and cyclic organic compounds composed of carbon, hydrogen and optionally of oxygen, nitrogen, sulfur and other heteroatoms. This term encompasses all of the following organic groups except the following defined aromatic and heteroaromatic groups. Examples of such groups include but are not limited to alkyl, alkenyl, alkynyl, corresponding groups with heteroatoms, cyclic analogs, heterocyclic analogs, branched, dendritic, star or fullerene-like and linear versions and such groups optionally substituted with functional groups, as these groups and others meeting this definition of "aliphatic" are defined below.

"Aromatic substituent, group or component" refers to any and all aromatic groups including but not limited to aryl, aralkyl, heteroalkylaryl, heteroalkylheteroaryl and heteroaryl groups. The term "aromatic" is general in that it encompasses all compounds containing aryl groups optionally substituted with functional groups (all carbon aromatic groups) and all compounds containing heteroaryl groups optionally substituted with functional groups (carbon-heteroatom aromatic groups), as these groups and others meeting this definition of "aromatic" are defined below.

As used herein, the term "optionally" means that the corresponding substituent or thing may or may not be present. It includes both possibilities.

"Alkyl" refers to a straight or branched, dendritic, star or fullerene-like or cyclic hydrocarbon chain group consisting solely of carbon and hydrogen atoms, unless otherwise specifically described as having additional heteroatoms or heterogroups. The alkyl group contains no unsaturation, having from one to twenty four carbon atoms (e.g., $C_1$-$C_{24}$ alkyl). Whenever it appears herein, a numerical range such as for example but not limited to "1 to 24" refers to each integer in the given range; e.g., "1 to 24 carbon atoms" means that the alkyl group may consist of 1 carbon atom, 2 carbon atoms, 3 carbon atoms, etc., up to and including 24 carbon atoms, although the present definition also covers the occurrence of the term "alkyl" where no numerical range is designated. In some embodiments, it is a $C_1$-$C_4$ alkyl group. In other instances, it is a $C_1$-$C_6$ alkyl group and in still other instances it is a $C_1$-$C_{24}$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

Alkylenyl" refers to a straight or branched, dendritic or star divalent hydrocarbon chain consisting solely of carbon and hydrogen atoms, unless otherwise specifically described as having additional heteroatoms or heterogroups. The alkylenyl group contains no unsaturation, has a dangling valence bond at either end of the chain for bonding to two other moieties. The alkylenyl group may have a carbon number range of 1 to 24 carbon atoms unless otherwise specified. In all cases the general and specific numerical range of carbon atoms includes each integer in the range. An example of a divalent hydrocarbon chain designated as an alkylenyl group is as follows: —$CH_2$—$CH_2$—$CH_2$—$CH_2$—; the dashes (—) indicate valence bonds to other atoms or moieties not shown. This example of an alkylenyl group is butylenyl.

"Cycloalkyl" is a subcategory of "alkyl" and refers to a monocyclic or polycyclic group that contains only carbon and hydrogen, and may be saturated, or partially unsaturated. Cycloalkyl includes one or more rings, such as two or three or four rings either linked in tandem or through alkyl group or fused. Cycloalkyl groups include groups having from 3 to 24 ring atoms (i.e., $C_3$-$C_{24}$ cycloalkyl). Whenever it appears herein, a numerical range such as but not limited to "3 to 24" refers to each integer in the given range; e.g., "3 to 24 carbon atoms" means that the cycloalkyl group may consist of 3 carbon atoms, etc., up to and including 24 carbon atoms. In some embodiments, it is a $C_3$-$C_8$ cycloalkyl group. In some embodiments, it is a $C_3$-$C_5$ cycloalkyl group. Pursuant to the definition of alkylenyl, a cycloalkenyl group is a monocyclic or polycyclic group with two dangling valences for bonding to two other moieties. Illustrative examples of cycloalkyl groups include but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

"Alkoxy" refers to the group —O-alkyl, including from 1 to 24 carbon atoms of a straight, branched, dendritic, star or cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, alkyl is an alkyl group which encompasses both linear, branched, dendritic, star or fullerene-like chain alkyls of multiple carbon atoms. Without further definition of the number or carbon atoms present, as used herein, the term "alkoxy" such as an alkoxysilyl group means a $C_1$-C6, preferably $C_1$-$C_4$, more preferably $C_1$-$C_2$ alkoxy such as methoxy and ethoxy.

The term "alkoxysilyl" refers to a silicon atom substituted by three alkoxy groups, in other words a trialkoxysilyl group, and in which the silicon atom joins either a carbon or an oxygen depending upon the identity of the moiety to which the alkoxysilyl group is bound, such as but not limited to an organic compound, a siloxane compound, an organosiloxane compound, an organic polymer backbone, a silicone polymer backbone or an organosilicone backbone. Thus, the term "alkoxysilyl" as used herein is a synonym and means a trialkoxysilyl group, in other words —$Si(OR)_3$ in which R is an alkyl group of 1 to 6 carbons, preferably 1 to 3 carbons and more preferably methyl or ethyl. Also, because the hydrolysis intermediate of each alkoxy of the alkoxysilyl group is hydroxy group as in hydroxysilyl, the hydroxysilyl group is included in this definition. One of the alkoxys of the alkoxysilyl group may hydrolyze and the resulting hydroxysilyl may condense with another hydroxysilyl group derived from the corresponding alkoxysilyl group to form an Si—O—Si bond. Because there are three alkoxy groups on this moiety, the formation of a silicon-oxygen-silicon bond may occur as many as three times for a single alkoxysilyl (trialkoxysilyl) group. Irrespective of whether the alkoxysilyl group is pendant or terminal on a molecule such as a small molecule, oligomer or polymer, this multiple Si—O—Si bonding arrangement for a single alkoxysilyl group means that the molecule with the single alkoxysilyl group may undergo multiple condensations. The molecule with an alkoxysilyl may be chain extended with another molecule with an alkoxysilyl to produce a linear chain extended molecule. This linear chain extended molecule contains additional Si—OR functions at this Si—O—Si chain extension. These additional Si—OR functions can again condense with a corresponding Si—OR function of another linear chain extended molecule. The result is a cross-link at the intermediate section of these molecules bearing the Si—O—Si link. These additional Si—OR's of separate chain extended molecules can therefor condense to cross link the separate chain extended molecules.

"Amino" or "amine" refers to an —$N(R^a)_2$ group, where each $R^a$ is independently hydrogen or an alkyl group of 1 to 3 carbons, eg, methyl, ethyl or propyl.

"Aryl" and its synonym aromatic refer to a conjugated pi ring or multiple rings with six to twenty two ring atoms. The aryl group has at least one ring having a conjugated pi electron system which is carbocyclic (e.g., phenyl, fluorenyl, naphthyl and anthracenyl). Included are partially saturated aryl rings such as tetrahydro naphthyl.

"Heteroalkyl" "heteroalkenyl" and "heteroalkynyl" include optionally substituted alkyl, alkenyl and alkynyl groups and which have one or more skeletal chain atoms selected from an atom other than carbon, e.g., oxygen, nitrogen, sulfur, phosphorus or combinations thereof. A numerical range may be given, e.g. $C_1$-$C_{24}$ heteroalkyl which refers to the chain length in total, which in this example may be as long as 24 atoms long. For example, a —$CH_2OCH_2CH_3$ group is referred to as a "$C_4$" heteroalkyl, which includes the heteroatom center in the atom chain length description. Connection to the rest of the molecule may be through either a heteroatom or a carbon in the heteroalkyl chain.

"Heteroaryl" or heteroaromatic refers to a 5, 6 or 10-membered aromatic group (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system or a conjugated ring system such as cyclopentadienyl optionally with a bridging atom providing conjugation such as pyrrole or ferrocenyl. Whenever it appears herein, a numerical range refers to each integer in the given range. An N-containing "heteroaromatic" or "heteroaryl" moiety refers to an aromatic group in which at least one of the skeletal atoms of the ring is a nitrogen atom. The polycyclic heteroaryl group may be monocyclic or non-monocyclic. The heteroatom(s) in the heteroaryl group is optionally oxidized. One or more nitrogen atoms, if present, are optionally quaternized. The heteroaryl is attached to the rest of the molecule through any atom of the ring(s). Examples of heteroaryls include, but are not limited to pyrrolyl, furanyl, thiophenyl, imidazolyl, pyranyl, pyridinyl, pyrimidinyl, benzimidazole, benzothiophenyl, quinolinyl, quinazolinyl, and similar heteroaryl compounds of 6 to 12 carbons and 1, 2 or 3 heteroatoms including any combination of nitrogen, oxygen and sulfur.

"Heterocyclic" refers to any monocyclic or polycyclic moiety comprising at least one heteroatom selected from nitrogen, oxygen and sulfur. As used herein, heterocyclyl moieties can be a partially saturated aromatic ring or a saturated monocyclic or polycyclic ring wherein the ring may be formed of 3 to 8 atoms.

The term "polymer" or "Poly" means any or more of an organic, silicone or organosilicone compound formed from multiple monomeric units. The units may be identical or may be a combination of units of differing identities. The number of units present may range from at least 2 to compounds having very large number of units. Typical weight average molecular weights of a polymer may range from less than one hundred Da to a million or more Da.

Compounds and groups including a polymer, an alkyl, an alkylenyl, a carbon or silicone chain, a carbon or silicon backbone, an aliphatic group of multiple carbons, hetero forms of any of the foregoing compounds and groups, as well as groups including aromatic, heteroaromatic cycloalkyl heterocycloalkyl or hetero forms thereof bearing any of these foregoing compounds and groups may have a structural configuration of linear, branched, star, dendritic or fullerene. A preferred configuration is branched or linear and a more preferred configuration is linear. Use of any of these terms without indicating a particular configuration incorporates all of these configurations and means that linear and/or branched is preferred and linear is most preferred.

The terms "In situ linking" and "in situ linkable" and "Cross linkable" mean the potential at a future time to form covalent bonds to provide interactions and/or connections between molecules. The terms "in situ linked" and "cross linked" mean that in the present state, covalent bonds have already occurred.

"in situ" is a Latin phase meaning in its original place. In the context of this invention, it means an activity such a cross linking that takes place on the hair.

The average reactive functional group equivalent weight as used herein means for a reactive functional group of a complementary pair, the ratio of the weight average molecular weight of the polymer, oligomer or small molecule containing the reactive functional group to the average number of occurrences of that reactive functional group in the polymer, oligomer or small molecule. If the Mw of a polymer is 1 KDa and the average number of occurrences of the reactive functional group in the polymer is 2, the Mw for the reactive functional group equivalent weight is (1 KDa)/2 or 500 Da.

Coefficient of thermal expansion refers to the fractional increase in length of a species per Celsius increase in temperature at a constant pressure with a starting temperature of 25° C.

Zeta potential relating to pigment microparticles means the electrokinetic potential of extremely small particles suspended in colloidal dispersions. It is caused by the net electrical charge at the particle interface with the suspending fluid. It is an indicator of the stability of a colloidal dispersion. The magnitude indicates the degree of electrostatic repulsion between adjacent similar charged particles in a dispersion. At zero or minimal + or − potential, rapid coagulation can occur. At a + or − zeta potential above about 40 mV, good colloidal stability is maintained. Zeta potential can be measured using approaches known to those skilled in the art. For example a Zetasizer Nano Z from Malvern Panalytical Ltd, Malvern U.K. may be used to assess the zeta potential of the components.

Microfibril length as used herein general refers to a distribution of lengths for any given microfibril, and the fiber length refers to the average fiber length, assessed over a minimum of 10 fibers chosen randomly from a sample of the microfibrils. The length refers to the end to end distance along the major axis of the material and is not a measure of the cross sectional width.

Hansen Solubility Parameters constitute a technique for characterizing solubility, dispersion, diffusion, chromatography and related topics for a particular material. The material such as a solvent or solute can be characterized by three parameters δD for Dispersion (van der Waals), δP for Polarity (related to dipole moment) and δH for hydrogen bonding. See "Hansen Solubility Parameters—A User's Handbook", CRC Press, Boca Raton, 2007, ISBN-10: 0849372488.

Hydrogen bonding refers to a weak bond between two molecules resulting from an electrostatic attraction between a proton in one molecule and an electronegative atom in the other. Ionic bonding refers to a type of chemical bonding that involves the electrostatic attraction between oppositely charged ions.

Young's modulus, or the Young modulus, is a mechanical property that measures the stiffness (e.g., stretchiness) of a solid material. It defines the relationship between stress (force per unit area) and strain (proportional deformation) in a material in the linear Hookean elastic regime of a uniaxial deformation. In other words, the ability of a material to withstand changes in length when under lengthwise tension or compression.

The term Tg or glass transition temperature refers to the temperature range through which a material, such as but not limited to a polymer, transitions from amorphous solid-like or glass-like properties at a lower temperature to viscous or rubber-like properties at a higher temperature. The transition is not a phase transition such as solid to liquid. Embodiments of the color coatings on mimic hair, treated hair and untreated hair typically will exhibit a Tg range well below ambient temperature so that the films produced will exhibit flexible, elastomeric, smooth physical properties.

The term ultimate compression refers to the amount of compression a given material can experience under a specific test method before failure occurs and the material breaks.

A nanoemulsion is a liquid/liquid, liquid/solid, liquid/gas or gas/gas composition in which there is at least one discontinuous phase dispersed in a continuous phase and in which the average particle or micellar diameter of the discontinuous phase is in the range 10 nm-300 nm.

The term "sebum" is an oily, waxy substance produced by the sebaceous glands of the human body. It coats, moisturizes, and protects skin and hair. Sebum is primarily composed of triglycerides (≈41%), wax esters (≈26%), squalene (≈12%), and free fatty acids (≈16%). The sebum used to form mimic hair is Hautfett nach BEY, sold by Wfk-Testgewebe GmbH which comprises 18.0% free fatty acids, 32.8% beef tallow, 3.6% triglycerides, 18.3% wool fat, 3.7% cholesterol, 12.0% hydrocarbons, 11.6% cutina.

The terms "priming" and "deep cleaning" refer to the substantial to essentially complete removal of sebum and F-layer substances from the surfaces of anagenic hair and also refer to removal of synthetic sebum coated onto mimic hair tresses. The Praeparatur and Fundamenta techniques accomplish the priming and deep cleaning of keratin fiber surfaces. Practice of these priming and deep cleaning techniques may accomplish adjustment of the keratin fiber surfaces so as to expose variable surface topography and gain an intimate interaction with agents small enough to access the variations of the topography.

DETAILED DESCRIPTION

The present invention is directed to development of coatings on keratin fibers that contribute to, enhance and promote qualities of the coatings so that the coated keratin fibers demonstrate a performance similar to the performance of young, uncoated, vibrant, attractive keratin fibers preferably of the scalp. To accomplish this aspect, the coatings exhibit qualities including but not limited to flex, stretch and bend, integrity of continuous film under flex, stretch and bend conditions, wash-fastness, remanence, and resistance to degradation and damage caused at least by, but not limited to, UV radiation, sebum, shampoo, sweat, rain, wind and/or environmental attack and coating surface qualities including but not limited to non-stickiness, minimal bulk, free hair strand movement, tactile sensation similar to untreated, unbleached human hair, and aural sensation known as the squeak sensation.

The development and preservation of these qualities may be accomplished by one or more combinations of polymer films formed from one or more of reactive-polymer film forming compositions and pre-treatment compositions. The coatings and the pretreatment and film forming compositions forming them also preferably include triggers for coating removal.

Embodiments of the color coating compositions according to the invention comprise the pre-treatment composition and the reactive-polymer film forming composition, the composition properties, the dispersant composition for optional pigment inclusion, the additives composition and the removal composition. One or both of the pre-treatment, preformed polymer, reactive-polymer film forming composition may optionally contain pigment particles. Any of the compositions containing pigment will also contain a dispersant composition. While one of the film forming composition embodiments may be dressed alone onto keratin fibers, it is preferred to dress the keratin fibers first with the pre-treatment composition followed by the reactive-polymer film forming composition. The pre-treatment composition incorporates a base compound comprising an organic, silicone and/or organosilicone small molecule. The base compound of the pre-treatment composition develops non-covalent bonding to the keratin fibers. The base compound of pre-treatment composition also provides a coating layer promoting adherence of the reactive-polymer film forming composition onto the keratin fibers. The adherence is at least in part responsible for the tensile strength, film to fiber connection and remanence of the coating on keratin fibers.

The reactive-polymer film forming composition may also optionally comprise materials and substances that contribute to the elastomeric, tensile strength, flex and bend durability and wear resistance of the color coating on keratin fibers. These materials and substances include but are not limited to plasticizers, dispersants, synthetic and/or natural clays, synthetic and/or natural microfibers and any combination thereof. The plasticizers and dispersants enable polymer molecules and chains to "slip" past each other under stress conditions resulting from stretching, elongation and compression. The "slip" factor contributes at least in part to the elastomeric quality of the color coating on keratin fibers. The plasticizers and dispersants are compatible with the polymers and are well-known materials for such purpose. They are described in detail in a separate section below.

The optional use of synthetic and/or natural clays and microfibers with the film forming compositions may contribute at least in part to the tensile strength, wear resistance and remanence of the coating on keratin fibers. The clays and microfibers are known for their contribution to protective and wear attributes of coatings in the industrial substrate coatings such as appliance and vehicle coatings. The clays and microfibers enhance smoothness of the coating on keratin fibers and lessen the tendency toward film (coating) breakage or flaking during elongation and stretching. Minor amounts of clays and microfibers provide sufficient enhancement of these features. The natural clays are aluminum phyllosilicates of kaolinite, montmorillonite, smectite, illite and chlorite classes. The natural clays typically are lamellar in form and are intercalated with magnesium, potassium and calcium ions. Natural clays may be modified by exchanging the intercalated ions with organic molecules capable of accepting a charge. Microfibers are ultrafine synthetic fibers formed from polyester and/or polyamide and/or cellulose and/or polyolefin and produced commercially as Ultrasuede, Primaloft, Prolen, Polar fleece and Microfiber. Microfibers are elastic so that when combined in minor amounts with the composition embodiments of the invention, they contribute to the elasticity of the coating on keratin fibers.

Film Forming Composition

The reactive-polymer film forming composition comprises pairs of reactive-polymers having complementary reactive groups (first and second reactive functional groups) that covalently bond in situ to form the polymer film product. The reactive polymer may also have but are not limited to non-reactive groups that may but not necessarily display such functions and hydrogen bonding and dipolar interaction. Embodiments of the polymer product may be chain extended, cross linked and/or a combination of both to form branched, network, star microstructure configurations and combinations thereof. The pairs of reactive-polymers comprise first and second components, each of which may be organic, silicone and/or organosilicone reactive-polymers and/or oligomers. The first component typically is a binder with first functional groups and may include non-reactive in-chain and pendant groups that enable hydrogen, dipolar and ionic interactions. The second component is also known as an in situ linker. The second component may be a small molecule, an oligomer or a polymer with second functional groups. Like the binder, the linker may also include non-reactive in-chain and/or pendant groups that enable hydrogen, dipolar and ionic interactions. The first and second functional groups are complementary reactive groups. Embodiments of the complementary reactive groups for the film forming composition include: a) alkoxysilyl which self-condenses so it does not have a separate in situ linker; b) amine and/or mercaptan and $\alpha,\beta$ unsaturated acyloxy groups such as but not limited to (meth)acryloxy and crotonyloxy; and c) carbodiimide and carboxyl or amine. These complementary reactive groups form convenient separate sections of the following description of the film forming composition These three separate sections are:
  A) The Alkoxysilyl Film Forming Composition,
  B) The Aza Michael Film Forming Composition, and
  C) The Acid CDI Film Forming Composition.

The Alkoxysilyl Film Forming Composition

Embodiments of the alkoxysilyl film forming composition are directed to at least one in situ cross linkable self covalently reactive organic polymeric binder having two or more alkoxysilyl pendant and/or terminal groups, preferably at least terminal alkoxysilyl groups. The binder is preferably linear or branched, more preferably linear. The alkoxysilyl film forming composition further comprises one or more microparticle pigments and/or color bodies. The alkoxysilyl film forming composition also comprises a medium in which the self covalently cross linkable binder, pigment(s) and/or color bodies are dispersed, mixed and/or otherwise contained. The alkoxysilyl film forming composition further comprises a substance that functions as a catalyst in relation to the in situ cross linkable binder. Application of the alkoxysilyl film forming composition to keratin fibers may also include a conversion step such as drying and curing to evaporate residual medium from the alkoxysilyl film forming composition on the surfaces of the keratin fibers and to cause the alkoxysilyl condensation thereby producing a chain extended, crosslinked polymer network comprising a film.

Alkoxysilyl Binder

The alkoxysilyl binder may comprise a polymer or copolymer of ester, amide, urethane, urea, ether and/or olefinic monomeric units or any combination thereof with at least two pendant and/or terminal alkoxysilyl groups, and preferably at least two of the alkoxysilyl groups are terminal groups. The alkoxysilyl binder may be a random or block copolymer and may have a linear or branched, preferably a linear configuration.

In particular, the self-reactive organic alkoxysilyl binder comprises Formula IA

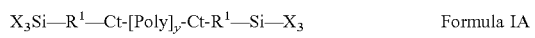

$$X_3Si-R^1-Ct-[Poly]_y-Ct-R^1-Si-X_3 \quad \text{Formula IA}$$

In Formula IA, X may be alkoxy of 1 to 3 carbons, preferably methoxy or ethoxy. The group $R^1$ is a C1 to C8 linear or branched alkylenyl group. The group Ct is a connector group which joins or connects $X_3Si-R^1-$ to Poly.

Group Ct comprises Formula II.

$$-U^1-R^2-U^2- \quad \text{Formula II}$$

For Formula II, $U^1$ and $U^2$ are each independently a urea or urethane group. The group $U^1$ is covalently bonded to $R^1$ and the group $U^2$ is covalently bonded to Poly. The group $R^2$ is a C2 to C12 linear or branched alkylenyl group, a C6-C16 alkylcycloalkyl group which may include one or multiple cycloalkyl rings linked in tandem or linked by alkyl groups, a C6-C12 aromatic group which may include one or multiple aromatic groups or a C6-C14 alkyl aromatic group which may include one or multiple aromatic groups linked in tandem or linked by alkyl groups. Embodiments of the group $R^2$ are derived from common diisocyanates. For example, hexamethylene diisocyanate (1,6-hexane diisocyanate) produces an alkylenyl group. Isophorone diisocyanate produces an alkyl cycloalkyl group. Toluene diisocyanate produces an alkyl aromatic group. Methylene bis(cyclohexane isocyanate) also produces an alkylcycloalkyl group. Methylene diphenylisocyanate produces an alkyl aromatic group. Formula II is produced by combination of an $R^2$-diisocyanate and the corresponding hydroxyl or amine from $X_3SiR^1$-G and G-Poly in which each G independently is an amine or hydroxy group.

The group Poly is the primary alkoxysilyl binder backbone providing flexibility, tensile strength and film formation for the color coating. Preferably, Poly is an organic backbone of monomeric units such as but not limited to ester, amide, urethane, urea, olefin units and at least with terminal alkoxysilyl groups (i.e., trialkoxysilyl groups as defined in the Definitions section). The backbone of Poly may be of any configuration, which preferably is a linear or branched configuration, and the linear configuration is the most preferred configuration. In a branched configuration of Poly, the optional pendant alkoxysilyl groups may be the termini of the branches. Because of the multiple condensation ability of each alkoxysilyl group of the alkoxysilyl binder, their condensation to form Si—O—Si bonds produces an in situ crosslinked alkoxysilyl binder forming a three dimensional network. All configurations of Poly, and preferably the linear configuration of Poly, produce this alkoxysilyl binder network with Si—O—Si connections which extend the backbone and interconnect separate backbones as cross links due to the multiple times an alkoxysilyl group can condense with other alkoxysilyl groups. Although it is not a limitation of the invention, it is believed that the in situ crosslinking occurs as well with the pretreatment alkoxysilyl small molecules to establish the three dimensional network throughout the combination of alkoxysilyl binder and small molecules.

The group Poly may have any structural configuration as described in the Definitions section, and preferably has a linear backbone configuration and may be formed of monomeric units of an ester, urethane, urea, amide or polyol (ether) group or any combination thereof. The designator y indicates the extent of Poly and is an integer designating the number of monomeric units of Poly forming the backbone. Accordingly, y is an integer of from about 2 up to about 1 million, preferably up to about 300,000, more preferably up to about 250,000, most preferably up to about 200,000.

When the monomeric unit of Poly is an ester, the ester monomeric unit may be formed of a C2-C10 linear or branched alkane diol or a C8-C20 aromatic diol, and a C3 to C10 linear or branched alkanodioic acid or a C8-C10 aromatic dicarboxylic acid or formed of a C3-C10 hydroxy alkanoic acid or a C8-C10 aromatic hydroxy carboxylic acid.

When the monomeric unit of Poly is a urethane, the urethane monomeric unit is formed of a C2-C10 alkanodiol and an $R^3$ diisocyanate wherein $R^3$ is as described below.

When the monomeric unit of Poly is a urea, the urea monomeric unit is formed of a C2-C10 linear or branched alkanodiamine and an $R^3$ diisocyanate.

When the monomeric unit of Poly is an amide, the amide monomeric unit is formed of a C2-C10 alkanodiamine and a C3 to C10 alkanodioic acid or C8-C10 aromatic dicarboxylic acid.

When the monomeric unit of Poly is a polyol, the polyol monomeric unit is a formed of ethylene oxide (linear) or propylene oxide (branched).

A preferred ester monomer of Poly is formed of glycol, 1,4-butanediol or 1,6-hexanediol and malonic acid, succinic acid, glutaric acid, adipic acid, phthalic acid, terephthalic acid or any combination thereof or alternatively, the Poly is formed from a hydroxy acid such as glycolic or lactic acid, ω-hydroxy propanoic acid, ω-hydroxybutanoic acid or p-hydroxybenzoic acid. An especially preferred ester monomer of Poly is formed of glycol(dihydroxy ethane) or 1,6-hexanediol and succinic acid, adipic acid or phthalic or terephthalic acid.

A preferred urethane monomer of Poly is formed of glycol, 1,4-butanediol or 1,6-hexanediol and isophorone diisocyanate, methylene bis(phenylisocyanate), toluene diisocyanate or 1,6-hexane diisocyanate. An especially preferred urethane monomer of Poly is formed of glycol or 1,6-hexanediol and isophorone diisocyanate or toluene diisocyanate.

A preferred urea monomer of Poly is formed of 1,3-propanediamine, 1,4-butanediamine or 1,6-hexanediamine and isophorone diisocyanate, methylene bis(phenylisocyanate), toluene diisocyanate or 1,6-hexane diisocyanate. An especially preferred urethane monomer of Poly is formed of 1,3-propanediamine or 1,6-hexanediamine and isophorone diisocyanate or toluene diisocyanate.

A preferred amide monomer of Poly is formed of 1,3-propanediamine, 1,4-butanediamine or 1,6-hexanediamine and malonic acid, succinic acid, glutaric acid, adipic acid, phthalic acid, terephthalic acid or any combination thereof. An especially preferred amide monomer of Poly is formed of 1,3-propanediamine or 1,6-hexanediamine and succinic acid, adipic acid or phthalic or terephthalic acid.

A preferred polyol of Poly is a PEG-200 to PEG-2000.

The Poly group may be any combination of ester, urethane, urea, amide and/or polyol block or random arrangements. For example:
a) a combination of polyester and polyurethane blocks may be formed from a diol and blocks of dicarboxylic acids and diisocyanates;
b) a combination of polyester and polyurea blocks may be formed from their respective reactants and the joinder between blocks may be formed as a urethane connection by reacting a polyester block terminating with a hydroxyl and a polyurea block terminating with an isocyanate;
c) a combination of polyester and polyamide blocks may be formed from a dicarboxylic acid and blocks of diols and diamines;
d) a combination of polyester and polyol blocks may be formed from a polyol and blocks of diol and dicarboxylic acid;
e) a combination of polyurethane and polyurea blocks may be formed from their respective reactants and the joinder between blocks may be formed as a urethane and/or urea connections;
f) a combination of a polyurethane and polyamide blocks may be formed from their respective reactants and the joinder between blocks may be formed as a urea connector by reacting a polyamide block terminating with an amine and a polyurethane block terminating with an isocyanate;
g) a combination of polyurethane and polyol blocks may be formed from a polyol and blocks of diol and diisocyanate;
h) a combination of polyurea and polyamide blocks may be formed from their respective reactants and the joinder between blocks may be formed as a urea connector by reacting a polyamide block terminating with an amine and a polyurea block terminating with an isocyanate;
i) a combination of polyurea and polyol blocks may be formed from a polyol and blocks of diamine and diisocyanate and the joinder between blocks may be formed as a urethane connector by reacting a polyol block terminating with a hydroxy and a polyurea block terminating with an isocyanate;
j) a combination of polyamide and polyol blocks may be formed from a polyol and blocks of diamine and dicarboxylic acid and the joinder between blocks may be formed as an ester connector by reacting a polyol block terminating with a hydroxy and a polyester block terminating with a carboxylic acid.

Provisos apply to the choice of the $U^2$ group. $U^1$ will always be urea when the trialkoxysilyl alkylenyl-G starting material is a trialkoxysilylalkylenylamine. Alternatively, $U^1$ will always be urethane when the trialkoxy alkylenyl-G starting material is an trialkoxysilylalkylenylalcohol (OH). In the following provisos, $U^1$ is always urea resulting from the preferred trialkoxysilylalkylenylamine starting material.
a) When Poly ends with an ester monomeric unit, $U^2$ is a urethane group and $U^1$ is a urea group.
b) When Poly ends with a urethane monomeric unit, $U^2$ is a urethane group and $U^1$ is a urea group.
c) When Poly ends with a urea group, $U^2$ and $U^1$ are both urea groups.
d) When Poly ends with an amide monomeric unit, $U^2$ and $U^1$ are both urea groups.
e) When Poly ends with polyol monomeric unit, $U^2$ is a urethane and $U^1$ is a urea group.

Like the $R^2$ group, the $R^3$ group may be a C2 to C12 linear or branched alkylenyl group, a C6-C16 alkylcycloalkyl group or a C6-C14 aromatic group. $R^2$ and $R^3$ are both the organic groups for the diisocyanate reactant forming the urethane and urea groups. Preferably, $R^2$ and $R^3$ may each independently be methylene bisphenyl (as in methylene bis(phenylisocyanate), toluenylenyl (as in toluene diisocyanate), hexanylenyl (as in hexamethylene diisocyanate), naphthalenyl (as in naphthalene diisocyanate), methylene bis cyclohexylenyl (as in methylene bis(cyclohexylisocyanate) which is hydrogenated methylene bis(phenylisocyanate)) and isophoronylenyl (as in isophorone diisocyanate).

In each of the organic alkoxysilyl binders of Formula IA, Poly may optionally contain one or more trifunctional groups such as a triol or triamine which function to provide pendant alkoxysilyl groups for the organic alkoxysilyl binder.

The third hydroxyl or amine of the trifunctional group constitutes a link to a pendant $SiX_3$ through the same Ct-$R^1$ group of Formula IA. This version of the organic alkoxysilyl binder comprises Formula IB in which Z is trifunctional group linked through Ct-$R^1$ to the third $SiX_3$:

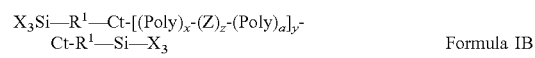

Formula IB

For Formula IB, the Z group is derived from a triol or triamine starting material of the formula III

Formula IV in which the Y groups are hydroxyl or amine or when Poly is an ester, the Z group alternatively may be a tricarboxylic acid. Except for the tricarboxylic acid embodiment, Formula IV is a homolog starting material of the diol or diamine starting material for the ester, urethane, urea, amide or polyol monomeric unit in which the —$R^5$—Y branch group of Formula IV has the same configuration as the organic moiety of the diol or diamine. For example, if the Poly is a polyurethane or polyurea constructed from a propane diol, the triol compound would be 2-hydroxymethyl-1,3-propane diol, also known as trihydroxymethyl methane. As stated above for Z, the third Y group, the pendant Y group of the triol or triamine (hydroxyl or $NH_2$) is bonded through Ct to $R^1$—$SiX_3$ so that the pendant Y of the triol or triamine starting material of Formula IV becomes part of a urethane or urea group just as shown for Ct of Formula I. The resulting full Formula IB in which Z is has the structure =R⁴—R⁵—Ct-R¹—SiX₃ is:

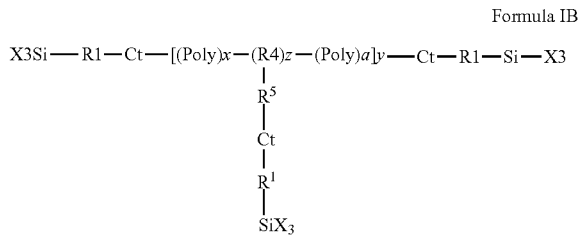

Formula IB

For Formula IB, the designator z indicates the number of pendant alkoxysilyl groups present in the alkoxysilyl binder. For alkoxysilyl binders having multiple pendant alkoxysilyl groups, Z of Formula IB (i.e., =R⁴—R⁵—Ct-R¹—SiX₃) is randomly distributed throughout the alkoxysilyl binder polymer backbone. Accordingly, designator z is an integer from 1 to 1 thousand and specifies the number of trifunctional groups present in Formula I'. Preferably, z is an integer from 1 to 100, more preferably from 1 to 10, especially more preferably from 1 to 5 and most preferably from 1 to 3. The sum of the integer designators x, z and a equals y so that the weight average molecular weight of the alkoxysilyl binder of Formula I' is the same as the weight average weight of the alkoxysilyl binder of Formula I.

Versions of the Alkoxysilyl binder may be all of Formula IA or all of Formula IB which is a alkoxysilyl binder having terminal and pendant alkoxysilyl groups. The alkoxysilyl binder as well may be a mixture of Formula IA and Formula IB. For a mixture, the ratio of Formula IA to Formula IB may range from may be in a range of 100:1 to 1:100, preferably 50:1 to 10:9 or 25:1 to 2:1 or 20:1 to 10:1.

The weight average molecular weight of Formula IA and Formula IB may range from about 1 KDa to about 1 MDa, preferably from about 1 KDa to about 500 KDa, more preferably from about 1 KDa to 300 KDa, especially more preferably from at least about 2 KDa up to about 250 KDa, most preferably from at least about 2 KDa up to about 150 to about 200 KDa. The designator y of Formula IA is chosen to provide an average molecular weight in this range. Similarly, the sum of the designators x, z and a of Formula IB is chosen to equal the choice for y and the average molecular weight in this range.

The choice of the ratio of z relative to the two terminal alkoxysilyl groups for Formula IB may preferably range from 1:2 to 100:2 more preferably from 1:2 or 2:2 to 20:2, most preferably at least 1:2 up to 5:2 or 10:2. The presence of the pendant alkoxysilyl group provides additional crosslinking among the alkoxysilyl binder molecules and with the pretreatment small molecule. Although it is not a limitation of the invention, it is believed that the additional crosslinking is capable of delivering a significant remanent color coating on keratin fibers.

Preferred embodiments of the organic alkoxysilyl binder of Formula IA (with terminal alkoxysilyl groups alone) provide:
a) Poly as a polyurethane constructed of a C4-C6 alkane diol, preferably hexane diol and isophorone diisocyanate, toluene diisocyanate or methylene bis(phenylisocyanate), or
b) Poly as a polyethylene glycol or polypropylene glycol or
c) Poly as a polyester constructed of a C2-C6 alkane diol, preferably ethylene glycol and succinic acid, adipic acid or any form of phthalic acid, preferably terphthalic acid.

The Ct group is formed from a C1-C4 alkane diisocyanate. The R¹—SiX₃ group is formed from an ω-amino propyl or isobutyl triethoxysilane or the trimethoxysilane homolog.

A preferred embodiment of the organic alkoxysilyl binder of Formula IB has Poly, Ct and R¹—SiX₃ as described above for the preferred polyurethane and polyester organic alkoxysilyl binders of Formula IA of the foregoing subparagraphs a and c except that from about 0.1 wt % to about 5 wt %, preferably from about 0.5 wt % to about 3 wt % of the C4-C6 alkane diol is replaced by 3-(3-hydroxyprop-1-yl)-1,6-hexanediol so that the ratio of pendant alkoxysilyl to terminal alkoxysilyl groups of preferred Formula IB is from 1:2 to 5:2, preferably 1:2 to 3:2.

An especially preferred embodiment of the alkoxysilyl binder of Formula IA comprises Formula V which is a linear a polyester with terminal alkoxysilyl groups:

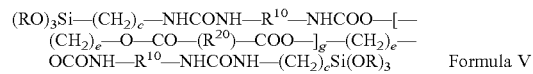

Formula V wherein c is an integer of 3-6, preferably 3, e is an integer of 2 to 8, preferably ethylene, butane or hexane diol, more preferably ethylene, R²⁰ is divalent benzenenyl (i.e., the divalent benzene residue of any benzene dicarboxylic acid including phthalic, isophthalic and terephthalic acids) or (CH₂)_f wherein f is an integer of 4 to 8, preferably R²⁰ is a terephthalic acid residue or a succinic or adipic acid residue, more preferably a terephthalic acid residue, g is an integer of 10 to 300,000, R¹⁰ is a C4 to C8 alkylenyl group, preferably hexylenyl and R is methyl or ethyl.

The preferred weight average molecular weight of preferred versions of Formulas IA, IB and V may be in the range of about 5 KDa to about 200 KDa, preferably about 5 KDa to about 50 KDa to about 100 KDa.

Versions of the Poly monomer displaying flexible alkylenyl groups and stiff aromatic groups, and block combinations for Poly can enable development of hard and soft domains within the film formed of the alkoxysilyl binder polymer and pretreatment components. The flexibility of long alkylenyl group and the rigidity of the aromatic groups, as well as the hydrogen bonding between intermolecular carboxyl groups with ester, amine, urethane and/or urethan groups act in part to promote soft and hard domains. The presence of hard and soft domains at least in part contributes to the tensile strength and flexibility to the color coating.

Alkoxysilyl Catalyst

The film forming composition further may comprise a catalyst to manage the rate of alkoxysilyl condensation to form Si—O—Si networks. As a base line procedure, contact of the alkoxysilyl binder with water is sufficient to carry out the condensation. However, water hydrolysis and condensation of alkoxysilyl groups under neutral conditions is extremely slow. See for example the discussion of alkoxysilane condensation in A Issa and A Luyt, Polymers, 2019, 11, 537 et seq. Use of a catalyst to change the pH of the hydrolysis/condensation medium speeds the condensation and an acid medium is preferred. Lewis acid agents such as organosulfate, organophosphate, organotitanium, organozirconium, organo aluminum, organozinc, boron halides, organoboron, boronic acid, mineral acids such as hydrochloric, sulfuric and nitric acids and organic acids such as acetic, oxalic and trifluoroacetic acids are useful for increasing the rate of hydrolysis/condensation. Ammonia and organoamine compounds also are useful especially for the second phase of the process, condensation. Choice of a catalyst may be managed by consideration of the cosmetically acceptable and pharmaceutically acceptable nature of the catalyst. For this reason, an excellent catalyst for this purpose, organotin compounds are not acceptable because of their toxicity. A combination of an acidic agent such as an organophosphate, organotitanium or organoboronate agent followed by a basic wash with dilute ammonia or an organic amine affects an efficient, rapid condensation of the alkoxysilyl groups of the alkoxysilyl binder and its combination with the pretreatment composition. Preferable acidic catalysts in this regard include bis(2-ethylhexyl) phosphate ester, titanium diisopropoxide bis(acetylacetonate), bis(2-ethylhexyl) sulfate ester, methyl sulfate ester, tri(pentafluorophenyl) boron or mono or di acetoboronate.

The Aza Michael Film Forming Composition

Embodiments of the Aza film forming composition are directed to multiple components comprising a Michael binder and an aza linker that are adapted to combine in situ to crosslink through an Aza-Michael addition. The Michael binder comprises a silicone polymer having pendant and/or terminal α,β-unsaturated alkenoyloxy groups. The aza linker comprises a silicone polymer having pendant and/or terminal organoamine groups and optional pendant and/or alkoxysilyl groups. Preferably, the Michael binder and aza linker are linear and/or branched, more preferably linear. The film forming composition further comprises one or more microparticle pigments and/or color bodies. The film forming composition also comprises a medium in which the multiple components, pigment(s) and/or color bodies are dispersed, mixed and/or otherwise contained (color bodies being synonymous with pigments). The film forming composition may but not necessarily further comprise one or more ancillary components as adjuncts for helping and/or promoting characteristics of the color coating on keratin fibers. Application of the film forming composition to keratin fibers may also include a conversion step such as drying and curing to evaporate residual medium from the film forming composition on the surfaces of the keratin fibers and to cause the aza-michael addition reaction thereby producing a chain extended, cross linked polymer network comprising a film.

The Michael binder and aza linker components of the film forming composition are separately maintained until immediately prior to use. The film forming composition is prepared for use for application to keratin fibers by combining and mixing the Michael binder and aza linker components in media according to the proportional quantities described below. The pigment/color bodies with dispersant may also be combined as described below to form the film forming composition with pigment/color bodies.

Michael Binder

The Michael binder may be a silicone polymer with at least two pendant and/or terminal α,β unsaturated alkenoyloxy groups, and preferably at least two of the α,β unsaturated alkenoyloxy groups are terminal groups. The Michael binder may have a linear or branched, preferably a linear configuration.

In particular, embodiments of the Michael binder of the film forming composition comprise a polydimethylsiloxane-type polymer having at least two or at least three α,β unsaturated alkenoyloxy groups attached to siloxane units of the polymer. The α,β-unsaturated alkenoyloxy groups comprise the Formula EOY:

$$R^1R^2C=CR^3COO—R^4—$$ Formula EOY

In Formula EOY, each of $R^1$ and $R^2$ may independently be hydrogen or a C1-C6 linear or branched alkyl group. Preferably at least one of $R^1$ and $R^2$ is hydrogen. The group $R^3$ may be hydrogen or methyl. The group $R^4$ is a part of the connector group that joins Formula EOY to silicon of a siloxane unit of the polydimethylsiloxane-type silicone polymer. The group $R^4$ may be a C1-C12 linear alkylenyl group, a linear C3-C12 cycloalkylalkyl or cycloalkyl group, a linear C6-C20 arylalkyl group or C6 to C20 aryl group wherein $R^4$ may be optionally substituted in chain by one or more of an ether oxygen, thioether sulfur and/or amine groups or pendantly by hydroxyl groups. The group $R^4$ is bonded directly with a silicon atom of a siloxane unit of the dimethylsilxane-type silicone polymer. A preferred embodiment of Formula EOY is $H_2C=CR^3COO—R^4—$, and a more preferred embodiment is $H_2C=CHCOO—R^4—$.

Embodiments of the Michael binder of the film forming composition may be linear and/or branched, preferably linear and comprise a silicone polymer constructed of D and M siloxane monomeric units. Branched forms may include T units ($MeSiO_3$) in the backbone which form branch junctions for branch chains carrying D and M units, however, linear forms are preferred. The Michael binder silicone polymer comprises Formula I:

  Formula I

For Formula I, two or more of the D and/or M units are modified with X which is the α,β-unsaturated alkenoyloxy group of Formula EOY. Each of the siloxane units $Me_2SiO$ and $Si(X)MeO$ comprise monomeric siloxane D units with Me being methyl. The terminal units $(X_z)SiMe_{3-z}$ comprise monomeric siloxane M units. The designator z is zero or 1 so that the terminal units may have a single Formula EOY group or may be a trimethylsiloxane unit. The designator x primarily determines the molecular size of the silicone polymer Michael binder and may range from about 2 to 200,000, preferably from about 5 to about 50,000, more preferably from about 5 to about 1,000. The designator y primarily determines the number of Formula EOY groups in the Michael binder and may range from 0 to about 100, preferably about 2 to about 25, more preferably about 2 to about 20. The sum of designators y and z must at least be 1 and preferably 2 so that Formula I has at least one, preferably at least 2 Formula EOY groups. The designator x primarily determines the length of the linear silicone polymer and may integer range from about 3 to about 200,000, preferably up to about 500, more preferably up to about 200 with exemplary integer sums of up to about 100. The multiple monomeric units of $Me_2SiO$ and $(X)SiMeO$ are randomly distributed in Formula I.

Preferred embodiments of Formula I are those with designator y as zero and z as 1. These embodiments provide Michael binders with terminal Formula EOY only. Additional preferred embodiments are those with designator x as at least 5, designator y as 1 to 5 and z as 1. These embodiments provide Michael binders with terminal Formula EOY's and from 1 to 5 pendant Formula EOY's. Yet other especially preferred embodiments are those with designator x as at least 10, designator y as 2 to 6 and z as zero. These embodiment provide Michael binders with 2 to 6 pendant Formula EOY's and no Formula EOY's as termini. Instead, the Michael binder is terminated with $Me_3SiO$ groups.

Another preferred embodiment of the foregoing preferred embodiments of Formula I has Formula EOY as $H_2C=CR^3COO—R^4—$. More preferred of these especially preferred embodiments of Formula I (Formula EOY with designations of $R^1$ and $R^2$ as hydrogen) are those in which $R^4$ is a linear C2-C8 alkylenyl group and more especially preferably is the $R^4$ group as $—CH_2CHOH—CH_2—O—$ $(CH_2)_n$— wherein n is an integer of 1 to 6. Most especially preferably for all of these embodiments of Formula I has Formula EOY as $H_2C=CR^3COO—CH_2CHOH—CH_2—O—(CH_2)_3—$ An especially preferred embodiment of the Michael binder of Formula I is Formula IV:

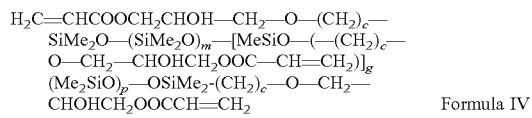

Formula IV

This especially preferred embodiment of the Michael binder provides Formula EOY as terminal groups and as pendant groups of the polydimethylsiloxane-type polymer. In this embodiment, designator c determines the length of the alkylenyloxo group connecting the α,β-unsaturated alkenoyloxy group to silicon of the polymer backbone. Designator c may be an integer of 1 to 6, preferably 3. The designators m and p establish the size or length of the linear silicone polymer and separate the pendant α,β-unsaturated alkenoyloxy groups from the terminal α,β-unsaturated alkenoyloxy groups. Designator m and p may each independently range from about 5 to about 100. Designator g establishes how many pendant α,β-unsaturated alkenoyloxy groups are present in this embodiment of the Michael binder. Designator g may be zero which provides a Formula IV embodiment with no pendant α,β-unsaturated alkenoyloxy groups but with termini each with an α,β-unsaturated alkenoyloxy group. Designator g may alternatively be an integer of from 1 to about 10. In this embodiment, the —O—$(CH_2)_c$-moiety connects Formula EOY to the silicone backbone as a carbon to silicon bond. To accomplish the joinder, a route through an alkenyl moiety may be followed. An alkenyloxoalkyl bromide may be combined with a silicon halide using an alkyl lithium or Grignard reagent to provide an Si-alkyloxoalkene moiety. The olefin bond of the alkene group may be epoxidized and the epoxy group combined with the α,β-unsaturated alkenoic acid such as acrylic acid to form Formula EOY.

Preferred embodiments of Formula IV include those with g as an integer of from 1 to 5 and c and c' each as an integer of 1 to 3 and each of m and p as 10 to 50. This embodiment provides a Michael binder with Formula EOY as the termini and as 1 to 5 pendant groups. Another preferred embodiment of Formula IV provides g and p as zero, and c and c' as an integer of 1 to 3. This embodiment provides a Michael binder with Formula EOY as termini only.

Aza Linker

In particular, embodiments of the aza linker of the film forming composition may be linear and/or branched, preferably linear and comprise a polydimethylsiloxane-type silicone polymer comprising a combination of M1 units, D units and M2 units as Formula V:

$M1-(D)_d-M2$  Formula V

The M1 and M2 units constitute the termini of the silicone polymer as indicated. The D units form the backbone of the silicone polymer as indicated. Branched forms may include T units ($MeSiO_3$) in the backbone which form branch junctions for branch chains carrying D and M units, however, linear forms are preferred. The M1 and M2 units are selected from $Me_3SiO$ units, A-$SiMe_2O$ units in which A is an organoamine group and —$SiOR_3$ units (trialkoxysilyl units) in which R is ethyl or methyl. The D units are selected from $SiMe_2O$ units and A-SiMeO units. For the D units, the designator d indicates the length of the linear silicone polymer and may range from 3 to 30,000, preferably 3 to 25,000, more preferably 2,000 to 10,000.

For the D and M units, the A moiety, an organoamine group, comprises Formula OA:

Formula OA

The group $R^{10}$ may be a linear or branched C1-C10 alkylenyl group or a linear or branched C6-C14 alkylarylenyl group, preferably a linear C2-C4 alkylenyl group, more preferably an ethylenyl group. The group $R^{11}$ may be a linear or branched C1-C10 alkylenyl group or a linear or branched C6-C14 alkylarylenyl group, preferably a linear C2-C5 alkylenyl group, more preferably a propylenyl or iso-butyl group. The designator r may be zero or an integer of 1 to 3. The group $R^{11}$ is bonded to silicon of a siloxane unit and is also bonded to $H_2N$— when designator r is zero.

A first embodiment of the aza linker may have both M1 and M2 units as A-$SiMe_2O$ units. A second embodiment of the aza linker may have M1 as an A-$SiMe_2O$ unit and M2 as an —$SiOR_3$ unit. For these first and second embodiments D may have a multiple number of $SiMe_2O$ units. For these first and second embodiments, D may alternatively have 1 to 10 A-SiMeO units and a multiple number of $SiMe_2O$ units. A third embodiment of the aza linker may have both of M1 and M2 as —$SiOR_3$ units and D may have 1 to 10 A-SiMeO units and a multiple number of $SiMe_2O$ units. A fourth embodiment of the aza linker may have both of M1 and M2 as $Me_3SiO$ units and D may have 1 to 10 A-SiMeO units and a multiple number of $SiMe_2O$ units.

Preferred embodiments of the aza linker as $M_1$-$(D)_d$-$M_2$ may be selected to provide at least 2 pendant and/or terminal D, M1 and M2 units with Formula OA groups and no trialkoxysilyl groups. Preferred embodiments may be also selected to provide at least one D unit and one of the M1 and M2 units with Formula OA groups and the other of the M1 and M2 units as a trialkoxysilyl group. Preferred embodiments may also be selected to provide at least 2 D units with Formula OA groups and the M1 and M2 units both as trialkoxysilyl groups. More preferred versions of these preceding preferred embodiments may also be selected to provide additional D units with from 2 to 6 Formula OA groups. Especially preferred versions of these preceding preferred and more preferred embodiments may be selected to provide Formula OA groups only in D units and trialkoxysilyl groups as both of the M1 and M2 units.

Formula V as the preferably linear polydimethylsiloxane-type polymeric aza linker may be expanded to show the monomeric units possible. Accordingly, the aza linker is formed from the following list of monomeric units with the M and D designations shown below the list:

| | |
|---|---|
| $(Me_3SiO)$ | M-T1 |
| $(Si(OR)_3$ | M-T2 |
| $(A-SiMe_2O)$ | M-T3 |
| $(SiMe_2O)_o$ | D-B1 |
| $(SiMe_2O-A)_p$ | D-B2 |

The first three units form termini (M-T1-M-T2-M-T3) for the aza linker. The last two units form the backbone of the aza linker (D-B1-D-B2) with the majority of the backbone units being the dimethylsiloxane unit, D-B1. The designator o for the dimethylsiloxane unit is an integer of from 2 to 100. The designator p for the siloxane backbone groups carrying Formula OA may be zero or an integer of from 1 to 10. The symbol A stands for Formula OA described above. M-T3 and D-B2 carry the amine group Formula OA. Unit M-T2 is the trialkylsilyl group. As a terminus, silicon of the M-T2 unit is bound to oxygen of the adjacent D-B1 unit of the backbone of the dimethylsiloxane-type polymer forming the aza linker.

As described above, embodiments of the aza linker may be ordered according to the identity of the group as the termini. In all of these embodiments the silicone backbone primarily is the D-B1 unit. The number of D-B1 units in the backbone is calculated to provide the weight average molecular weight range of the aza linker as described below. These embodiments include but are not limited to:

A) Both termini as M-T1 (trimethylsiloxane) in which case the backbone will carry at least one unit of the amine Formula OA as D-B2, and preferably two or three D-B2 units.
B) One terminus as M-T1 and the other terminus as M-T2 (alkoxysilyl). In this case, the backbone will carry at least one of the amine Formula OA as unit D-B2 and preferably two or three D-B2 units.
C) One terminus as M-T1 and the other as M-T3 (M unit carrying organoamine Formula OA) in which case the backbone will carry at least one amine Formula OA as unit D-B2 and preferably two or three D-B2 units.
D) One terminus as M-T2 (alkoxysilyl) and the other as M-T3 (M unit carrying organoamine Formula OA) in which case the backbone will carry at least one amine Formula OA as unit D-B2 and preferably two or three D-B2 units.
E) Both termini as M-T2 (alkoxysilyl) in which case the backbone will carry at least one amine Formula IA as unit D-B2 and preferably two or three D-B2 units.
F) Both termini as M-T3 (M unit carrying organoamine Formula OA) in which case the backbone may have no D-B2 units.
G) Both termini as M-T3 in which case the backbone may carry at least one or two D-B2 units.

Embodiments of the Michael binder of the film forming composition may have their designators chosen to indicate a number of siloxane units providing a weight average molecular weight for the Michael binder in a range of about 0.5 KDa to about 10 KDa, preferably about 0.5 KDa to about 5 KDa, more preferably about 1 KDa to about 5 KDa, most preferably about 1 KDa to about 3 KDa, especially about 1 KDa to about 2 KDa.

Embodiments of the aza linker of the film forming composition may have the number of their monomeric units chosen to provide a weight average molecular weight for the aza linker in a range of about 5 KDa to about 50 KDa, preferably about 5 KDa to about 30 KDa, more preferably about 5 KDa to about 20 KDa, most preferably about 8 KDa to about 20 KDa, especially about 10 KDa to about 20 KDa. The weight average molecular weight of the aza linker will primarily be provided by the number of dimethylsiloxane units present in backbone of the polydimethylsiloxane-type silicone aza linker.

The Michael binder and aza linker molar concentrations in the film forming composition deliver a ratio of Michael to aza groups. In some embodiments of the film forming composition, the Michael binder provides a number of $\alpha,\beta$ unsaturated alkenoyloxy groups (Michael groups) equal to the number of organoamine groups (aza groups) of the aza linker. In preferred embodiments of the film forming composition, the Michael binder provides an excess number of Michael groups relative to the number of aza groups of the aza linker. This ratio enables Michael-aza addition of the Michael binder with the amine groups of the small molecule of the pretreatment composition. In more preferred embodiments of the film forming composition, the Michael binder provides at least 2 to 8 Michael groups per 2 to 6 aza groups of the aza linker.

The CDI Film Forming Composition

Embodiments of the CDI film forming composition are directed to multiple components comprising a CDI binder and a CDI linker that are adapted to combine in situ to crosslink through a carboxylic acid-carbodiimide (acid-CDI) addition. The CDI binder comprises an olefinic polymer, silicone polymer or olefinic-silicone block copolymer having at least 2 pendant and/or terminal carboxylic acid groups. The CDI binder is preferably linear or branched, more preferably linear. The CDI linker comprises an alkylenyl, aromatic or alkylenyl aromatic polymer having multiple in chain segments of carbodiimide; or a polymer of ester, urethane or urea monomeric residues having pendant alkylenyl single carbodiimide groups. The CDI linker is preferably linear or branched, more preferably linear. The CDI film forming composition further comprises one or more microparticle pigments and/or color bodies. The CDI film forming composition also comprises a medium in which the multiple components, pigment(s) and/or color bodies are dispersed, mixed and/or otherwise contained. The CDI film forming composition may but not necessarily further comprise one or more ancillary components as adjuncts for helping and/or promoting characteristics of the color coating on keratin fibers. Application of the CDI film forming composition to keratin fibers may also include a conversion step such as drying and curing to evaporate residual medium from the CDI film forming composition on the surfaces of the keratin fibers and to cause the acid-CDI addition reaction thereby producing a chain extended, crosslinked polymer network comprising a film.

The CDI binder and CDI linker components of the CDI film forming composition are separately maintained until immediately prior to use. The CDI film forming composition is prepared for use for application to keratin fibers by combining and mixing the CDI binder and CDI linker components in media according to the proportional quantities described below. The pigment/color bodies with dispersant may also be combined as described below to form the CDI film forming composition with pigment/color bodies.

CDI Binder

The CDI binder may be a homopolymer, a copolymer, a terpolymer or a multiple block polymer having at least two carboxylic acid groups. Moreover, the polymeric nature of the CDI binder may be as an organic polymer, a silicone polymer or organosilicone polymer, each of which is configured to have a linear and/or branched configuration, preferably a linear configuration.

In particular, embodiments of the CDI binder of the film forming composition comprise
an olefinic, silicone or organosilicone polymer of Formula I having at least two carboxylic acid groups.

$$\text{MUE-(MU1)}_x\text{-(MUX)}_y\text{-(MU2)}_z\text{-(MU3)}_a\text{-(MU3X)}_b\text{-MUE}$$

The symbols MUE, MU1, MUX, MU2, MU3 and MU3X stand for monomeric units of the carboxylic acid polymer. The CDI binder of Formula I may be linear or branched, preferably linear. The monomeric units MU1, MUX (X for acid) and MU2 respectively are hydrophobic, acid and hydrophilic olefinic monomeric units. MU3 and MU3X respectively are siloxane units with the X siloxane unit bearing a pendant alkanoic acid group. MUE (E for end) is the termination unit of the polymer and may be any of the olefinic monomeric units or the siloxane unit. An olefinic polymer comprises either or both of MU1 and MU2 combined with MUX and the termini of this polymer (MUE) may be any of these three former monomeric units. If hydrophilic and hydrophobic units are present in the olefinic polymer, these olefinic monomeric units may be randomly distributed throughout the olefin polymer or may form blocks of hydrophilic and hydrophobic units with the carboxylic acid units preferably being within the hydrophilic blocks. A silicone polymer comprises a combination of MU3 and MU3X with its termini being MU3. The carboxylic acid units may be randomly distributed throughout the silicone polymer. An organosilicone polymer comprises blocks of the olefinic polymer and the silicone polymer. The olefinic polymer blocks may have the monomeric units arranged as in the olefinic polymer. The acid containing units may be MUX or MU3X and preferably are MUX. The CDI binder comprising the olefinic, silicone or organosilicone polymer formed of the foregoing monomeric units may linear or branched preferably be linear.

In particular, these monomeric units may be linear or branched, preferably linear and are as follows.
a) MU1 is a hydrophobic olefinic monomeric unit comprising a C2-C10 alkene residue, a C4-C12 alkadiene residue and/or a C6-C10 aromatic/alkylaromatic vinyl residue.
b) MU2 is a hydrophilic olefinic monomeric unit comprising a vinyl C2-C16 alkanoic ester residue, a C1-C14 alkyl or hydroxyalkyl C2-C14 alkenoic ester residue, a C2-C10 alkenoic amide residue or N—C1-C4 alkyl substituted version of the amide residue.
c) MUX is an acidic olefinic monomeric unit comprising a C3-C10 alkenoic acid residue or a C4-C10 alkadienoic acid residue.
d) MU3 is a dimethylsiloxane monomeric unit.
e) MU3X is a monomethylsiloxane monomeric unit bound to an alkanoic acid of at least 4 carbons with one of the alkyl carbons of the alkanoic acid optionally having a hydroxy group.
f) MUE is a single terminal monomeric unit of MU1, MU2 or MUX when the polymer is an olefinic polymer or an organosilicone polymer.
g) MUE is a single terminal monomeric unit of MU3 with an additional methyl, i.e., a trimethylsiloxane unit when the polymer is a silicone polymer.

The designators x, y, z, a and b indicate the number of the corresponding monomeric units present in the corresponding polymer. Irrespective of the kind of polymer, its molecular size is the sum of x, y, z, a and b which may be an integer of from about 3 up to about 1 million, preferably up to about 300,000, more preferably up to about 250,000, most preferably up to about 200,000. Each of the designators x, y, z, a and b independently indicates the number of corresponding monomeric units forming the linear polymeric backbone. Each of x, z and a may be zero or an integer of from 1 up to about 100,000. Designators y and b indicate the number of acid units present in the polymer with y indicating the number of olefinic carboxylic units and b indicating the number of siloxane carboxylic acid units. Designators y and b may each independently be zero or an integer of 1 to 100, preferably 1 to 50, more preferably 1 to 20 provided that at least two carboxylic acid groups are present. Additionally, when the polymer is a silicone polymer b is zero and y is an integer. When the polymer is an olefin polymer, b is an integer and y is zero. When the polymer is an organosilicone polymer one of b and y may be zero and the other an integer or both may be an integer.

Preferred forms of Formula I include:
a) Formula I in which the designators x and z are each at least 10, designator y is at least 3, designators a and b are both zero and terminal MUE is MUX. This is the olefinic polymer.
b) Formula I in which each of designators x, z and a are 10 to 100, designator y is 1 to 50, designator b is zero, terminal MUE is MUX. This is the organosilicone block copolymer with olefinic unit carboxylic acid groups.
c) Formula I in which designators x, y and z are zero, designator a is at least 20, preferably at least 40, designator b is 1 to 50 and terminal MUE is MU3X or as MU3. This is the silicone polymer with termini as either dimethylsiloxane bearing an alkylalkanoic acid group or a trimethylsiloxane unit.
d) Formula I in which each of designators x, z and a are 10 to 100, each of designators y and b independently is 1 to 50, terminal MUE is MUX or MU3. This is the organosilicone polymer with olefinic and siloxane units bearing the carboxylic acid.

A preferred CDI binder comprises an olefinic or organosilicone polymer with three or more pendant and/or terminal carboxylic acid groups, a weight average molecular weight of from about 0.5 KDa to about 10 KDa, preferably about 0.5 KDa to about 5 KDa; and at least one or more pendant groups selected from an alkyl alkylenylcarboxyate ester group, an alkyl group, an alkylenyloxycarbonylalkyl group and a hydroxalkyl group.

A preferred CDI binder also comprises a silicone polymer with three or more pendant C4-C6 alkanoic acid groups and a weight average molecular weight of from about 0.5 KDa to about 10 KDa, preferably about 0.5 KDa to about 5 KDa.

Another preferred CDI binder of Formula I comprises an olefin polymer of from 3 to 10, preferably 3 to 5 carboxylic acid groups, a weight average molecular weight of from about 0.5 KDa to about 10 KDa, preferably about 0.5 KDa to about 5 KDa; and in which MU1 is butene, pentene, hexene, styrene or any combination thereof; MUX is (meth) acrylic acid, crotonic acid, pentenoic acid, hexenoic acid, fumaric acid, maleic acid, itaconic acid glutaconic acid, citraconic acid or mesaconic acid, preferably (meth)acrylic acid, maleic acid, fumaric acid or crotonic acid; MU2 is vinyl acetate, vinyl propanate, vinyl butanate, C1-C3 alkyl or hydroxyalkyl (meth)acrylate, C1-C3 alkyl or hydroxyalkyl crotonate, C1-C3 alkyl or hydroxyalkyl pentanoate, C1-C3 dialkyl or di-(hydroxyalkyl) fumarate, C1-C3 maleate or the corresponding primary amides or C1-C3 alkyl secondary amides or any combination thereof.

Another preferred CDI binder of Formula I comprises a silicone polymer of from 3 to 10, preferably 3 to 5 carboxylic acid groups; the weight average molecular weight of from about 0.5 KDa to about 10 KDa, preferably about 0.5 KDa to about 5 KDa; and in which MU3X is MeSiO—$(CH_2)_n$—CHOH—$(CH_2)_2$—COOH with n as an integer of from 1 to 6, preferably 2 or 3.

Another preferred CDI binder of Formula I comprises an olefin polymer of from 3 to 10, preferably 3 to 5 carboxylic acid groups, a weight average molecular weight of from about 0.5 KDa to about 10 KDa, preferably about 0.5 KDa to about 5 and in which MU1 is hexene or styrene, MUX is (meth)acrylic acid or crotonic acid, MU2 is vinyl acetate, vinyl C8-C12 isoalkanoate, methyl, ethyl or isopropyl (meth)acrylate or the corresponding hydroxymethyl, hydroxyethyl or hydroxyisopropyl analogs, methyl, ethyl or isopropyl crotonate or the corresponding hydroxymethyl, hydroxyethyl or hydroxyisopropyl analogs.

Another preferred CDI binder of Formula I is an organosilicone block copolymer with carboxylic acid groups in the olefin block. The designators of this preferred CDI binder include designator x as zero meaning no hydrophobic olefinic units, designator b as zero meaning no acid groups pendant to siloxane units, designator a as at least 10 meaning at least 10 dimethylsiloxane units, designator z as at least 10 meaning at least 10 hydrophilic olefinic units, designatory y as 1 to 50 meaning 1 to 50 carboxylic acid olefinic units and MUE is MUX meaning terminal olefinic carboxylic acid units.

Another preferred CDI binder of Formula I is an olefinic polymer comprising at least monomeric units of alkyl (meth) acrylate and/or crotonate, and (meth)acrylic acid and/or crotonic acid. The acid number of this polymer is from about 50 to about 600 preferably about 100 to about 400.

A more preferred CDI binder of Formula I is an olefinic polymer in which the acid monomeric unit is (meth)acrylic acid and/or crotonic acid at about 0.3% to about 75% by weight; the hydrophilic unit is hydroxyethyl or hydroxypropyl (meth)acrylate and/or crotonate at about 0% to about 20% by weight; the hydrophobic monomer is methyl or ethyl (meth)acrylate or crotonate at about 5% to about 20% by weight, wherein all weights are relative to the total weight of the polymer.

Exemplary olefinic polymers as the CDI binder include organic copolymers such as acrylic acid/ethyl acrylate/N-tert-butylacrylamide terpolymers such as the product sold under the name Ultrahold 8 and that sold under the name Ultrahold Strong by the company BASF; (meth)acrylic acid/tert-butyl (meth)acrylate and/or isobutyl (meth)acrylate/C1-C4 alkyl (meth)acrylate copolymers such as the acrylic acid/tert-butyl acrylate/ethyl acrylate terpolymer sold by the company BASF under the name Luvimer 100P; (meth)acrylic acid/ethyl acrylate/methyl methacrylate terpolymers and tetrapolymers such as the ethyl acrylate/methyl methacrylate/acrylic acid/methacrylic acid copolymer such as the product sold under the name Amerhold DR-25 by the company Amerchol; methyl methacrylate/butyl or ethyl acrylate/hydroxyethyl or 2-hydroxypropyl acrylate or methacrylate/(meth)acrylic acid tetrapolymers such as the methyl methacrylate/butyl acrylate/hydroxyethyl methacrylate/methacrylic acid tetrapolymers sold by the company Rohm & Haas under the name Acudyne 255.

Additional examples of organic polymers include copolymers of acrylic acid and of C1-C4 alkyl methacrylate and terpolymers of vinylpyrrolidone, of acrylic acid and of C1-C20 alkyl, for example lauryl, methacrylate, such as that sold by the company ISP under the name Acrylidone M and the copolymer of methacrylic acid and of ethyl acrylate sold under the name Luvimer MAEX by the company BASF.

Exemplary silicone polymers bearing pendant carboxylic acid groups as the CDI binder include dual-end carboxy silicones such as X-22-162C from Shin Etsu and Silform INX (INCI name: Bis-Carboxydecyl Dimethicone) from Momentive; single-end carboxy silicone such as X-22-3710 from Shin Etsu. and other carboxy silicones such as Grandsil PCA such as in Grandsil SiW-PCA-10 (INCI name: Dimethicone (and) PCA Dimethicone (and) Butylene Glycol (and) Decyl Glucoside from Grant Industries.

Exemplary organosilicone polymer as CDI binder include multi-block carboxysilicone polymer (tradename Belsil® P1101) having INCI name: Crotonic Acid/Vinyl C8-12 Isoalkyl Esters/VA/Bis-Vinyldimethicone Crosspolymer and a similar organosilicone polymer having the technical name of Crotonic Acid/Vinyl C8-12 Isoalkyl Esters/VA/divinyldimethicone Crosspolymer from Wacker Chemie AG.

Additional exemplary silicone and organosilicone polymer functioning as CDI binder include name HUILE M 642 by the company Wacker, under the names SLM 23 000/1 and SLM 23 000/2 by the company Wacker, under the name 176-12057 by the company General Electric, under the name FZ 3703 by the company OSI and under the name BY 16 880 by the company Toray Silicone as well as Noveon under the name Ultrasil® CA-1 Silicone (Dimethicone PEG-7 Phthalate) and Ultrasil® CA-2 Silicone (Dimethicone PEG-7 Succinate).

CDI Linker

In particular, embodiments of the CDI linker of the film forming composition comprise
an organic polymer of Formula II which is a polymer with in-chain carbodiimide groups and may be linear or branched, preferably linear. Alternatively, the CDI linker may comprise an organic polymer of Formula X which is a polymer with pendant single carbodiimide groups and may have a linear or branched backbone, preferably a linear backbone.

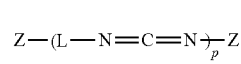

Formula II

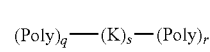

Formula X

For Formula II, p is an integer of at least 2. In many instances, L may be the organic group of an organic diisocyanate may be converted to the polycarbodiimide of Formula II. In other instances, L may be an oligomeric or polymeric moiety terminated by isocyanate groups. This formational understanding shows that L may be an organic CDI linker group comprising a saturated aliphatic divalent radical, an aromatic divalent radical or an alkylaromatic divalent radical or a polymer or oligomeric divalent radical with repeating olefinic, carbonate, ester, ether, amide, urethane or urea linkages. Preferably, L is a saturated aliphatic divalent radical, an aromatic divalent radical or an alkylaromatic divalent radical.

For Formula X, each Poly is an organic polymer segment of amide, urea, ester, olefinic, imine monomeric residues. Poly may be based upon a C3 to C6 alkane diamine and a C4-C10 alkane dicarboxylic acid or C4-C10 alkane diisocyanate, or an ester monomeric residue based upon a C3-C6 alkane diol and a C4-C10 alkane dicarboxylic acid and the designators q and r each being an integer of at least 2. Group K provides the pendant carbodiimide group and s is an integer of at least 2. When s is 2 or greater, the resulting multiple K groups are randomly distributed along the Poly backbone including at the termini. Group K comprises Formula XI

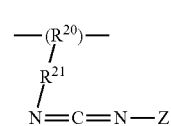

Formula XI

For Formula XI, $R^{20}$ is a C3 to C6 alkylenyl residue and $R^{21}$ is a C3-C6 alkylenyl residue.

For Formulas II and XI, Z may be a non-reactive or reactive terminal group of the polycarbodiimide. As a reactive terminal group, Z may be an —$(CH_2)_n$—$Si(OR)_3$ in which R is methyl or ethyl and n is an integer of 3 to 6. As a non-reactive terminal group, Z may be a saturated aliphatic monovalent radical, an aromatic monovalent radical or an alkylaromatic monovalent radical.

A preferred CDI linker is Formula II in which L is a saturated aliphatic divalent radical selected from linear or branched or cyclic alkylenyl of 2 to 20 carbons, an aromatic divalent radical selected from benzene or diphenyl, or an alkylaromatic divalent radical selected from p-dimethylenylphenyl or methylenyldiphenyl.

Another preferred CDI linker is Formula II in which L is a saturated alkylenyl divalent radical of 2 to 6 carbons.

Another preferred CDI linker is Formula II in which L is a residue of toluene, diphenylmethane, phenyl, dicyclohexyl methane, methyl-3,5,5-trimethylcyclohexane, hexane, cyclohexane, norbornane. These L residues are derived from the corresponding diisocyanate compounds.

A more preferred CDI linker is Formula II in which L is dicyclohexylmethane, methyl-3,5,5-trimethylcyclohexane (isophorone) or hexane.

For Formula II and Formula X, a preferred a nonreactive group for Z is a saturated aliphatic monovalent radical selected from linear or branched or cyclic alkyl of 2 to 20 carbons, an aromatic monovalent radical selected from benzene or diphenyl, or an alkylaromatic monovalent radical selected from p-dimethylenylphenyl or methylenyldiphenyl.

A preferred CDI linker as Formula X provides Poly is a polyamide or polyurea and the number of pendant carbodiimide K groups designated by being from 2 to 50, preferably 2 to 10, more preferably 2 to 5.

A method according to any of the preceding statements wherein the CDI linker is Formula X, $R^{20}$ and $R^{21}$ are each butylenyl or hexylenyl, and Z is butyl or hexyl A preferred nonreactive group of Z for Formulas II and X is butane or hexane.

The molecular size of a CDI linker of Formula II and of Formula X is determined by the number of carbodiimide groups and the size of L for Formula II and Poly for Formula X. For both of Formulas II and X, the preferred number of carbodiimide groups designated by p and k respectively is from 2 to 100, preferably from 2 to 50, more preferably from 2 to 10, most preferably 2 to 5. The foregoing preferred L groups (non-polymeric L groups for Formula II) provide the molecular size for these preferred versions of Formula II. For Formula X, the preferred Poly is polyamide formed of hexane diamine and adipic acid with the pendant K groups formed from 3-aminopropyl-1,6-hexane diamine. Based upon factors such as but not limited to the number of L groups, the size of Poly and the number of carbodiimide groups the weight average molecular weight of the CDI linker may range from 0.5 KDa to about 500 KDa, preferably about 0.5 KDa to about 400 KDa, more preferably about 0.5 KDa to about 10 KDa, most preferably about 0.5 KDa to about 3 KDa to 5 KDa.

The CDI binder and CDI linker molar concentrations and their relative level of functional groups in the film forming composition deliver a ratio of carboxylic acid to carbodiimide groups. In some embodiments of the film forming composition, the CDI binder provides a number of carboxylic acid groups equal to the number of carbodiimide of the CDI linker. In preferred embodiments of the film forming composition, the CDI linker provides an excess number of carbodiimide groups relative to the number of carboxylic acid groups of the CDI binder. This ratio enables carbodiimide addition of the CDI linker with the amine groups of the small molecule of the pretreatment composition. In more preferred embodiments of the film forming composition, the ratio of CDI linker carbodiimide groups to CDI binder carboxylic acid groups may range from about 50:1 to 1.2:1, preferably about 30:1 to 2:1, more preferably about 25:1 to 2.5:1, especially more preferably about 20:1 to about 3:1, most preferably about 20:1 to about 10:1.

Pre-Treatment Composition

The significant remanence, wear-fastness and resistance to environmental attack of the coating on keratin fibers according to aspects of the invention may be developed through interaction between any one or more of the film forming compositions and the pre-treatment composition. The interaction is the complexation and cooperation of interlayer hydrogen bonding, dipolar interaction, molecular intertwining and for the film forming compositions, the covalent crosslinking between and among the pretreatment composition small molecule layer laid down on the keratin fibers and the overlaid films of one or more of the film forming compositions. This aspect according to the invention is believed to produce at least in large part qualities and characteristics of the coating on the keratin fibers. For this reason, incorporation of the pre-treatment composition into the dressing of keratin fibers according to the invention is a preferred aspect of the invention.

The embodiments of the pre-treatment composition combine with embodiments of the combination of the first and second components of the film forming composition to meld together (e.g., blend, combine, unite together as one) these components into a coating on keratin fibers that displays significant remanence. Embodiments of the substantive feature of the pre-treatment composition are directed to molecules comprising silicon compounds and organosilicon compounds having alkoxysilyl groups and optional organoamine groups.

The pretreatment composition according to the invention comprises one or more alkoxysilanes. The term Organosilicon Compound with at least one alkoxysilyl group and optionally with at least one organoamine group hereinafter and for claim interpretation means any one or more of the alkoxysilanes, silicon compounds and organosilicon compounds with alkoxysilyl groups alone and with alkoxysilyl and organoamine groups as delineated as formulas of compounds, species and groups of compounds in the following discussion of the pretreatment composition. The alkoxysilanes present in the composition according to the invention are preferably chosen from organosilanes comprising one, two or three silicon atoms, preferably one or two silicon atoms and optionally with one or more organoamine groups.

Organic silicon compounds, alternatively called organosilicon compounds, are compounds which either have a direct silicon-carbon bond (Si—C) or in which the carbon is bonded to the silicon atom via an oxygen, nitrogen, or sulfur atom. The organic silicon compounds of the present disclosure are compounds containing one to three silicon atoms. Organic silicon compounds preferably contain one or two silicon atoms.

According to IUPAC rules, the term silane chemical compounds based on a silicon skeleton and hydrogen. In organic silanes, the hydrogen atoms are completely or partially replaced by organic groups such as (substituted) alkyl groups and/or alkoxy groups. In organic silanes, some of the hydrogen atoms may also be replaced by hydroxy groups.

A particularly preferred method as contemplated herein the pretreatment composition comprises (a) at least one organic silicon compound selected from silanes having one, two or three silicon atoms, the organic silicon compound preferably comprising one or more basic chemical functions and one or more hydroxyl groups or hydrolysable groups per molecule.

The small molecule incorporating a basic group may be, for example, an amino group, an alkylamino group or a dialkylamino group, which is preferably connected to a silicon atom via a linker. The basic group is preferably an amino group, a C1-C6 alkylamino group or a di-(C1-C6) alkylamino group.

The hydrolysable group(s) is (are) preferably a $C_1$-$C_6$ alkoxy group, especially an ethoxy group or a methoxy group. It is preferred when the hydrolysable group is directly bonded to the silicon atom. For example, if the hydrolysable group is an ethoxy group, the organic silicon compound preferably contains a structural unit R'R''R'''Si—O—$CH_2$—$CH_3$. The residues R', R' and R''' represent the three remaining free valences of the silicon atom.

The alkoxysilanes present in the composition according to the invention may comprise two or more hydrolysable or hydroxyl groups per molecule. The hydrolysable groups are preferably alkoxy, aryloxy or halogen groups. They may optionally comprise other chemical functions, such as salified or non-salified amine, salified or non-salified carboxylic acid, salified or non-salified sulfonic acid, salified or non-salified phosphoric acid, salified or non-salified sulfuric acid, and aldehyde, polyalcohol or polyether functions. Preferably, the alkoxysilanes of the invention comprise one or more amine or aldehyde functions. Even more preferably, the alkoxysilanes of the invention comprise one or more amine functions.

When the alkoxysilane present in the composition according to the invention comprises one or more amine functions, they are preferably primary amines (—NH2) and/or secondary amines (—NHR).

According to one particular embodiment, the alkoxysilane(s) present in the composition according to the invention are chosen from the compounds of formula (I):

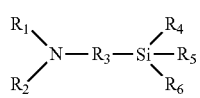
(I)

in which: R4 represents a halogen or a group ORa or R1a; R5 represents a halogen or a group ORb or R2a; R6 represents a halogen or a group ORc or R3a; R1 and R2, represent, independently of each other, a hydrogen atom, a saturated or unsaturated, linear or branched hydrocarbon-based group, optionally substituted with an amine function, which itself may bear a substitution with a saturated or unsaturated, linear or branched hydrocarbon-based group, possibly bearing an amine function, preferably R1 or R2 necessarily denoting a hydrogen atom, R3, Ra, Rb, Rc, R1a, R2a and R3a represent, independently of each other, a saturated or unsaturated, linear or branched hydrocarbon-based group, optionally bearing additional chemical groups such as acid or amine groups, Ra, Rb and Rc also possibly denoting hydrogen, and at least two of the groups R4, R5 and R6 being other than groups R1a, R2a and R3a, and preferably at least two of the groups Ra, Rb and Rc being other than hydrogen.

Preferably, the groups R1, R2, Ra, R1a, R2a, R3a, Rb and Rc are chosen from C1-C12 alkyl, C5-C14 aryl, (C1-C8) alkyl(C5-C14)aryl and (C5-C14)aryl(C1-C8)alkyl radicals.

Preferably, the group R3 is chosen from C1-C12 alkylene radicals, optionally substituted with an amino, C5-C14 arylene, (C1-C8)alkylene(C5-C14)arylene or (C5-C14) arylene(C1-C8)alkylene group.

According to one particular embodiment, the alkoxysilane(s) corresponding to formula (I) are preferably 3-aminopropyltriethoxysilane, 3-aminopropylmethyldiethoxysilane, N-(2-aminoethyl)-3-aminopropyltriethoxysilane and 3-(2-aminoethylamino)propylmethyldiethoxysilane.

According to another particular embodiment, the alkoxysilane(s) used according to the invention are chosen from the compounds of formula (XX):

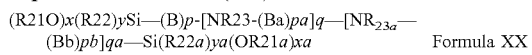   Formula XX in which: R21, R22, R21a and R22a represent, independently of each other, a saturated or unsaturated, linear or branched hydrocarbon-based chain, optionally containing one or more heteroatoms, optionally interrupted or substituted with one or more groups chosen from ether, ester, amine, amide, carboxyl, hydroxyl and carbonyl groups, x is an integer ranging from 1 to 3, y=3-x, xa is an integer ranging from 1 to 3, ya=3-xa, p=0 or 1, pa=0 or 1, pb=0 or 1, q=0 or 1, qa=0 or 1, it being understood that at least q or qa is other than zero, B, Ba and Bb each independently represent a linear or branched divalent C1-C20 alkylene radical.

R23 and R23a each independently represent a hydrogen atom or a saturated or unsaturated, linear or branched hydrocarbon-based chain, optionally containing one or more heteroatoms, optionally interrupted or substituted with one or more ether, C1-C20 alcohol ester, amine, carboxyl, C6-C30 aryl, hydroxyl or carbonyl groups, or a heterocyclic or non-heterocyclic aromatic ring, optionally substituted with one or more C1-C20 alcohol ester, amine, amide, carboxyl, hydroxyl, carbonyl or acyl groups.

Preferably, R23 and R23a represent a hydrogen atom.

As explained previously, R21, R22, R21a and R22a each independently represent a hydrocarbon-based chain. The term "hydrocarbon-based chain" preferably means a chain comprising from 1 to 30 and preferably 1 to 10 carbon atoms.

Preferably, R21=R21a; R22=R22a; x=xa; y=ya; p=pa; B=Ba; q=1 and qa=0.

The alkoxysilane(s) of formula (XX) may also have the following characteristics, taken alone or in combination: R21, R22, R21a and R22a, which may be identical or different, represent a C1-C4 alkyl, p=pa=1; B and Ba, which may be identical or different, represent a linear C1-C4 alkylene.

Particularly good results could be obtained if the agent as contemplated herein (a) contains at least one organic silicon compound of formula (I) and/or (II).

The compounds of formulae (I) and (II) are organic silicon compounds selected from silanes having one, two or three silicon atoms, the organic silicon compound comprising one or more hydroxyl groups and/or hydrolysable groups per molecule.

In another very particularly preferred embodiment, a process as contemplated herein an agent (a) is applied to the keratinous material (or human hair), the agent (a) comprising at least one organic silicon compound (a) of the formula (I) and/or (II), $R_1R_2N$-L-$Si(OR_3)_a(R_4)_b$   Formula I where R₁, R₂ independently represent a hydrogen atom or a C1-C6 alkyl group, L is a linear or branched divalent C1-C20 alkylene group, R3 represents a hydrogen atom or a C1-C6 alkyl group R4 represents a C1-C6 alkyl group a, stands for an integer from 1 to 3, and b stands for the integer 3–a (i.e., 3 minus the value of a), $$(R5O)_c(R6)_aSi\text{-}(A)_e[NR7\text{-}(A')]_f\text{—}[O\text{-}(A'')]_g\text{-}[NR8\text{-}(A''')]_h\text{—}Si\text{—}(R6')_{d'}(OR5')_{c'} \qquad \text{Formula II}$$

where

R5, R5', R5" independently represent a hydrogen atom or a C1-C6 alkyl group,

R6, R6' and R6" independently represent a C1-C6 alkyl group,

A, A', A", A'" and A"" independently of one another represent a linear or branched divalent C1-C20 alkylene group, R7 and R5 independently represent a hydrogen atom, a C1-C6 alkyl group, a hydroxy C1-C6 alkyl group, a C2-C6 alkenyl group, an amino C1-C6 alkyl group or a group of formula (III), $$-(A'''')\text{—}Si(R_6'')_{d''}(OR_5'')_{c''} \qquad (III),$$

c, stands for an integer from 1 to 3, d stands for the integer 3–c, c' stands for an integer from 1 to 3, d' stands for the integer 3–c', c" stands for an integer from 1 to 3, d" stands for the integer 3–c", e stands for 0 or 1, f stands for 0 or 1, g stands for 0 or 1, h stands for 0 or 1, provided that at least one of e, f, g, and h is different from 0.

The substituents R1, R2, R3, R4, R5, R5', R5", R6, R6', R6", R7, R8, L, A, A', A", A'" and A"" in the compounds of formula (I) and (II) are explained below as examples: Examples of a C1-C6 alkyl group are the groups methyl, ethyl, propyl, isopropyl, n-butyl, s-butyl, and t-butyl, n-pentyl and n-hexyl. Propyl, ethyl, and methyl are preferred alkyl radicals. Examples of a C2-C6 alkenyl group are vinyl, allyl, but-2-enyl, but-3-enyl and isobutenyl, preferred C2-C6 alkenyl radicals are vinyl and allyl. Preferred examples of a hydroxy C1-C6 alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino C1-C6 alkyl group are the aminomethyl group, the 2-aminoethyl group, the 3-aminopropyl group. The 2-aminoethyl group is particularly preferred. Examples of a linear divalent C1-C20 alkylene group include the methylene group (—CH2), the ethylene group (—CH2-CH2-), the propylene group (—CH2-CH2-CH2-) and the butylene group (—CH2-CH2-CH2-CH2-). The propylene group (—CH2-CH2-CH2-) is particularly preferred. From a chain length of 3 C atoms, divalent alkylene groups can also be branched. Examples of branched divalent $C_2$-$C_{20}$ alkylene groups are (—CH2-CH(CH3)-) and (—CH2-CH(CH3)-CH2-).

In the organic silicon compounds of the formula (I)

$$R1R2N\text{-}L\text{-}Si(OR3)_a(R4)_b \qquad (I)$$

the radicals R1 and R2 independently of one another represent a hydrogen atom or a C1-C6 alkyl group. In particular, the radicals R1 and R2 both represent a hydrogen atom.

In the middle part of the organic silicon compound is the structural unit or the linker -L- which stands for a linear or branched, divalent C1-C20 alkylene group.

Preferably -L- stands for a linear, divalent C1-C20 alkylene group. Further preferably -L- stands for a linear divalent C1-C6 alkylene group. Particularly preferred -L- stands for a methylene group (—CH2-), an ethylene group (—CH2-CH2-), propylene group (—CH2-CH2-CH2-) or butylene (—CH2-CH2-CH2-CH2-). L stands for a propylene group (—CH2-CH2-CH2-).

The organic silicon compounds of formula (I)

$$R1R2N\text{-}L\text{-}Si(OR3)_a(R4)_b \qquad (I)$$

one end of each carries the silicon-containing group —Si(OR3)a(R4)b.

In the terminal structural unit —Si(OR3)a(R4)b, R3 is hydrogen or C1-C6 alkyl group, and R4 is C1-C6 alkyl group. R3 and R4 independently of each other represent a methyl group or an ethyl group. Here a stands for an integer from 1 to 3, and b stands for the integer 3–a. If a stands for the number 3, then b is equal to 0. If a stands for the number 2, then b is equal to 1. If a stands for the number 1, then b is equal to 2.

Colors with the best wash fastness values could be obtained if the pretreatment agent contains at least one organic silicon compound corresponding to formula (I): in which R3, R4 independently of one another represent a methyl group or an ethyl group.

Furthermore, color with the best wash fastness properties could be obtained if the agent as contemplated herein contains at least one organic silicon compound of formula (I) in which the radical a represents the number 3. In this case the rest b stands for the number 0.

In another preferred embodiment, an agent as contemplated herein contains (a) at least one organic silicon compound of formula (I), where R3, R4 independently of one another represent a methyl group or an ethyl group and a stands for the number 3 and b stands for the number 0.

In another preferred embodiment, a process as contemplated herein the agent (a) contains at least one organic silicon compound of formula (I)

$$R1R2N\text{-}L\text{-}Si(OR3)_a(R4)_b \qquad (I),$$

where R1, R2 both represent a hydrogen atom, and

L represents a linear, divalent C1-C6-alkylene group, preferably a propylene group (—CH2-CH2-CH2-) or an ethylene group (—CH2-CH2-), R3 represents a hydrogen atom, an ethyl group, or a methyl group, R4 represents a methyl group or an ethyl group, a stands for the number 3 and b stands for the number 0.

Organic silicon compounds of the formula (I) which are particularly suitable for solving the problem as contemplated herein are as follows.

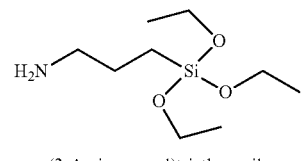

-(3-Aminopropyl)triethoxysilan

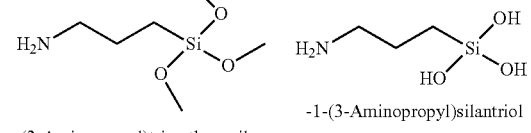

-(3-Aminopropyl)trimethoxysilane

-1-(3-Aminopropyl)silantriol

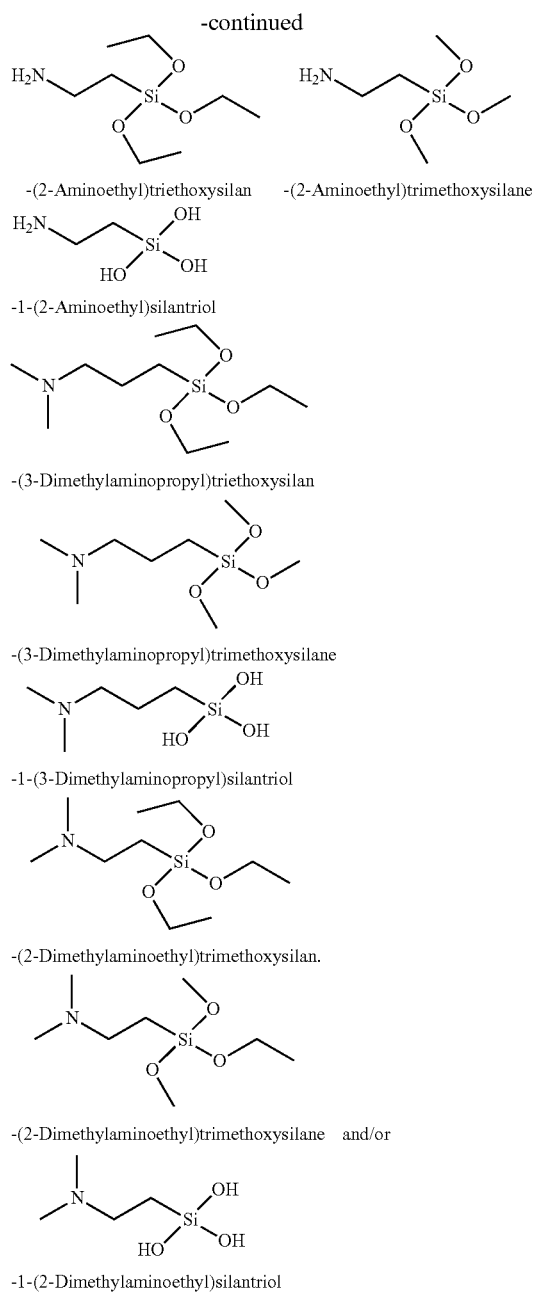

-(2-Aminoethyl)triethoxysilan
-(2-Aminoethyl)trimethoxysilane
-1-(2-Aminoethyl)silantriol
-(3-Dimethylaminopropyl)triethoxysilan
-(3-Dimethylaminopropyl)trimethoxysilane
-1-(3-Dimethylaminopropyl)silantriol
-(2-Dimethylaminoethyl)trimethoxysilan.
-(2-Dimethylaminoethyl)trimethoxysilane and/or
-1-(2-Dimethylaminoethyl)silantriol In a further preferred embodiment, a process as contemplated herein the agent (a) comprises at least one organic silicon compound of formula (I) selected from the group including (3-Aminopropyl)triethoxysilane, (3-Aminopropyl)trimethoxysilane, 1-(3-Aminopropyl) silantriol, (2-Aminoethyl)triethoxysilane, (2-Aminoethyl)trimethoxysilane 1-(2-Aminoethyl)silantriol, (3-Dimethylaminopropyl)triethoxysilane, (3-Dimethylaminopropyl)trimethoxysilane, 1-(3-Dimethylaminopropyl)silantriol (2-Dimethylaminoethyl)triethoxysilane, (2-Dimethylaminoethyl)trimethoxysilane and/or 1-(2-Dimethylaminoethyl)silantriol.

The organic silicon compound of formula (I) is commercially available. (3-aminopropyl)trimethoxysilane, for example, can be purchased from Sigma-Aldrich. Also (3-aminopropyl)triethoxysilane is commercially available from Sigma-Aldrich.

In a further version, the present disclosure contains at least one organic silicon compound of formula (II)

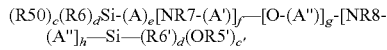

II

The organosilicon compounds of formula (II) as contemplated herein each carry the silicon-containing groups $(R5O)_c(R6)_d Si$— and —$Si(R6')_{d'}(OR5')_{c'}$ at both ends.

In the central part of the molecule of formula (II) there are the groups -$(A)_e$- and —$[NR7-(A')]_f$- and $[O-(A'')]_{g''}$- and —$[NR8-(A''')]_h$-. Here, each of the radicals e, f, g, and h can independently of one another stand for the number 0 or 1, with the proviso that at least one of the radicals e, f, g, and h is different from 0. In other words, an organic silicon compound of formula (II) as contemplated herein contains at least one grouping from the group including -(A)- and —[NR7-(A')]- and —[O-(A'')]- and —[NR8-(A''')]-.

In the two terminal structural units $(R5O)_c(R6)_d Si$— and —$Si(R6')_{d'}(OR5')_{c'}$, the radicals R5, R5', R5'' independently of one another represent a hydrogen atom or a C1-C6 alkyl group. The radicals R6, R6' and R6'' independently represent a C1-C6 alkyl group.

Here a stands for an integer from 1 to 3, and d stands for the integer 3−c. If c stands for the number 3, then d is equal to 0. If c stands for the number 2, then d is equal to 1. If c stands for the number 1, then d is equal to 2. Analogously c' stands for a whole number from 1 to 3, and d' stands for the whole number 3−c'. If c' stands for the number 3, then d' is 0. If c' stands for the number 2, then d' is 1. If c' stands for the number 1, then d' is 2.

Coloration with the best wash fastness values could be obtained if the residues c and c' both stand for the number 3. In this case d and d' both stand for the number 0.

In another preferred embodiment, a process as contemplated herein the agent (a) contains at least one organic silicon compound of formula (II),

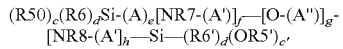

II where R5 and R5' independently represent a methyl group or an ethyl group, c and c' both stand for the number 3 and d and d' both stand for the number 0.

If c and c' are both the number 3 and d and d' are both the number 0, the organic silicon compound of the present disclosure corresponds to formula (IIa)

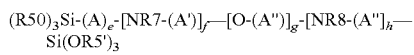

IIa

The radicals e, f, g, and h can independently stand for the number 0 or 1, whereby at least one radical from e, f, g, and h is different from zero. The abbreviations e, f, g, and h thus define which of the groupings -$(A)_e$- and —$[NR2-(A')]_f$- and —$[O-(A'')]_g$ and —$[NR8-(A''')]_h$- are in the middle part of the organic silicon compound of formula (II).

In this context, the presence of certain groupings has proved to be particularly beneficial in terms of increasing washability. Particularly good results were obtained when at least two of the residues e, f, g, and h stand for the number 1. Especially preferred e and f both stand for the number 1. Furthermore, g and h both stand for the number 0.

If e and f both stand for the number 1 and g and h both stand for the number 0, the organic silicon compound as contemplated herein corresponds to formula (IIb)

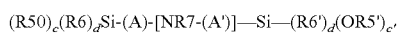

IIb

The radicals A, A', A'', A''' and A'''' independently represent a linear or branched divalent C1-C20 alkylene group. Preferably the radicals A, A', A'', A''' and A'''' independently of one another represent a linear, divalent C1-C20 alkylene group. Further preferably the radicals A, A', A", A'" and A"" independently represent a linear divalent C1-C6 alkylene group. In particular, the radicals A, A', A", A'" and A"" independently of one another represent a methylene group (—CH2-), an ethylene group (—CH2-CH2-), a propylene group (—CH2-CH2-CH2-) or a butylene group (—CH2-CH2-CH2-CH2-). In particular, the residues A, A', A", A'" and A"" stand for a propylene group (—CH2-CH2CH2-).

If the radical f represents the number 1, then the organic silicon compound of formula (II) as contemplated herein contains a structural grouping —[NR7-(A')]-. If the radical f represents the number 1, then the organic silicon compound of formula (II) as contemplated herein contains a structural grouping —[NR8-(A'")]-.

Wherein R7 and R8 independently represent a hydrogen atom, a C1-C6 alkyl group, a hydroxy-C1-C6 alkyl group, a C2-C6 alkenyl group, an amino-C1-C6 alkyl group or a group of the formula (III)

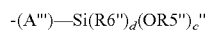

preferably the radicals R7 and R8 independently of one another represent a hydrogen atom, a methyl group, a 2-hydroxyethyl group, a 2-alkenyl group, a 2-aminoethyl group or a grouping of the formula (III).

If the radical f represents the number 1 and the radical h represents the number 0, the organic silicon compound as contemplated herein contains the grouping [NR7-(A')] but not the grouping —[NR8-(A'")] If the radical R7 now stands for a grouping of the formula (III), the pretreatment agent (a) contains an organic silicon compound with 3 reactive silane groups.

In another preferred embodiment, a process as contemplated herein the agent (a) contains at least one organic silicon compound of formula (II),

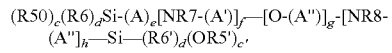

where e and f both stand for the number 1, g and h both stand for the number 0, A and A' independently represent a linear, divalent C1-C6 alkylene group and R7 represents a hydrogen atom, a methyl group, a 2-hydroxyethyl group, a 2-alkenyl group, a 2-aminoethyl group or a group of formula (III).

In a further preferred embodiment, a process as contemplated herein the agent (a) contains at least one organic silicon compound of the formula (II), where e and f both stand for the number 1, g and h both stand for the number 0, A and A' independently of one another represent a methylene group (—$CH_2$—), an ethylene group (—$CH_2$—$CH_2$—) or a propylene group (—$CH_2$—$CH_2$—$CH_2$), and R7 represents a hydrogen atom, a methyl group, a 2-hydroxyethyl group, a 2-alkenyl group, a 2-aminoethyl group or a group of formula (III).

Organic silicon compounds of the formula (II) which are well suited for solving the problem as contemplated herein are

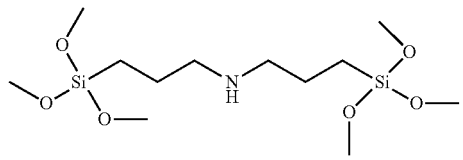

-3-(trimethoxysilyl)-N-[3-(trimethoxysilyl)propyl]-1-propanamine

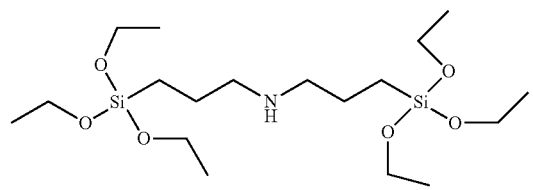

-3-(Triethoxysilyl)-N-[3-(triethoxysilyl)propyl]-1-propanamine

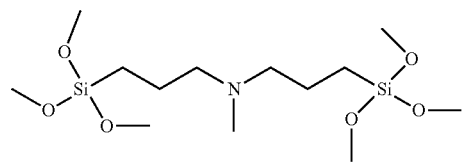

-N-methyl-3-(trimethoxysilyl)-N-[3-(trimethoxysilyl)propyl]-1-propanamine

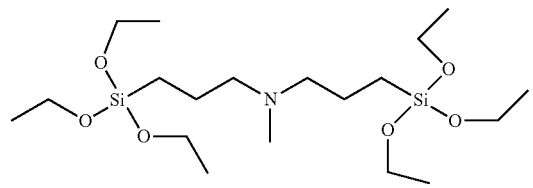

-N-methyl-3-(triethoxysilyl)-N-[3-(triethoxysilyl)propyl]-1-propanamine

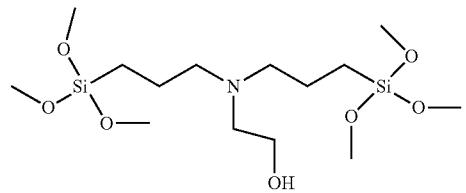

-2-[Bis[3-(trimethoxysilyl)propyl]amino]-ethanol

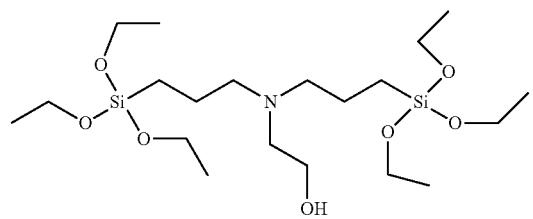

-2-[bis[3-(triethoxysilyl)propyl]amino]-ethanol

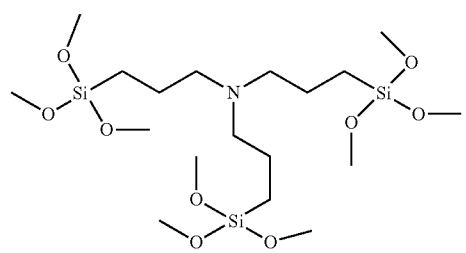

-3-(Trimethoxysilyl)-N,N-bis[3-(trimethoxysilyl)propyl]-1-propanamine

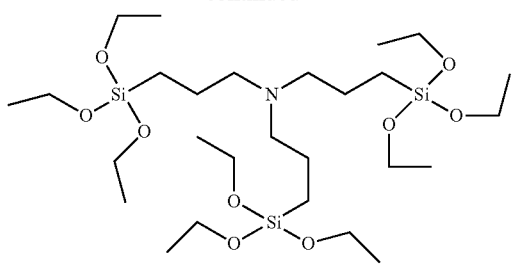

-3-(Triethoxysilyl)-N,N-bis[3-(triethoxysilyl)propyl]-1-propanamine

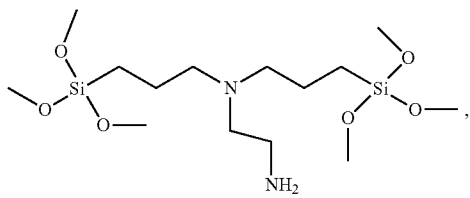

-N1,N1-Bis[3-(trimethoxysilyl)propyl]-1,2-ethanediamine

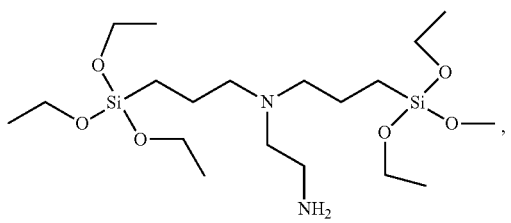

-N1,N1-Bis[3-(triethoxysilyl)propyl]-1,2-ethanediamine

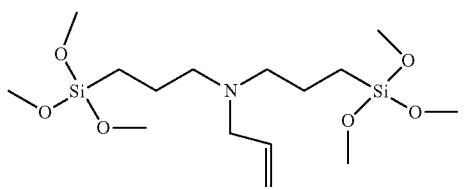

-N,N-Bis[3-(trimethoxysilyl)propyl]-2-propen-1-amine

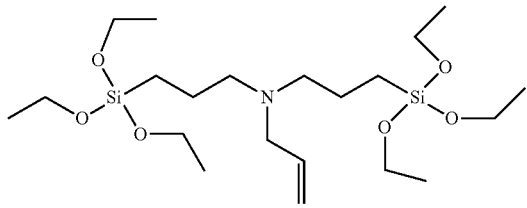

-N,N-Bis[3-(triethoxysilyl)propyl]-2-propen-1-amine

The organic silicon compounds of formula (II) are commercially available.

Bis(trimethoxysilylpropyl)amines with the CAS number 82985-35-1 can be purchased from Sigma-Aldrich. Bis[3-(triethoxysilyl)propyl]amines with the CAS number 13497-18-2 can be purchased from Sigma-Aldrich, for example. N-methyl-3-(trimethoxysilyl)-N-[3-(trimethoxysilyl)propyl]-1-pro-panamine is alternatively referred to as bis(3-trimethoxysilylpropyl)-N-methylamine and can be purchased commercially from Sigma-Aldrich or Fluorochem. 3-(triethoxysilyl)-N,N-bis[3-(triethoxysilyl)propyl]-1-propanamine with the CAS number 18784-74-2 can be purchased for example from Fluorochem or Sigma-Aldrich.

In another preferred embodiment, an agent as contemplated herein contains (a) at least one organic silicon compound of formula (II) selected from the group including
3-(trimethoxysilyl)-N-[3-(trimethoxysilyl)propyl]-1-propanamine,
3-(Triethoxysilyl)-N-[3-(triethoxysilyl)propyl]-1-propanamine,
N-methyl-3-(trimethoxysilyl)-N-[3-(trimethoxysilyl)propyl]-1-propanamine,
N-Methyl-3-(triethoxysilyl)-N-[3-(triethoxysilyl)propyl]-1-propanamine,
2-[Bis[3-(trimethoxysilyl)propyl]amino]-ethanol,
2-[bis[3-(triethoxysilyl)propyl]amino]ethanol,
3-(Trimethoxysilyl)-N,N-bis[3-(trimethoxysilyl)propyl]-1-propanamine 3-(Triethoxysilyl)-N,N-bis[3-(triethoxysilyl)propyl]-1-propanamine, N1,N1-bis[3-(trimethoxysilyl)propyl]-1,2-ethanediamine,
N1,N1-bis[3-(triethoxysilyl)propyl]-1,2-ethanediamine,
N,N-bis[3-(trimethoxysilyl)propyl]-2-propen-1-amine and/or
N,N-bis[3-(triethoxysilyl)propyl]-2-propen-1-amine.

In further coloring tests, it has also proved to be particularly advantageous if the agent used on the keratinous material in the process as contemplated herein (a) contains at least one organic silicon compound of formula (IV)

$$R_9Si(OR_{10})_k(R_{11})_m \qquad (IV).$$

The compounds of formula (IV) are organic silicon compounds selected from silanes having one, two or three silicon atoms, the organic silicon compound comprising one or more hydroxyl groups and/or hydrolysable groups per molecule.

The organic silicon compound(s) of formula (IV) may also be called a silane of the alkyl-alkoxy-silane or alkyl-hydroxy-silane type, $$R_9Si(OR_{10})_k(R_{11})_m \qquad (IV),$$

where
$R_9$ represents a C1-C12, alkyl group, $R_{10}$ represents a hydrogen atom or a C1-C6 alkyl group, $R_{11}$ represents a C1-C6 alkyl group, k is an integer from 1 to 3, and m stands for the integer 3-k.

In another preferred embodiment, a process as contemplated herein the agent (a) contains at least one organic silicon compound of formula (IV).

$$R_9Si(OR_{10})_k(R_{11})_m \qquad (IV),$$

where
R9 represents a C1-C12, alkyl group, R10 represents a hydrogen atom or a C1-C6 alkyl group, R11 represents a C1-C6 alkyl group, k is an integer from 1 to 3, and m stands for the integer 3-k.

In a further preferred embodiment, a process as contemplated herein the agent (a) contains, in addition to the organic silicon compound(s) of formula (I), at least one further organic silicon compound of formula (IV)

$$R_9Si(OR_{10})_k(R_{11})_m \qquad (IV),$$

where
R9 represents a C1-C12, alkyl group, R10 represents a hydrogen atom or a C1-C6 alkyl group, R11 represents a C1-C6 alkyl group, k is an integer from 1 to 3, and m stands for the integer 3-k.

In a further preferred embodiment, a process as contemplated herein the agent (a) contains, in addition to the organic silicon compound or compounds of the formula (II), at least one further organic silicon compound of the formula (IV)

$$R_9Si(OR_{10})_k(R_{11})_m \qquad (IV),$$

where R9 represents a C1-C12 alkyl group, R10 represents a hydrogen atom or a C1-C6 alkyl group, R11 represents a C1-C6 alkyl group, k is an integer from 1 to 3, and m stands for the integer 3-k.

In a further preferred embodiment, a process as contemplated herein the composition contains (a) in addition to the organic silicon compound(s) of formula (I) and/or (II) at least one further organic silicon compound of formula (IV)

$$R_9Si(OR_{10})_k(R_{11})_m \qquad (IV),$$

where R9 represents a C1-C12, alkyl group, R10 represents a hydrogen atom or a C1-C6 alkyl group, R11 represents a C1-C6 alkyl group, k is an integer from 1 to 3, and m stands for the integer 3-k.

In the organic silicon compounds of formula (IV), the radical R9 represents a C1-C12 alkyl group. This C1-C12, alkyl group is saturated and can be linear or branched. Preferably R9 stands for a linear C1-C.sub.8 alkyl group. Preferably R9 stands for a methyl group, an ethyl group, an n-propyl group, an n-butyl group, an n-pentyl group, an n-hexyl group, an n-octyl group or an n-dodecyl group. Particularly preferred, R9 stands for a methyl group, an ethyl group or an n-octyl group.

In the organic silicon compounds of formula (IV), the radical R10 represents a hydrogen atom or a C1-C6 alkyl group. R10 stands for a methyl group or an ethyl group.

In the organic silicon compounds of formula (IV), the radical Ru represents a C1-C6 alkyl group. R11 stands for a methyl group or an ethyl group.

Furthermore, k stands for a whole number from 1 to 3, and m stands for the whole number 3-k. If k stands for the number 3, then m is equal to 0. If k stands for the number 2, then m is equal to 1. If k stands for the number 1, then m is equal to 2.

Colors with the best wash fastness values could be obtained if an agent (a) were used in the process which contains at least one organic silicon compound of the formula (IV) in which the radical k stands for the number 3. In this case the rest m stands for the number 0.

Organic silicon compounds of the formula (IV) which are particularly suitable for solving the problem as contemplated herein are

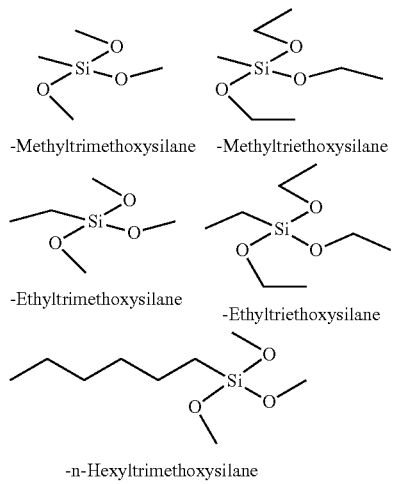

-Methyltrimethoxysilane  -Methyltriethoxysilane

-Ethyltrimethoxysilane
-Ethyltriethoxysilane

-n-Hexyltrimethoxysilane

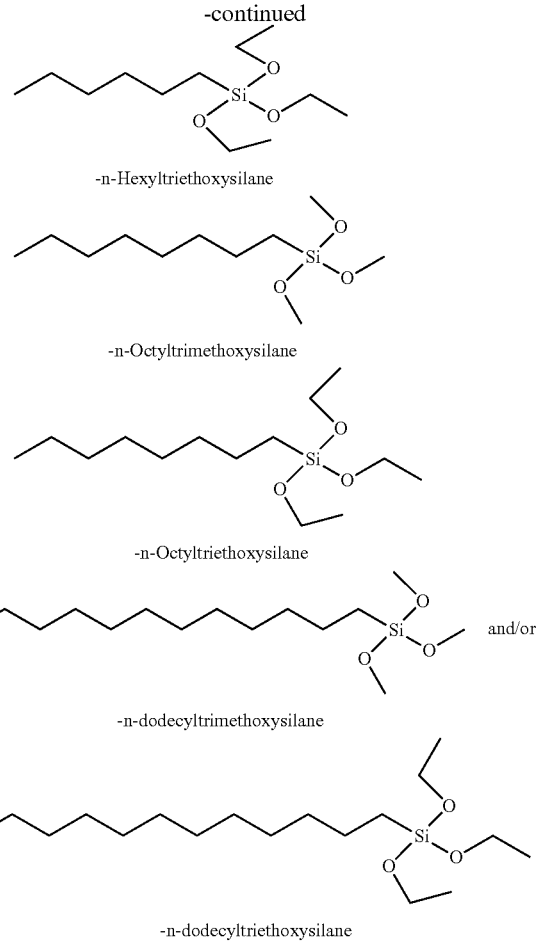

-n-Hexyltriethoxysilane

-n-Octyltrimethoxysilane

-n-Octyltriethoxysilane and/or

-n-dodecyltrimethoxysilane

-n-dodecyltriethoxysilane

In another preferred embodiment, a process as contemplated herein the agent (a) contains at least one organic silicon compound of formula (IV) selected from the group including Methyltrimethoxysilane, Methyltriethoxysilane, Ethyltrimethoxysilane, Ethyltriethoxysilane, Hexyltrimethoxysilane, Hexyltriethoxysilane, Octyltrimethoxysilane, Octyltriethoxysilane, Dodecyltrimethoxysilane and/or Dodecyltriethoxysilane.

In an explicitly particularly preferred embodiment, a process as contemplated herein an agent (a) is applied to the keratinous material which contains at least one organic silicon compound of the formula (I) which is selected from the group including (3-aminopropyl)triethoxysilane and (3-aminopropyl)trimethoxysilane, and additionally contains at least one organic silicone compound of formula (IV) selected from the group including methyltrimethoxysilane, methyltriethoxysilane, ethyltrimethoxysilane and ethyltriethoxysilane.

The organic silicon compounds described above are reactive compounds. In this context, it has been found preferable if the agent (a) as contemplated herein contains—based on the total weight of the agent (a)—one or more organic silicon compounds from the group of silanes having one, two or three silicon atoms in a total amount of the one or more compounds from about 0.1 to about 95.0% by weight, preferably from about 1.0 to about 90.0% by weight and particularly preferably from about 2.0 to about 90% by weight.

In a further preferred embodiment, a process as contemplated herein the agent (a)—based on the total weight of agent (a)—contains one or more organic silicon compounds in a total amount of the one or more compounds from about 0.1 to about 95.0% by weight, preferably from about 1.0 to about 90.0% by weight and particularly preferably from about 2.0 to about 90.0% by weight.

To achieve particularly good coloring results, it is particularly advantageous to use the organic silicon compounds of the formula (I) and/or (II) in certain quantity ranges on average (a). Particularly preferably, the agent (a) contains—based on the total weight of the agent (a)—one or more organic silicon compounds of the formula (I) and/or (II) in a total amount of from about 0.1 to about 60.0% by weight, preferably from about 0.5 to about 55.0% by weight and particularly preferably from about 1.0 to about 55.0% by weight.

In a further preferred embodiment, a process as contemplated herein the agent (a) contains—based on the total weight of the agent (a) one or more organic silicon compounds of the formula (I) and/or (II) in a total amount of from about 0.1 to about 95.0% by weight, preferably from about 0.5 to about 55.0% by weight and particularly preferably from about 1.0 to about 50.0% by weight.

Furthermore, it has proven to be particularly preferred if the organic silicon compound(s) of formula (IV) is (are) also present in certain quantity ranges in average (a). Particularly preferably the agent (a) contains—based on the total weight of agent (a) one or more organic silicon compounds of the formula (IV) in a total amount of from about 0.1 to about 95.0% by weight, preferably from about 2.0 to about 90.0% by weight and particularly preferably from about 3.0 to about 85.0% by weight.

In a further preferred embodiment, a process as contemplated herein the agent (a) contains—based on the total weight of the agent (a) one or more organic silicon compounds of the formula (IV) in a total amount of from about 0.1 to about 95.0% by weight, preferably from about 2.0 to about 90.0% by weight and particularly preferably from about 3.0 to about 85.0% by weight.

In the course of the work leading to this present disclosure it turned out that particularly stable and uniform films could be obtained on the keratin material if the agent (a) contains two structurally different organic silicon compounds.

In another preferred embodiment, a process as contemplated herein the agent (a) contains at least two structurally different organic silicon compounds.

In an explicitly particularly preferred embodiment, a process as contemplated herein an agent (a) is applied to the keratinous material which contains at least one organic silicon compound of the formula (I) which is selected from the group including (3-aminopropyl)triethoxysilane and (3-aminopropyl)trimethoxysilane, and additionally contains at least one organic silicon compound of the formula (IV) which is selected from the group including methyltrimethoxysilane, methyltriethoxysilane, ethyltrimethoxysilane and ethyltriethoxysilane.

In a further preferred embodiment, a process as contemplated herein the agent (a) based on the total weight of agent (a) contains from about 0.5 to about 60.0 weight % of at least one first organic silicon compound selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane (2-dimethylaminoethyl)trimethoxysilane and (2-dimethylaminoethyl)triethoxysilane, and from about 3.0 to about 85.0% by weight of at least one second organic silicon compound selected from the group of methyltrimethoxysilane, methyltriethoxysilane, ethyltrimethoxysilane, ethyltriethoxysilane, octyltrimethoxysilane, octyltriethoxysilane, dodecyltrimethoxysilane and dodecyltriethoxysilane.

In this version, the agent contains (a) one or more organic silicon compounds of a first group in a total amount of from about 0.5 to about 5.0% by weight. The organic silicon compounds of this first group are selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane (2-dimethylaminoethyl)trimethoxysilane and/or (2-dimethylaminoethyl)triethoxysilane.

In this version, the agent contains (a) one or more organic silicon compounds of a second group in a total amount of from about 2 wt % to about 10.0% by weight. The organic silicon compounds of this second group are selected from the group of methyltrimethoxysilane, methyltriethoxysilane, ethyltrimethoxysilane, ethyltriethoxysilane, octyltrimethoxysilane, octyltriethoxysilane, dodecyltrimethoxysilane and/or dodecyltriethoxysilane.

For example, the alkoxysilane(s) are chosen from bis[3-(triethoxysilyl)propyl]amine of formula $(CH3CH2O)_3—Si(CH2)_3NH(CH2)_3Si(OCH2CH3)_3$ sold by the company Fluorochem, bis[trimethoxysilylpropyl]amine of formula $(CH3O)_3—Si(CH2)_3NH(CH2)_3Si(OCH3)_3$3 sold by the company Gelest, bis[methyldiethoxysilylpropyl]amine of formula $(CH3CH2O)_2CH3Si(CH2)_3NH(CH2)_3SiCH3(OCH2CH3)_2$ sold by the company Gelest, and bis[3-trimethoxysilylpropyl]ethylenediamine of formula $(CH3O)_3Si(CH2)_3NH(CH)_2NH(CH2)_3Si(OCH_3)_3$ sold by the company Gelest. Among these compounds, bis[3-(triethoxysilyl)propyl]amine and bis[methyldiethoxysilylpropyl]amine are preferred.

According to another embodiment of the invention, the alkoxysilane(s) are chosen from the compounds of formula (III):

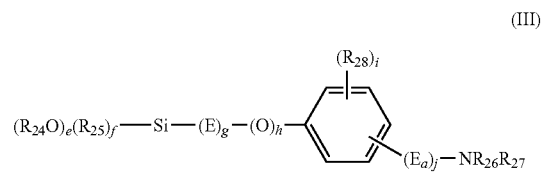

in which: R24 and R25 represent, independently of each other, a saturated or unsaturated, linear or branched hydrocarbon-based chain, optionally containing one or more heteroatoms, optionally interrupted or substituted with one or more groups chosen from ether, ester, amine, amide, carboxyl, hydroxyl and carbonyl groups, e=2 or 3; f=3−e; g=0 or 1; j=0 or 1; E and $E_a$ each independently represent a linear or branched divalent C1-C20 alkylene radical, R26 and R27 each independently represent a hydrogen atom or a saturated or unsaturated, linear or branched hydrocarbon-based chain, optionally containing one or more heteroatoms, optionally interrupted or substituted with one or more ether, C1-C20 alcohol ester, amine, carboxyl, C6-C30 aryl, hydroxyl or carbonyl groups, or a heterocyclic or non-heterocyclic aromatic ring, optionally substituted with one or more C1-C20 alcohol ester, amine, amide, carboxyl, hydroxyl, carbonyl or acyl groups, i is an integer ranging from 0 to 4, h is 0 or 1, the group(s) R28 each independently represent a hydrogen atom or a saturated or unsaturated, linear or branched, preferably C1-C10 hydrocarbon-based chain, optionally containing one or more heteroatoms, optionally interrupted or substituted with one or more ether, C1-C20 alcohol ester, amine, carboxyl, C6-C30 aryl, hydroxyl or carbonyl groups, or a heterocyclic or non-heterocyclic aromatic ring, optionally substituted with one or more C1-C20 alcohol ester, amine, amide, carboxyl, hydroxyl, carbonyl or acyl groups.

As explained previously, R24 and R25 each independently represent a hydrocarbon-based chain. The term "hydrocarbon-based chain" preferably means a chain comprising from 1 to 30 and preferably 1 to 10 carbon atoms.

Similarly, R26 or R27 may represent a hydrocarbon-based chain. In this case, it preferably means a chain comprising from 1 to 30 and preferably 1 to 10 carbon atoms.

Preferably, the aromatic ring comprises from 6 to 30 carbon atoms. Even more preferentially, it denotes an optionally substituted phenyl radical.

The alkoxysilane(s) of formula (III) may have the following characteristics, taken alone or in combination: R24 is a C1-C4 alkyl, e=3, g=j=1; i=h=0, R26 and R27 independently represent hydrogen or a group chosen from C4 alkyl, C1-C4 hydroxyalkyl and C1-C4 aminoalkyl groups.

Preferably, R26 or R27 denote a hydrogen atom.
In particular, the alkoxysilane(s) of formula (III) may be chosen from: 3-(m-aminophenoxy)propyltrimethoxysilane, of formula:

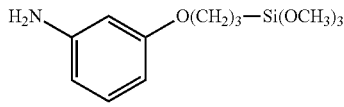

p-aminophenyltrimethoxysilane, of formula:

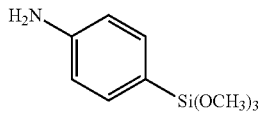

N-(2-aminoethylaminomethyl)phenethyltrimethoxysilane, of formula:

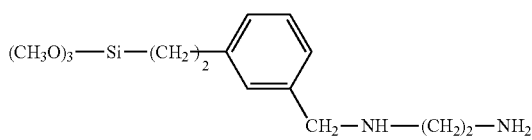

More preferentially, the alkoxysilane(s) that may be used in the compositions according to the present invention correspond to formula (IV):

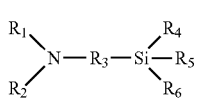

in which: R1 and R2, independently of each other, are chosen from hydrogen and ethyl, propyl and aminoethyl groups; R3 is chosen from ethyl, propyl and methylphenethyl groups; R4, R5 and R6, independently of each other, are chosen from methyl, methoxy and ethoxy groups.

In one variant of the invention, the alkoxysilanes of the invention comprise one or more primary or secondary amine functions.

Preferably, the alkoxysilanes of the invention are chosen from the compounds of formulae (I), (III) and (IV) and more particularly the following compounds: 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane and N-(2-aminoethylaminomethyl)phenethyltrimethoxysilane of formula:

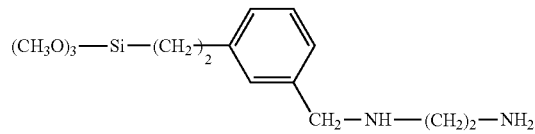

More particularly, the alkoxysilanes of the invention are chosen from the compounds of formula (I), especially 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane and preferably the alkoxysilane is 3-aminopropyltriethoxysilane (APTES).

The alkoxysilane(s) may be present in the cosmetic composition according to the invention in a content ranging from 0.05% to 20%, in particular from 0.1% to 10%, preferably from 0.2% to 5%, relative to the total weight of the composition.

Pigment

The film forming and pretreatment composition embodiments of the present invention make it possible to obtain colored coatings, without substantially altering the keratin fibers. As used herein, the terms "pigment(s) and color body(ies)" are synonyms and cover pigments which generally refer to any particle colorant or amorphous insoluble color material having or containing pigment material that gives keratin fibers color including black and white, such as titanium dioxide that gives only white color to keratin fibers. The pigments are substantially water-insoluble. The pigments, to distinguish from dyes presented in molecular from, are also referred to as pigment microparticles or pigment particles. The terms pigment microparticles and pigment particles are synonymous and are used herein interchangeably. The pigments can be organic, inorganic, or a combination of both. The pigments may be in pure form or coated, for example with a polymer or a dispersant.

Selections, multiple kinds and varying forms of the pigment microparticles as described in the following passages can be incorporated in any of the first, second and third components of the multicomponent composition, or can be incorporated in any two of these components or in all three. Preferably, pigment microparticles can be incorporated in either or both of the first and second components. More preferably, pigment particles can be incorporated in the first component.

The at least one pigment that can be used can be chosen from the organic and/or mineral pigments known in the art, such as those described in Kirk-Othmer's Encyclopedia of Chemical Technology and in Ullmann's Encyclopedia of Industrial Chemistry. The pigments comprised in the microparticles comprising at least one pigment will not substantially diffuse or dissolve into keratin fibers. Instead, the pigment comprised in the microparticles comprising at least one pigment will substantially remain separate from but attached to the keratin fibers.

The at least one pigment can be in the form of powder or of pigmentary paste. It can be coated or uncoated. The at least one pigment can be chosen, for example, from mineral pigments, organic pigments, elemental metal and their oxides, and other metal modifications, lakes, pigments with special effects such as nacres or glitter flakes, and mixtures thereof.

Pigment Shape

The pigment microparticles can have any suitable shape, including substantially spherical. But the pigment microparticles can also be oval, elliptical, tubular, irregular, etc., or even combinations of various shapes. In addition, the pigment microparticles can have two dimensions, length and width/diameter, of similar magnitude. In addition, the pigment microparticles can be micro platelets, i.e. having a thickness that is substantially smaller than the planar dimension. For example, five, ten or even 20 times smaller in thickness than in the planer dimension. In one embodiment with any of the reactive components of the instant invention, the pigments may be surface treated, surface coated or encapsulated.

Pigment Size

The pigments can be present in the composition in undissolved form. Depending on the shape, the pigments can have a D50[vol] particle diameter of from 0.001 micron to 1 micron.

According to an embodiment, the particle size distribution, either relative to the number or volume of the particles, of the pigment microparticles can be at least bi-modal. A bi-modal particle size distribution has two distinct peaks which are spaced relative from, while tri-modal particle size distribution has three distinct peaks. The term "peak" means a local maximum of the distribution curve. The "distance" between two peaks, expressed relative to the particle size, can be at least 0.05 micron, preferably at least 0.1 micron, such as at least 0.2 micron. Providing an at least bi-modal particle size distribution allows to tailor the optical appearance of the colored hair. For example, the scattering properties varies with the particle size so that particles of different size scatter the light into different directions.

Pigments made from metal and metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal. Such pigment microparticles can be platelets, e.g., having a thickness that is substantially smaller than the planar dimension. For example, about five, about 10 or even about 400 times smaller in thickness than in the planer. Such platelets can have a planar dimension less than about 30 nm, but with a thickness less than about 10 micron wide. This includes a ratio of 10000 to 30, or 333. Platelets larger in size, such as 50 microns are even available in this thickness of 10 microns, and so the ratios can even go up to 2000.

The pigment microparticles can be a composite formed by two different types of pigment microparticles. Examples include a composite of a 2-dimensional microparticle and at least one micro spherical particle (microsphere), a composite of different micro spherical particles, and a composite of different 2-dimensional particles. Composite particles formed by 2-dimensional microparticles to which micro spherical particles adhere provide an attractive alternative to a pure mixture of 2-dimensional microparticles and micro spherical particles. For example, a metallic 2-dimensional microparticle can carry one or more micro spherical particle such as one or more organic micro spherical particle. The micro spherical particles attached or bonded to the 2-dimensional microparticle can be formed of the same pigment material or can be formed of different pigment material. Composite microparticles formed of 2-dimensional microparticles and micro spherical particles can provide multiple functionality in one particle such as (metallic) reflectance and dielectric scattering, reflectance and absorption.

The pigment microparticles can be both light scattering and absorbing for wavelengths of visible light. While not wishing to bound by any specific theory, it is believed that such pigments can provide both some visual effect of lightening the hair. Such pigment microparticles can have a D50[num] value between about 50 nm and about 750 nm, between about 100 nm and about 500 nm or between about 150 nm and about 400 nm. Such materials have a refractive index above about 1.5, above about 1.7 or above about 2.0.

According to an embodiment, different pigment microparticles are combined to provide reflective, transmitting and refractive properties of the hair colored with the color composition described herein. A microparticle combination can be a material composite using at least two different pigment materials to form the pigment microparticles. In addition to, or alternating to, the microparticle combination, a mixture of separate pigment microparticles of different type can be used to bring about the desired reflective, transmitting and refractive properties.

The composite pigments, combination of pigments, and mixtures of pigment microparticles eliminate, or at least significantly reduce, hair penetration and scattering by light and thus eliminate the perception of pigment of natural hair color change.

Pigment Concentration

The film forming composition for coloring hair fibers according to the present disclosure comprises microparticles comprising at least one pigment. The film forming composition comprises from about 0.01% to about 40%, about 0.05% to about 35%, about 0.1 to about 25%, or about 0.15% and about 20% pigment(s), by weight of the film forming composition.

Pigment Material

The material of the pigment microparticles can be inorganic or organic. Inorganic-organic mixed pigments are also possible.

According to an embodiment, inorganic pigment(s) may be used. The advantage of inorganic pigment(s) is their excellent resistance to light, weather, and temperature. The inorganic pigment(s) can be of natural origin, and are, for example, derived from material selected from the group consisting of chalk, ochre, umber, green earth, burnt sienna, and graphite. The pigment(s) can preferably be white pigments, such as, for example, titanium dioxide or zinc oxide. The pigment(s) can also be colored pigments, such as, for example, ultramarine or iron oxide red, luster pigments, metal effect pigments, pearlescent pigments, and fluorescent or phosphorescent pigments. The pigment(s) can be selected from the group consisting of metal oxides, hydroxides and oxide hydrates, mixed phase pigments, sulfur-containing silicates, metal sulfides, complex metal cyanides, metal sulfates, chromates and molybdates, alloys, and the metals themselves. The pigment(s) can be selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), Prussian blue (ferric ferrocyanide, CI 77510), carmine (cochineal), zinc sulfide, barium sulfate, zinc oxide, derivatized titanium dioxide, derivatized zinc sulfide, derivatized zinc oxide, and mixtures thereof. The pigment(s) can be selected from the group consisting of iron oxide, titanium dioxide, mica, borosilicate, and combinations thereof. The pigment(s) can comprise an iron oxide ($Fe_2O_3$) pigment. The pigment(s) can comprise a combination of mica and titanium dioxide.

The pigment(s) can be pearlescent and colored pigment(s) and can preferably be based on mica which are coated with a metal oxide or a metal oxychloride, such as titanium dioxide or bismuth oxychloride, and optionally further color-imparting substances, such as iron oxides, Prussian blue, ultramarine, and carmine. The color exhibited by a pigment can be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for color travel pigments that display color shifting effects depending on the viewing angle and are based on either natural mica, $SiO_2$ or calcium aluminum borosilicate flakes, coated with varying layers of $TiO_2$. Pigment(s) from the line KTZ® from Kobo Products, Inc., 3474 So. Clinton Ave., So. Plainfield, USA, are also useful herein, in particular the Surface Treatable KTZ® Pearlescent Pigments from Kobo. Particularly useful are KTZ® FINE WHITE (mica and TiO2) having a D50 particle diameter of 5 to 25 micron and also KTZ® CELESTIAL LUSTER (mica and TiO2, 10 to 60 micron) as well as KTZ® CLASSIC WHITE (mica and TiO2, 10 to 60 micron). Also useful are SynCrystal Sapphire from Eckart Effect Pigments, which is a blue powder comprising platelets of synthetic fluorphlogopite coated with titanium dioxide, ferric ferrocyanide and small amounts of tin oxide. Also useful is SYNCRYSTAL Almond also from Eckart, which is a beige powder with a copper reflection color and is composed of platelets of synthetic fluorphlogopite and coated with titanium dioxide and iron oxides. Also useful is Duocrome® RV 524C from BASF, which provides a two color look via a lustrous red powder with a violet reflection powder due to its composition of mica, titanium dioxide and carmine. The colored pigment(s) can be lightly bright colored pigment(s) and can particularly be white color variations.

The pigment(s) can be organic pigments. The at least one pigment can be an organic pigment. As used herein, the term "organic pigment" means any pigment that satisfies the definition in Ullmann's encyclopedia in the chapter on organic pigments. For instance, the at least one organic pigment can be chosen from nitroso, nitro, azo, xanthene, quinoline, anthraquinone, phthalocyanin, copper phthalocyanin, copper hexadecachlorophthalocyanine, 2-[(2-Methoxy-4-nitrophenyl)azo]-N-(2-methoxyphenyl)-3-oxobutyramide, metal-complex, isoindolinone, isoindoline, quinacridone, perinone, perylene, diketopyrrolopyrrole, thioindigo, dioxazine, triphenylmethane, dimethylquinacridone and quinophthalone compounds, Azo-dyes, Nonionic azo dyes, Anionic Azo dyes, Cationic azo dyes, Complex forming azo dye, aza annulene dyes, aza analogue of diarylmethane dyes, aza annulene dyes, Nitro-dyes and their pigments, Carbonyl dyes and their pigments (for example, Anthrachinon dyes, indigo), Sulfur dyes, Florescence dyes, Anthracene or Insoluble alkali or earth metal acid dyes. Or the pigment can be at least one of uncolored and UV absorbing.

The organic pigment(s) can be selected from the group consisting of natural pigments sepia, gamboge, bone charcoal, Cassel brown, indigo, chlorophyll and other plant pigments. The synthetic organic pigments can be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof. A particularly preferred pigment is 7-Bis(1,3-dichloropropan-2-yl)benzo[lmn][3,8]phenanthrolin-1,3,6,8(2H,7H)-tetraon.

The pigment(s) used in the color composition can include at least two different pigments selected from the above pigment group or can include at least three different pigments selected from the above pigment group. According to an embodiment, the pigment(s) used in the color composition can include at least one yellow pigment selected from the yellow pigment group consisting of: a Pigment Yellow 83 (CI 21108), CAS #5567-15-7, Pigment Yellow 155 (C.I. 200310), (CAS: 68516-73-4), Pigment Yellow 180 (C.I. 21290), (CAS: 77804-81-0).

In addition to the at least one yellow pigment, or alternatively, the pigments(s) used in the color composition can include at least one red pigment selected from the red pigment group consisting of: Pigment Red 5 (CI 12490), (CAS #6410-41-9), Pigment Red 112 (CI 12370), (CAS #6535-46-2), Pigment Red 122 (CI 73915), (CAS #980-26-7).

In addition to the at least one yellow pigment and/or the at least one red pigment, or alternatively, the pigments(s) used in the color composition can include at least one green pigment selected from the green pigment group consisting of: Pigment Green 36, (C.I. 74265), (CAS: 14302-13-7).

In addition to the at least one yellow pigment and/or the at least one red pigment and or the at least one green pigment, or alternatively, the pigments(s) used in the color composition can include at least one blue pigment selected from the blue pigment group consisting of: Pigment Blue 16, (CAS: 424827-05-4), Pigment Blue 60 (C.I. 69800), (CAS: 81-77-6), Pigment Blue 66, (C.I. 73000), (CAS: 482-89-3)

In addition to the at least one yellow pigment and/or the at least one red pigment and/or the at least one green pigment, and/or the at least one blue pigment or alternatively, the pigments(s) used in the color composition can include at least one black pigment selected from the black pigment group consisting of: Pigment Black 6 (C.I. 77266), (CAS 1333-86-4), Pigment Black 7 (C.I. 77266), (CAS 1333-86-4). An additional combination can include aluminium flake with a red, blue, green, yellow or any combination thereof.

The pigment(s) can optionally have a surface zeta potential of ≥+15 Mv, preferably ≥±20 Mv, more preferably ≥±25 Mv. The surface zeta potential can be measured with a zetasizer, for example, a Zetasizer 3000 HS. Surface zeta potential measurements are conducted, for example, according to ISO 13099.

For example, the white or colored organic pigments can be chosen from carmine, carbon black, aniline black, melanin, azo yellow, quinacridone, phthalocyanine blue, sorghum red, the blue pigments codified in the Color Index under the references CI 42090, 69800, 69825, 73000, 74100, and 74160, the yellow pigments codified in the Color Index under the references CI 11680, 11710, 15985, 19140, 20040, 21090, 21100, 21108, 47000, 47005 and 77492.

The green pigments codified in the Color Index under the references CI 61565, 61570, 74265, and 74260, the orange pigments codified in the Color Index under the references CI 11725, 12075, 15510, 45370, and 71105, the red pigments codified in the Color Index under the references CI 12085, 12120, 12370, 12420, 12490, 14700, 15525, 15580, 15585, 15620, 15630, 15800, 15850, 15865, 15880, 17200, 26100, 45380, 45410, 45430, 58000, 73360, 73915, 75470, and 77491 and the pigments obtained by oxidative polymerization of indole or phenolic derivatives.

Non-limiting examples that can also be mentioned include pigmentary pastes of organic pigments, such as the products sold by the company Hoechst under the names: JAUNE COSMENYL IOG: Pigment Yellow 3 (CI 11710); JAUNE COSMENYL G: Pigment Yellow 1 (CI 11680); ORANGE COSMENYL GR: Pigment Orange 43 (CI 71105); ROUGE COSMENYL R: Pigment Red 4 (CI 12085); CARMINE COSMENYL FB: Pigment Red 5 (CI 12490); VIOLET COSMENYL RL: Pigment Violet 23 (CI 51319); BLEU COSMENYL A2R: Pigment Blue 15.1 (CI 74160); VERT COSMENYL GG: Pigment Green 7 (CI 74260); and NOIR COSMENYL R: Pigment Black 7 (CI 77266).

The at least one pigment in accordance with the present disclosure can also be in the form of at least one composite pigment as described in European Patent Publication No. EP 1 184 426 A2. These composite pigments can be, for example, compounds of particles comprising a mineral core, at least one binder for ensuring the binding of the organic pigments to the core, and at least one organic pigment at least partially covering the core.

The at least one pigment in accordance with the present disclosure can be in the form of small undissolved microparticles, which do not diffuse into the hair color, but deposit on the outer wall of the keratin fiber. Suitable color pigments can be of organic and/or inorganic origin. But the pigments can also be inorganic color pigments, given the excellent light, weather and/or temperature resistance thereof.

Inorganic pigments, whether natural or synthetic in origin, include those produced from chalk, red ocher, umbra, green earth, burnt sienna or graphite, for example. Furthermore, it is possible to use black pigments, such as iron oxide black, color pigments such as ultramarine or iron oxide red, and fluorescent or phosphorescent pigments as inorganic color pigments.

Colored metal oxides, metal hydroxides and metal oxide hydrates, mixed phase pigments, sulfurous silicates, silicates, metal sulfides, complex metal cyanides, metal sulfates, metal chromates and/or metal molybdates are particularly suitable. In particular, preferred color pigments are black iron oxide (Cl 77499), yellow iron oxide (Cl 77492), red and brown iron oxide (Cl 77491), manganese violet (Cl 77742), ultramarine (sodium aluminum sulfosilicates, Cl 77007, Pigment Blue 29), chromium oxide hydrate (CI 77289), iron blue (ferric ferrocyanide, CI 77510) and/or carmine (cochineal).

The at least one pigment can also be colored pearlescent pigments. These are usually mica-based and can be coated with one or more metal oxides from the group consisting of titanium dioxide (CI 77891), black iron oxide (CI 77499), yellow iron oxide (CI 77492), red and brown iron oxide (Cl 77491, CI 77499), manganese violet (Cl 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Mica forms part of the phyllosilicates, including muscovite, phlogopite, paragonite, biotite, lepidolite, and margarite. To produce the pearlescent pigments in combination with metal oxides, the mica, primarily muscovite or phlogopite, is coated with a metal oxide.

The at least one pigment can also be at least one mica-based colored pigment, which is coated with one or more metal oxides from the group consisting of titanium dioxide (CI 77891), black iron oxide (CI 77499), yellow iron oxide (CI 77492), red and/or brown iron oxide (Cl 77491, CI 77499), manganese violet (Cl 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

The at least one pigment can also be color pigments commercially available, for example, under the trade names Rona®, Colorona®, Dichrona® and Timiron® from Merck, Ariabel® and Unipure® from Sensient, Prestige® from Eckart Cosmetic Colors, and Sunshine® from Sunstar.

The at least one pigment can also be color pigments bearing the trade name Colorona® are, for example: Colorona Copper, Merck, MICA, Cl 77491 (IRON OXIDES); Colorona Passion Orange, Merck, Mica, Cl 77491 (Iron Oxides), Alumina; Colorona Patina Silver, Merck, MICA, Cl 77499 (IRON OXIDES), Cl 77891 (TITANIUM DIOXIDE); Colorona RY, Merck, Cl 77891 (TITANIUM DIOXIDE), MICA, Cl 75470 (CARMINE); Colorona Oriental Beige, Merck, MICA, Cl 77891 (TITANIUM DIOXIDE), Cl 77491 (IRON OXIDES); Colorona Dark Blue, Merck, MICA, TITANIUM DIOXIDE, FERRIC FERROCYANIDE; Colorona Chameleon, Merck, Cl 77491 (IRON OXIDES), MICA; Colorona Aborigine Amber, Merck, MICA, Cl 77499 (IRON OXIDES), Cl 77891 (TITANIUM DIOXIDE); Colorona Blackstar Blue, Merck, Cl 77499 (IRON OXIDES), MICA; Colorona Patagonian Purple, Merck, MICA, Cl 77491 (IRON OXIDES), Cl 77891 (TITANIUM DIOXIDE), Cl 77510 (FERRIC FERROCYANIDE); Colorona Red Brown, Merck, MICA, Cl 77491 (IRON OXIDES), Cl 77891 (TITANIUM DIOXIDE); Colorona Russet, Merck, Cl 77491 (TITANIUM DIOXIDE), MICA, Cl 77891 (IRON OXIDES); Colorona Imperial Red, Merck, MICA, TITANIUM DIOXIDE (Cl 77891), D&C RED NO. 30 (Cl 73360); Colorona Majestic Green, Merck, Cl 77891 (TITANIUM DIOXIDE), MICA, Cl 77288 (CHROMIUM OXIDE GREENS); Colorona Light Blue, Merck, MICA, TITANIUM DIOXIDE (Cl 77891), FERRIC FERROCYANIDE (Cl 77510); Colorona Red Gold, Merck, MICA, Cl 77891 (TITANIUM DIOXIDE), Cl 77491 (IRON); Colorona Gold Plus MP 25, Merck, MICA, TITANIUM DIOXIDE (Cl 77891), IRON OXIDES (Cl 77491); Colorona Carmine Red, Merck, MICA, TITANIUM DIOXIDE, CARMINE Colorona Blackstar Green, Merck, MICA, Cl 77499 (IRON OXIDES); Colorona Bordeaux, Merck, MICA, Cl 77491 (IRON OXIDES); Colorona Bronze, Merck, MICA, Cl 77491 (IRON OXIDES); Colorona Bronze Fine, Merck, MICA, Cl 77491 (IRON OXIDES); Colorona Fine Gold MP 20, Merck, MICA, Cl 77891 (TITANIUM DIOXIDE), Cl 77491 (IRON OXIDES); Colorona Sienna Fine, Merck, Cl 77491 (IRON OXIDES), MICA Colorona Sienna, Merck, MICA, Cl 77491 (IRON OXIDES); Colorona Precious Gold, Merck, Mica, Cl 77891 (Titanium dioxide), Silica, Cl 77491 (Iron oxides), Tin oxide; Colorona Sun Gold Sparkle MP 29, Merck, MICA, TITANIUM DIOXIDE, IRON OXIDES, MICA, Cl 77891, Cl 77491 (EU); Colorona Mica Black, Merck, Cl 77499 (Iron oxides), Mica, Cl 77891 (Titanium dioxide) Colorona Bright Gold, Merck, Mica, Cl 77891 (Titanium dioxide), Cl 77491 (Iron oxides); Colorona Blackstar Gold, Merck, MICA, Cl 77499 (IRON OXIDES); color pigments bearing the trade name Unipure® are, for example: Unipure Red LC 381 EM, Sensient Cl 77491 (Iron Oxides), Silica; Unipure Black LC 989 EM, Sensient, Cl 77499 (Iron Oxides), Silica; Unipure Yellow LC 182 EM, Sensient, Cl 77492 (Iron Oxides), Silica.

Among the dyes, non-limiting mention can be made of cochineal carmine. Non-limiting mention can also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), and D&C Blue 1 (CI 42 090). A non-limiting example of a lake that can be mentioned is the product known under the following name: D&C Red 7 (CI 15 850:1).

Dispersants

The dispersant can help to maximize performance in terms of maximizing the amount of color produced from an immobilized film, maximizing the remanence or wash fastness, and enabling removal of the coating irrespective of whether pigments are present or not.

The electrostatic, ionic and functional character of the dispersant is chosen to be compatible with and to not interfere with the reactive constituents of the film forming and pretreatment compositions. More preferably, the dispersant is chosen to be compatible with and miscible with the other components of the composition or compositions with and without medium.

The principle of choosing chemically similar dispersant with the binder polymer of the film forming composition can be followed to ensure maximum compatibility.

As well as compatibility as noted above, the other criterion in selecting dispersant(s) is their ability to enable pigment to be dispersed down to the primary particle size, preferably with the minimum amount of input mechanical energy. It will be recognized by someone skilled in the art that the concentration of dispersing agent is also a factor. In general, it is usually required that there is a minimum amount for dispersing activity and that below this, the composition is either not fully dispersed or the dispersant acts as a flocculant.

These two considerations together are used to define preferred materials and their respective concentrations.

It may also be the case, depending on the type of binder polymer used, that the binder itself is also a dispersant. In such cases it is possible that no further dispersing additive may be needed.

Combination of the film forming composition with the dispersed pigment mixture or with a dispersant without pigment can be made in any manner. This order of combination of with the film forming composition delivers the dispersed pigment mixture or dispersant with the film forming composition layer and on top of the pretreatment layer. While the layers intermix to a slight to moderate to essentially full extent, at least a portion of the dispersed pigment mixture or dispersant resides over the pretreatment layer. This arrangement of the coating at least in part enables removal of the coating when the "off" techniques described below are practiced.

Dispersants are amphiphilic or amphiphathic meaning that they are chemical compounds possessing both hydrophilic (water-loving, polar) and lipophilic (fat-loving) properties. Dispersants are surface-active polymers that allow the homogeneous distribution and stabilization of solids, e.g. pigments or other solid substances and dis-similar organic and/or silicon compounds in a liquid medium, by lowering the interfacial tension between the two components. As a result, agglomerates are broken up into primary particles and protected by a protecting dispersant envelope of a re-agglomeration. Included are anionic additives, neutral additive, cationic additives and steric stabilization additives. Examples include polyanionic dispersing additives: polycarboxylates (mostly salts of polyacrylic acids), polyphosphates divided into linear polyphosphates and cyclic metaphosphates, polyacrylates salts of polyacrylic acid, as cations, sodium and ammonium are preferred, these polyacrylates are water-soluble, technical products have molecular weights in the range of 2000 to 20,000 g/mol, optimum is about 8000 g/mol as well as sodium and ammonium salts of the homo- or copolymers of acrylic acid, methacrylic acid or maleic acid.

Additive Components

Additive components for the film forming composition include suspending agents, leveling agents and viscosity control agents. The suspending agents help maintain the pigment particles in dispersed condition and minimize or negate their agglomeration. Suspending agents include fatty acid esters of polyols such as polyethylene glycol and polypropylene glycol. These are similar to plasticizers and function in similar fashion to allow pigment particles to "slip" by each other without retarding or binding interaction. They act as grease in this fashion. Additionally, suspending agents in part participate in promoting the stable dispersion of the pigment particles and avoid settling. The binder and linker of the film forming composition also participate through their solubilization or interaction with the pigment particles and with the medium. The suspending agents provide another factor for maintaining the stable dispersion. They not only provide the "grease" to facilitate Brownian movement but also in part stabilize through interaction as emulsifiers of the pigment particles in the medium. Optional components also are to be chosen so that they do not interfere or only minimally interfere with the reactive polymer coupling reaction.

Embodiments of the film forming composition in accordance with the present invention can also optionally contain at least one adjuvant, chosen, for example, from reducing agents, fatty substances, softeners, antifoams, moisturizers, UV-screening agents, mineral colloids, peptizers, solubilizers, fragrances, anionic, cationic, nonionic, or amphoteric surfactants, proteins, vitamins, propellants, oxyethylenated or non-oxyethylenated waxes, paraffins, $C_{10}$-$C_{30}$ fatty acids such as stearic acid or lauric acid, and $C_{10}$-$C_{30}$ fatty amides such as lauric diethanolamide.

Embodiments of the film forming composition in accordance with the present invention can further optionally contain one or more additives, including, but not limited to, antioxidants (e.g., phenolics, secondary amines, phosphites, thioesters, and combinations thereof), non-reactive diluents (e.g., ethylene glycol, di(ethylene glycol), tetra(ethylene glycol), glycerol, 1,5-pentanediol, ethylene glycol monomethyl ether, ethylene glycol dimethyl ether, triethylene glycol monomethyl ether, 2-ethoxyethanol, solketal, benzonitrile, hexamethylphosphoramide, 2-N-methylpyrrolidinone and N,N-dimethylformamide); dyes, fillers (e.g., silica; carbon black; clay; titanium dioxide; silicates of aluminum, magnesium, calcium, sodium, potassium and mixtures thereof; carbonates of calcium, magnesium and mixtures thereof, oxides of silicon, calcium, zinc, iron, titanium, and aluminum; sulfates of calcium, barium, and lead; alumina trihydrate; magnesium hydroxide and mixtures thereof), plasticizers (e.g., petroleum oils such as ASTM D2226 aromatic oils; paraffinic and naphthenic oils; polyalkylbenzene oils; organic acid monoesters such as alkyl and alkoxyalkyl oleates and stearates; organic acid diesters such as dialkyl, dialkoxyalkyl, and alkyl aryl phthalates, terephthalates, sebacates, adipates, and glutarates; glycol diesters such as tri-, tetra-, and polyethylene glycol dialkanoates; trialkyl trimellitates; trialkyl, trialkoxyalkyl, alkyl diaryl, and triaryl phosphates; chlorinated paraffin oils; coumarone-indene resins; pine tars; vegetable oils such as castor, tall, rapeseed, and soybean oils and esters and epoxidized derivatives thereof, esters of dibasic acids (or their anhydrides) with monohydric alcohols such as o-phthalates, adipates and benzoates; and the like and combinations thereof), processing aids, ultraviolet stabilizers (e.g., a hindered amine, an o-hydroxy-phenylbenzotriazole, a 2-hydroxy-4-alkoxybenzophenone, a salicylate, a cyanoacrylate, a nickel chelate, a benzylidene malonate, oxalanilide, and combinations thereof), and combinations thereof.

An additional additive may be a tactile hair modification agent. These may include, but are not limited to, a softening and/or lubricating and/or anti-static and/or hair alignment and/or anti-frizz benefit and/or impact on the keratin fibers.

Additional additives include filler materials such as but not limited to no chromatic material with a particle size of from about 2 nm to about 500 nm; macromolecular strands or nanoparticles composed of polyolefin such as polyethylene, polypropylene, polybutene, and combinations thereof, clays and mineralite substances such as but not limited to smectites, kaolins, illites, chlorites, attapulgites and intercalated aluminosilicate materials and purified formed thereof and combinations thereof. Additional mineral microparticles may be composed of inorganic metal oxides selected from the group consisting of silica, titanium oxide, zirconium oxide, aluminum oxide, magnesium oxide, boehmite alumina, hydrotalcite. Still other filler material includes but is not limited to carbon nanotubes micrographitic material such as nanofiller of graphite oxide mixed polymer, microbucky balls, clathrates, and crown composites of organic and mineral complexes. Additionally, the filler may be combined, complexed, contain or incorporate a polymer containing one of the members of a complementary reactive pair relating to the first and second components of the reactive polymer composition.

Additives may also include but are not limited to UV filter and UV block substances such as but not limited to avobenzone, bemotrizinol octocrylene, benzophenone-4, ethylhexyl methoxycinnamate, PABA, padimate O, PBSA, cinoxate, dioxybenzone, homosalate, menthyl anthranilate, octyl salicylate, parsol Max, tinosorb S and A2B, Uvinul, amioxate, polyvinylidene fluoride and other similar conjugated organic compounds, radical scavengers, triplet formation inhibitors, metal compounds incorporating chromium, titanium, zinc, nickel, manganese, iron, niobium, silver, gold, aluminum, hafnium, tantalum such as the oxides and similar forms thereof wherein the metal compounds absorb or reflect UV light.

Praeparatur and Fundamenta Techniques

A typical procedure for coloration of anagenic hair may involve application of a permanent oxidative dye formulation or may involve semi-permanent application of a direct dye or may involve temporary coloration that can be removed by a single mild shampoo washing. These three techniques for hair coloration traditionally are applied to anagenic hair without a prior wash of the anagenic hair. The presence of sebum, fatty acids (F layer), natural oils, sweat residue, mineral excretion from skin pores are traditionally regarded as helpful in the practice of these coloration techniques. Of course, if the anagenic hair also contains dirt particles, it is usually combed thoroughly to remove dirt debris but the natural oils, secreted minerals, sebum, fatty acids and the like remain.

It is expected therefore that the remanent results demonstrated by formation of a coating according to the invention on a treated or untreated tress would also be demonstrated by formation on anagenic hair of a coating according to the invention. In contrast to this expectation, and as shown by the mimic tress experiments described below, a coating formulated onto anagenic hair such as hair on the scalp of a live hair model does not display long-lasting remanence. For the colored option, the hue, intensity and shade of the color coating on anagenic hair such as that of a model rapidly decreases with each shampooing and by 3 shampoo washes or less, the color coating is gone, especially for color coating on the root portion of anagenic hair.

In contemplation of these results, it was realized that treated and untreated tresses fundamentally differ in at least one respect from anagenic hair. The treated and untreated tresses which are the typical universal substrate for keratin fiber experimentation are not connected to hair follicles and do not receive continuous secretions of sebum, natural oils and fatty acid as well as sweat and mineral secretions from adjacent skin pores. This realization led to experimentation to improve remanence on anagenic hair by converting it to hair like that of treated and untreated tresses. These attempts involved initial removal of sebum, natural oils, fatty acid secretions, sweat and mineral secretions by detergent washing as is usually performed on cut hair being prepared for treated tresses. These attempts also failed. Subsequent body secretions appurtenant to the hair on the scalp of hair models were found to continue circumvention of the remanence result experienced with treated and untreated tresses.

Continued research has led to a combination of aspects that have enabled development of a color coating on anagenic hair that displays remanence similar to that displayed by treated and untreated tresses. These aspects include at least the techniques of Praeparatur and Fundamenta in combination with the Pretreatment Composition with small molecules described above.

In particular, for development of a long lasting color coating or a clear coating for styling and curing, use of the Praeparatur and Fundamenta techniques assure remanence. In contrast, if a color coating or clear coating is to be temporary, avoidance of use of these techniques may be practiced. In addition, an additive such as a natural oil and/or waxy substance and/or a C12-C24 saturated fatty acid optionally combined with a corresponding methyl or ethyl ester and/or a silicone oil may be applied to the hair as a thin coating. The thin coating may then be coated with the pretreatment and film forming compositions. The thin coating enables ready removal of the coating films according to the invention.

Praeparatur Technique

Substantially complete initial removal of sebum coating the surfaces of anagenic hair delivers a primed hair strand surface exposing the microscopic topographic variability provided by keratin protein at this surface. To obtain such keratin fiber priming, a Praeparatur technique is applied. The Praepartur technique may be any priming operation that removes sebum from the surfaces of keratin fibers. Exemplary Praepartur techniques include use of one or more applications of a non-conditioning surfactant which is free of conditioning actives or is substantially free of conditioning additives such as silicones, e.g., amodimethicone, or cetrimonium chloride and polymers such as the polyquaternium versions of cellulose and guar gum derivatives. This technique calls for one or more applications of a non-conditioning or substantially non-conditioning surfactant in an aqueous or aqueous-alcoholic medium with optional agents for ionicity and pH control in which the kinds and concentrations of components are adjusted to achieve the desired priming effect. The technique involves use of a mild to moderate aqueous composition of an anionic, non-ionic, amphoteric or zwitterionic surfactant at a concentration beginning at about 2 wt % and escalating to about 30 wt %, preferably up to about 25 wt %, more preferably up to about 10 wt % to about 25 wt % relative to the total weight of the composition. The surfactant composition may also include agents for adjustment of viscosity and ionicity and optional adjustment of pH from acidic to neutral to basic. The surfactant composition may begin with a mild surfactant such as a non-ionic or its mixture with other surfactants and may escalate to higher concentrations of anionic surfactant. A preferable surfactant is an anionic surfactant displaying amphiphilic properties such as an alkali metal salt of a C8-C16 alkyl carboxylate, phosphate, sulfonate, sulfate in which the strength of amphiphilic character increases from carboxylate to sulfate. The initial nonionic surfactant used may be followed by a stronger anionic surfactant and then by a solubilizing anionic surfactant having either a PEG group such as PEG-2 to PEG-20, preferably PEG-2 to PEG-5 for increased hydrophicity or a PPG group such as PPG-2 to PPG-5 for increased lipophilicity inserted between the anionic head and the alkyl lipophilic tail of the anionic surfactant. Yet stronger solubilizing media may be formulated by increasing the ionic strength and adjusting the pH. Ionicity builders such as alkali metal sulfates, carbonates, phosphates, nitrates and/or xylene sulfonate may be added. The nature of the medium may also be adjusted to provide organic solvents that are capable of solubilizing oils and sebum. Included are C2 to C8 alcohols, preferably isopropanol, isobutanol and neohexanol. This escalating priming treatment is designed to escalate in mild stepwise fashion so as to avoid overchallenge of the hair.

This escalating priming treatment may be coupled with mechanical agitation such as by a fine tooth comb and/or by a sound vibration such as with a ultrasound device operating at least at 20K Hertz. The mechanical and/or sound vibration can agitate the anagenic hair strands to loosen coatings of sebum, natural oils and secreted sweat and minerals. The ultrasound device may be designed as a fine tooth comb, the teeth of which vibrate to produce the ultrasound. Alternatively, the ultrasound device may be a hand-held generator held in combination with a fine tooth comb which is run through the anagenic hair under the above described priming conditions.

Fundamenta Technique

The Praeparatur technique often will be sufficient to prime a fiber surface and allow adherence of the pretreatment small molecule with surface exposed protein. However, application of the Praeparatur technique to anagenic hair may not fully prime the bare surface protein of keratin fibers nor will it remove the F layer fatty acid coating on anagenic hair strands. In such instances, application of the Fundamenta technique may accomplish deep cleaning of the keratin fibers such as anagenic hair. The Fundamenta technique may be applied as a follow-on to use of the Praeparatur technique or applied without prior use of the Praeparatur technique or may be applied first with subsequent use of the Praeparatur technique. The Fundamenta technique structurally deep cleans the surface topography and chemical substances of the surfaces of keratin fibers and removes the F layer coating on the keratin fibers. The technique also may but not necessarily adjust the topography of the fiber surfaces so as to enable better access of the pretreatment small molecules to the fiber surfaces. This technique may be accomplished by any deep cleaning operation that removes the F layer and deep cleans the keratin fiber surfaces. Exemplary activities include use of one or more of cold plasma discharge, an oxidizing agent and/or a phase transfer tenside such as but not limited to a multi-alkyl ammonium halide including choline or a fatty C2-C20 multi-alkyl ammonium chloride such as cetyl trimethyl ammonium halide (CTAB) or stearyl trimethyl ammonium halide (STAB).

The cold plasma treatment may be accomplished by passing partially ionized gas over anagenic hair or mimic tresses. Cold plasma is a non-equilibrium atmospheric plasma of a gas such as air or oxygen and/or nitrogen having an effective gas temperature approximating ambient temperature while the electron temperature may be much higher. The gas is passed between dielectric coated electrodes at a high AC voltage potential difference or through an RF field. The electromagnetic field dislodges some electrons from the gas atoms to produce a cascade of ionization processes which lead to the cold plasma stream. An example is an ozone generator which passes air through a high voltage spark discharge. Cold plasma generators are commercial devices designed for production of ambient temperature (cold) plasma. The plasma is transported through a flexible tube to a nozzle. The nozzle through which the plasma stream flows may be passed over the keratin fibers to accomplish plasma treatment. A typical treatment of a mimic hair tress involve passing the nozzle with flowing plasma over the keratin fibers for approximately 1 to 5 minutes, preferably about 1 to about 3 minutes.

Phase transfer tenside treatment is accomplished by washing anagenic hair and/or mimic tresses with an aqueous solution of a tenside such as an organic ammonium compound. The organic ammonium compound generically is a C2-C20 multi-alkyl ammonium halide, preferably C12-C20 alkyl trimethyl ammonium chloride or bromide, more preferably cetyl (C16) and/or stearyl (C18) trimethyl ammonium bromide (CTAB or STAB) may be formulated as a 10 wt % to 30 wt % aqueous solution. An alkali or thiol aqueous solution (basic alkali pH>10, basic thiol pH>7) of the CTAB may be applied to a mimic tress or anagenic hair and massaged through the hair strands either by hand or by brush for a period of 5 to 30 minutes, preferably 5 to 15 minutes to obtain CTAB treatment. Thereafter, the tress or anagenic hair, which has been substantially saturated with aqueous tenside, is repeatedly rinsed with shampoo in acidic medium to remove the tenside solution.

The oxidizer treatment is accomplished by exposing anagenic har or mimic tresses to a dilute oxidizer solution. The oxidizer solution may be formulated as an aqueous solution of a persulfate, hypochlorite, peroxide or ozone typically at a concentration of from about 1 wt % to about 15 wt %, preferably about 1wt % to about 12 wt %, more preferably about 2 wt % to about 12 wt %. The oxidizer solution can be at an elevated pH, due to the presence of ammonia or MEA or sodium silicate or metasilicate. The oxidizer solution is applied to a mimic tress or anagenic hair and massaged through the hair strands either by hand or by brush for a period of several minutes, preferably about 3 to 40 minutes. Thereafter the tress or anagenic hair, which has been substantially saturated with oxidizer solution, is repeatedly rinsed with water to remove the oxidizer solution.

It is believed that the Praeparatur and Fundamenta techniques enable intimate interaction of the pretreatment small molecule and the surfaces of anagenic hair strands. The Praeparatur and Fundamenta techniques prime and deep clean the hair strand surfaces to remove at least sebum and the F layer so that the small molecules are better able to adhere intimately with and within the peaks, shoulders, and valleys of the surfaces of the keratin fibers as well as with the microscopic topography involving the keratin protein in at the fiber surfaces. This ability of the small molecule is also related to its small size and reactive energy. As mentioned previously, the presence of the sebum and fatty acid F layer surrounding the surfaces of keratin fibers of anagenic hair presents a surprising problem with respect to treated and untreated tresses. The Praeparatur and Fundamenta techniques practiced in combination with the application of the pretreatment composition with small molecules enable this intimate adherence with the microscopic topography of the protein at the surfaces of the keratin fibers. Once in place, the small molecule embodiments are readily able to self-condense to form polysiloxane three dimensional networks in intimate adherence with these keratinaceous surfaces. Subsequent covalent interactions between remaining reactive groups of the condensed small molecule embodiments and the binder component of the film forming composition are believed to extend the three dimensional network. Because of the microscopic topographic adherence of the three dimensional network of condensed small molecules to the keratin surface proteins, it is believed that continued sebum and fatty acid secretions onto the keratin fiber shafts are unable to work their way (worm) underneath the network and dislodge it. The network, in turn is intimately interconnected with the three dimensional network formed through condensation of the binder of the film forming composition. The cooperation of these networks inter-adhered with the keratinaceous surfaces is believed at least in part to provide significant remanence of anagenic hair. These aspects according to the invention are believed to produce at least in part qualities and characteristics of the color coating on the keratinaceous surfaces and especially on the surfaces of hair strands of anagenic hair.

Medium

When applied to keratin fibers, the media or cosmetic carrier of the three kinds of film forming composition and pre-treatment composition embodiments of the invention may be an organic compound that is capable of being intimately mixed or preferably forming a solution with a minor amount of water. The preferred media comprise embodiments of alcoholic solvents such as an alkyl alcohol of 1 to 6 carbons with no intentionally added water. Included are methanol, ethanol, propanol, isopropanol n-butanol, isobutanol, pentanol, neopentanol, isopentanol and n-hexanol. Preferred organic alcohols include ethanol, n-propanol, isopropanol, ethylene glycol, propylene glycol, n-butanol and isobutanol and pentanol. The alcoholic solvent may be intentionally combined with water in amounts up to about 10 weight percent, preferably up to about 8 weight percent, more preferably up to about 4 or 5 weight percent relative to the total weight of the media. It is recognized that alcohol solvents absorb water from the atmosphere so that an alcoholic solvent with no intentionally added water may contain a slight amount of water. Although it is not a limitation of the invention, it is believed that the presence of water molecules facilitate the condensation of the alkoxysilyl groups to silyloxysilyl groups by hydrolyzing the alkoxy groups to hydroxyl groups. Additionally and optionally, for management of the acid-CDI reaction, control of the pH toward basic by use, for example of an amine such as trimethyl or triethyl amine or ammonia in a minor concentration such as but not limited to about 0.1 wt % to about 5 wt % relative to the medium weight may be added to the aqueous alcohol medium for the film forming composition to moderate this reaction.

Additionally, the medium for the pretreatment composition may include a minor amount of acetic acid, such as from about 0.1 wt % to about 2 wt %, preferably from about 0.1 wt % to about 1 wt %, more preferably from about 0.1 wt % to about 0.5 wt % relative to the total weight of the medium. The presence of acetic acid facilitates hydrolysis of the alkoxysilyl groups to hydroxysilyl groups and renders the small molecule of the pretreatment composition more soluble in water. When the minor amount of acetic acid is present in the aqueous-alcoholic pretreatment composition, the lifetime of the small molecule is on the order of on the order of a few hours. Consequently, this option for application of the pretreatment composition is typically conducted in small batches which are mixed and immediately used. The medium for the pretreatment composition may also include a balance among the amounts of alcohol, water and acetic acid present relative to the identity of the small molecule present. In some instances, the acid and/or water concentrations may be greater than in others. Determination of appropriate and/or optimum ratios of concentrations for the individual small molecules, the choice and amount of medium and the presence and amount of acid or base are within the ordinary experimental ability and technique of the laboratory technician.

The binder, linker and catalyst (if present) of the three kinds of film forming composition and the pretreatment composition are maintained separately until use. Packaging each in separate containers serves this purpose. Each of the binder, linker, catalyst and small molecule of the pretreatment composition may be maintained in a medium that does not interact with the reactive groups. Suitable media for the binder and linker are non-aqueous organic solvents such as but not limited to the alcohols mentioned above, preferably isopropanol and isobutanol or liquid hydrocarbon or silicone solvents. The media for separately maintaining the binder, linker, catalyst and small molecule should not include water or agents that would hydrolyze alkoxysilyl groups. Typically, the binder, linker, catalyst and small molecule preparations for storage may be formulated as ready to use concentrations or may be concentrates which are to be diluted with appropriate media to prepare them for use or may be ready to use concentrations for application to keratin fibers.

When the three kinds of film forming composition and the pretreatment composition are prepared for application to keratin fibers, they may be formulated with a single phase alcohol or alcohol medium as described above or may be formulated as a two phase aqueous medium with water or water-alcohol as the continuous phase and a water or water-alcohol immiscible organic liquid as the discontinuous phase. The continuous phase may carry water soluble constituents while the discontinuous phase may carry constituents such as those of the film forming composition and the alkoxysilyl small molecule of the pretreatment composition that would react with water. The discontinuous, non-aqueous phase will tend to isolate such compounds from degradation by water. Preferably, in situations when water is to be part of a medium but one or more of the components of the film forming composition and pretreatment composition are sensitive to water, the film forming composition and pretreatment composition are maintained in a non-aqueous environment until they are ready for dressing on keratin fibers. At the application stage, single phase or a two phase medium may be prepared as appropriate.

The polarity and protonic character of the medium are important for control of the several reactions that occur when the components of the film forming composition and pretreatment composition are combined. These reactions include the reactive termini/pendant alkoxysilyl groups which undergo alkoxysilyl condensation to form silyloxysilyl linkages. Preferably, the medium for application of the three kinds of film forming composition and the pre-treatment composition is polar and can support the condensation and addition reactions. For both of the three kinds of film forming composition and pretreatment composition, isopropanol or isobutanol with a minor amount of water as described above is appropriate. The application media may be combined with the separately stored concentrates of binder, catalyst and small molecule and the media of the stored concentrates preferably will be at least partially to substantially miscible with the application media.

The medium may be independently present in each of the film forming composition and the pretreatment composition in an amount ranging from about 0.1% to about 99% by weight, such as from about 1% to about 98% by weight, for example ranging from 50% to 95% by weight relative to the total weight of which of the film forming composition and pretreatment composition is under consideration.

As described above for use, the pretreatment composition containing the organic silicon compound(s) from the group of silanes may be in a cosmetic carrier, which may be water-containing, water-poor or also water-free. In addition, the cosmetic carrier can be liquid, gel-like, creamy, powdery, or even solid (e.g., in the form of a tablet or pellet). Preferably, the cosmetic carrier is an aqueous or aqueous-alcoholic carrier. Aqueous/alcoholic solutions in the context of the present disclosure are aqueous solutions containing from about 2 to about 70% by weight of a C1-C4 alcohol, more particularly ethanol or isopropanol. The agents as contemplated herein may additionally contain other organic solvents, such as methoxybutanol, benzyl alcohol, ethyl diglycol or 1,2-propylene glycol. Preferred are all water-soluble organic solvents. To hair coloration, such carriers are, for example, creams, emulsions, gels, or surfactant-containing foaming solutions, such as shampoos, foam aerosols, foam formulations or other preparations suitable for application to the hair.

The cosmetic carrier for the pretreatment composition in circumstances directed to use preferably contains water which means that the carrier contains at least about 2% by weight of water based on its weight. Preferably, the water content is above about 5 wt. %, further preferably above about 10 wt. % still further preferably above about 15 wt. %. The cosmetic carrier can also be aqueous alcoholic. Aqueous/alcoholic solutions in the context of the present disclosure are aqueous solutions containing from about 2 to about 70% by weight of a $C_1$-$C_4$ alcohol, more particularly ethanol or isopropanol. The agents as contemplated herein may additionally contain other organic solvents, such as methoxybutanol, benzyl alcohol, ethyl diglycol or 1,2-propylene glycol. Preferred are all water-soluble organic solvents.

However, the cosmetic carrier for the pretreatment composition preferably is anhydrous in situations involving storage, maintenance, and situations other than immediate use of agent a. The silanes of are reactive in that they hydrolyze and condense to form Si—O—Si networks. The presence of water as part of the carrier will eventually lead to hydrolysis and condensation. In situations in which the pretreatment composition is prepared for use, water may be added to the cosmetic carrier to initiate and promote the hydrolysis and condensation of the silanes. The result of the condensation of the silanes is a silicone network forming a film in situ by oligomerization or polymerization of the organic silicon compound(s). The silicone network also interacts with the hydrophobic film forming polymer by physical combination to form the overall color coating on the keratinous material.

Conditioning and Styling

When the compositions according to the invention are applied to keratin fibers as conditioning, styling and holding compositions, the compositions are easy to distribute over the hair, easy to remove according to the removal techniques and lead to shiny, smooth, soft hair that is easy to disentangle. The composition affords densification to the head of hair (gives the impression of a larger number of hairs), body, volume and ease of shaping, in particular for fine hair. Finally, the compositions according to the invention also make it possible to give curly hair styling effects, especially in terms of curl definition and control.

The styling and cosmetic properties last over time, even after shampooing several times. Accordingly, the subject of this embodiment of the invention is also the use of a composition according to the invention for caring for and shaping keratin materials, especially keratin fibers and in particular human keratin fibers such as the hair.

The incorporation of fatty esters with the pretreatment and/or film forming composition and especially with the pretreatment composition provides heightened conditioning and smoothing results for the conditioning, styling and holding aspect of the invention.

For the purposes of the present invention, the term "fatty esters" more particularly means an ester of a carboxylic acid comprising in its structure a fatty chain with at least 10 carbon atoms, preferably having from 10 to 30 carbon atoms, preferably from 10 to 22 carbon atoms, and of an alcohol which is preferably a monoalcohol, especially C1-C30, more particularly C1-C22 or a sugar.

More particularly, these compounds are chosen from: esters of saturated, linear or branched C1-C30 monoalcohols, with C10-C30 monofunctional fatty acids, the latter possibly being linear or branched, and saturated or unsaturated; esters of linear or branched C3-C8 monoalcohols, with C10-C30 difunctional fatty acids, the latter possibly being linear or branched, and saturated or unsaturated; esters and diesters of sugars and of C10-C30 fatty acids; mixtures thereof.

As regards the esters of saturated, linear or branched C1-C30 monoalcohols, with C10-C30 monofunctional fatty acids, the latter may be linear or branched, and saturated or unsaturated. If they are unsaturated, these compounds may comprise one to three conjugated or unconjugated carbon-carbon double bonds (—C.dbd.C—).

According to one preferred embodiment of the invention, these esters may be selected especially from oleate, laurate, palmitate, myristate, behenate, cocoate, stearate, linoleate, linolenate, caprate, arachidonate, or mixtures thereof, especially such as the oleopalmitates, oleostearates and palmitostearates of C1-C30 monoalcohols.

Among these esters, use may be made of branched alcohol esters such as isopropyl palmitate, isopropyl myristate, octyldodecyl stearate and isononyl isononanoate. These esters are liquid at 25.degree. C. and at atmospheric pressure (10.sup.5 Pa).

Among the esters of linear or branched C3-C8 monoalcohols, with difunctional, linear or branched, saturated or unsaturated C12-C30 fatty acids, and more particularly among the isopropyl diester of sebacic acid, also known as diisopropyl sebacate.

The composition may also comprise, as fatty ester, sugar esters and diesters of C10-C30 fatty acids. It is recalled that the term "sugar" means compounds that have several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be selected especially from the group comprising the esters or mixtures of esters of sugars described previously and of linear or branched, saturated or unsaturated C10-C.sub.22 fatty acids. If they are unsaturated, these compounds may comprise one to three conjugated or non-conjugated carbon-carbon double bonds.

The esters may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates of sugar(s), or mixtures thereof such as, especially, oleopalmitate, oleostearate and palmitostearate mixed esters of sugar(s).

More particularly, use is made of monoesters and diesters and especially sucrose, glucose or methylglucose monoooleates or dioleates, stearates, behenates, oleopalmitates, linoleates, linolenates and oleostearates.

Examples of esters or mixtures of esters of sugar and of fatty acid that may also be mentioned include: the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate; the products sold under the name Ryoto Sugar Esters, for example referenced B370 and corresponding to sucrose behenate formed from 20% monoester and 80% diester, triester and polyester; the sucrose monodipalmitostearate sold by the company Goldschmidt under the name Tegosoft® PSE.

According to one particularly preferred embodiment, the fatty esters used in the composition of the invention are preferably saturated fatty esters, i.e. esters of saturated carboxylic acids comprising at least 10 carbon atoms, and of saturated fatty monoalcohols comprising at least 10 carbon atoms. The saturated acids or monoalcohols may be linear or branched. The saturated carboxylic acids preferably comprise from 10 to 30 carbon atoms and more preferentially from 12 to 24 carbon atoms. They may optionally be hydroxylated. The saturated fatty monoalcohols preferably comprise from 10 to 30 carbon atoms and more particularly from 12 to 24 carbon atoms.

Preferably, the carboxylic acids and alcohols of these particular esters are saturated and linear.

Preferably, the fatty esters are chosen from myristyl myristate, cetyl myristate, stearyl myristate, myristyl palmitate, cetyl palmitate, stearyl palmitate, myristyl stearate, cetyl stearate, stearyl stearate and behenyl behenate, and mixtures thereof. These esters are solid at 25° C. and at atmospheric pressure ($10^5$ Pa).

Preferably, the fatty esters of the invention are solid at 25° C. and at atmospheric pressure ($10^5$ Pa).

According to the invention, the fatty ester(s) may represent from 0.01% to 10% by weight, preferably from 0.1% to 5% by weight and more particularly from 0.1% to 5% by weight relative to the total weight of the composition The weight ratio of the amount of fatty ester to the amount of small molecules of the pretreatment composition may range from 0.005 to 20, preferably from 0.01 to 10 and better still from 0.02 to 5.

Miscellaneous Statements

The invention has been described broadly and generically herein. Each of the narrower species and subgeneric groupings falling within the generic disclosure also form part of the invention. This includes the generic description of the invention with a proviso or negative limitation removing any patient matter from the genus, regardless of whether or not the excised material is specifically recited herein. The inventions, examples, results and statement of embodiments described, stated and claimed herein may have attributes and embodiments include, but not limited to, those set forth or described or referenced in this application.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed and as provided by the statements of embodiments. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims and the statements of embodiments.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document. The written description of this patent application includes all claims, examples and statements of embodiments. All claims and statements of embodiments including all original claims are hereby incorporated by reference in their entirety into the written description portion of the specification and the right is reserved to physically incorporated into the written description or any other portion of the application any and all such claims and statements of embodiments. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims and the statements of embodiments. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims and the statements of embodiments.

The specific methods and compositions described herein are representative of preferred nonlimiting embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

Unless defined otherwise, all technical and scientific terms used herein have the same meaning as commonly understood by a person of ordinary skill in the art.

What is claimed is:

1. A method for producing a colored coating on surfaces of keratin fibers comprising
priming the keratin fibers with a Praeparatur technique to remove sebum and associated substances on the keratin fiber surfaces and deep cleaning the keratin fibers with a Fundamenta technique to remove fatty acid F layers of the keratin fiber surfaces;
applying to the primed and deep cleaned keratin fibers a pretreatment composition to form a pre-coating layer on the keratin fibers; and
applying to the pre-coating layer on the keratin fibers an aza Michael film forming composition to form a composite film of a layer of the aza Michael film forming composition overlaid on the pre-coating layer on the keratin fibers; and,
converting the composite film to the colored coating on the keratin fibers;
wherein
the pretreatment composition comprises an aqueous-alcoholic cosmetic carrier and an organosilicon compound of Formula I

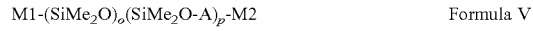

H$_2$N-L-Si(OR3)$_3$    Formula I wherein L is a linear divalent C1-C4 alkylene group and R3 is methyl, ethyl or propyl;
the aza Michael film forming composition comprises an aqueous-alcoholic cosmetic carrier, one or more pigments, a Michael binder comprising a silicone polymer having α,β-unsaturated alkenoyloxy groups according to Formula IV

H$_2$C=CHCOOCH$_2$CHOH—CH$_2$—O—(CH$_2$)$_c$—
  SiMe$_2$O—(SiMe$_2$O)$_m$—[MeSiO—(—(CH$_2$)$_c$—
  O—CH$_2$—CHOH—CH$_2$OOC—CH=CH$_2$)]$_g$
  (Me$_2$SiO)$_p$—OSiMe$_2$-(CH$_2$)$_c$—O—CH$_2$—
  CHOHCH$_2$OOCCH=CH$_2$    Formula IV wherein c is an integer of 1 to 6, m and p in Formula IV are each independently an integer of from 5 to 100, g is zero or an integer of from 1 to 10, and an aza linker comprising a silicone polymer, according to Formula V M1-(SiMe$_2$O)$_o$(SiMe$_2$O-A)$_p$-M2    Formula V wherein M1 is Me$_3$SiO or A-SiMe$_2$O and M2 is Si(OR3)$_3$, o is an integer of from 2 to 100, p in Formula V is an integer of from 1 to 10, R3 in Formula V is methyl, ethyl or propyl and A is H$_2$N—(R$^{10}$NH)$_r$—R$^{11}$—
with R$^{10}$ being a C2-C4 alkylenyl group, r being zero or an integer of 1 to 3 and R$^{11}$ being a linear C2-C5 alkylenyl group;
wherein the Michael binder and aza linker are each linear and the number of Michael binder α,β-unsaturated alkenoyloxy groups is in excess of the number of aza linker H$_2$N— groups;
wherein the Praeparatur technique comprises contacting the keratin fibers with an aqueous-alcoholic composition of an anionic surfactant selected from an alkali metal salt of a C8-C16 alkyl sulfate or a PEG 2 to PEG 20 C8-C16 alkyl sulfate or a PPG 2 to PPG 5 C8-C16 alkyl sulfate at a concentration of from 10 wt % to 30 wt % relative to the total weight of the aqueous-alcoholic composition and wherein the aqueous-alcoholic composition is free of any conditioning additive;
wherein the Fundamenta technique comprises contacting the keratin fibers with one of a cold plasma discharge of partially ionized air, oxygen and/or nitrogen, an oxidizing agent or a phase transfer tenside or any combination thereof; and,
wherein the Michael binder combines in situ with the aza linker to crosslink through the Aza-Michael addition, the Si(OR3)3 groups of the organosilicon compound of Formula I self-condense to form Si—O—Si linkages and the Si(OR3)$_3$ groups of the organosilicon compound of Formula I and the aza linker of Formula V interact to form Si—O—Si linkages.

2. The method according to claim 1 wherein the organosilicon compound of Formula I has R3 as methyl or ethyl and L as ethylenyl or propylenyl, and the Michael binder in Formula IV has g as an integer of 1 to 5, c as an integer of 1 to 3, and each of m and p independently as 10 to 50 wherein the number of Michael binder α,β-unsaturated alkenoyloxy groups is in excess of the number of aza linker H$_2$N— groups.

3. The method according to claim 2 wherein M1 in Formula V is Me$_3$SiO and p in Formula V is 2 or 3 wherein the number of Michael binder α,β-unsaturated alkenoyloxy groups is in excess of the number of aza linker H$_2$N— groups.

4. The method according to claim 1 further comprising treating the keratin fibers with a long chain fatty acid and/or its methyl or ethyl ester after application of the Praeparatur and Fundamenta techniques and before application of the pretreatment composition so that the colored coating on the keratin fibers is rendered removable with shampoo.

5. The method according to claim 1 further comprising combining with the aza-Michael film forming composition, one or more of a dispersing agent, a suspending agent, an antioxidant, a non-reactive diluent, a dye, a filler, a plasticizer, a processing aid, a ultraviolet stabilizer, a reducing agent, a fatty substance, a softener, an antifoam, a moisturizer, a fragrance, a surfactant, a vitamin, a wax, a C10-C30 fatty acid, a C10-C30 fatty amide or any combination thereof.

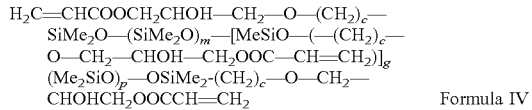

* * * * *